(12) United States Patent
Havlicek et al.

(10) Patent No.: US 9,023,857 B2
(45) Date of Patent: *May 5, 2015

(54) SUBSTITUTED 6-(2-AMINOBENZYLAMINO)PURINE DERIVATIVES, THEIR USE AS MEDICAMENTS AND PREPARATIONS CONTAINING THESE COMPOUNDS

(75) Inventors: Libor Havlicek, Prague (CZ); Vladimir Krystof, Olomouc (CZ); Marek Zatloukal, Sumperk (CZ); Karel Dolezal, Hlubocky (CZ); Miroslav Strnad, Olomouc (CZ); Borivoj Vojtesek, Modrice (CZ)

(73) Assignee: Univerzita Palackeho V Olomouci, Olomouc (CZ)

( * ) Notice: Subject to any disclaimer, the term of this patent is extended or adjusted under 35 U.S.C. 154(b) by 418 days.

This patent is subject to a terminal disclaimer.

(21) Appl. No.: 13/146,339

(22) PCT Filed: Jan. 22, 2010

(86) PCT No.: PCT/CZ2010/000004
§ 371 (c)(1),
(2), (4) Date: Aug. 10, 2011

(87) PCT Pub. No.: WO2010/085924
PCT Pub. Date: Aug. 5, 2010

(65) Prior Publication Data
US 2011/0287111 A1    Nov. 24, 2011

(30) Foreign Application Priority Data
Jan. 28, 2009 (CZ) ........................................ 2009-45

(51) Int. Cl.
*A61K 31/52* (2006.01)
*C07D 473/16* (2006.01)

(52) U.S. Cl.
CPC ............... *C07D 473/16* (2013.01); *A61K 31/52* (2013.01)

(58) Field of Classification Search
CPC ............................. C07D 473/16; A61K 31/52
USPC ........................................ 544/277; 514/263.4
See application file for complete search history.

(56) References Cited

U.S. PATENT DOCUMENTS

| 7,135,550 | B2 * | 11/2006 | Come et al. .................... 530/350 |
| 8,492,391 | B2 * | 7/2013 | Zatloukal et al. .......... 514/263.4 |
| 2003/0187261 | A1 * | 10/2003 | Havlicek et al. .............. 544/276 |
| 2010/0129321 | A1 * | 5/2010 | Weber et al. .................. 424/85.6 |

OTHER PUBLICATIONS

Wermuth, Camille G. "Molecular Variations Based on Isoteric Replacements." The Practice of Medicinal Chemistry. Academic Press, 1996. pp. 203-237.*
Gray, Nathanael S. Tetrahedron Letters, vol. 38, No. 7, pp. 1161-1164, 1997.*
Krystof, V. CMLS, Cell. Mol. Life Sci. 62 (2005) 1763-1771.*
Knockaert, Marie. Trends in Pharmacological Sciences vol. 23 No. 9 (2002) 417-425.*
MedicineNet. 2004. <http://www.medterms.com>.*
WebMd. Bacterial and Viral Infections. 2013 < http://www.webmd.com/a-to-z-guides/bacterial-and-viral-infections?page=2>.*
CDC: About Epstein-Barr Virus. 2014. <http://www.cdc.gov/epstein-barr/about-ebv.html.*
CDC: Adenoviruses. 2014. <http://www.cdc.gov/adenovirus/about/prevention-treatment.html>.*
CDC: Genital HPV Infection. 2014. <http://www.cdc.gov/std/hpv/stdfact-hpv.htm>.*

* cited by examiner

*Primary Examiner* — Golam M M Shameem
*Assistant Examiner* — Laura Daniel
(74) *Attorney, Agent, or Firm* — Notaro, Michalos & Zaccaria P.C.

(57) ABSTRACT

The invention relates to new substituted 6-(2-aminobenzylamino)purines, represented by the general formula I, which can be used in CDK inhibition, in particular, in the treatment of viral infections and diseases involving cell proliferation. The invention further includes pharmaceutical preparations containing substituted 6-(2-aminobenzylamino)purines.

9 Claims, 11 Drawing Sheets

A

B

C

(I)

SUBSTITUTED 6-(2-AMINOBENZYLAMINO)PURINE DERIVATIVES, THEIR USE AS MEDICAMENTS AND PREPARATIONS CONTAINING THESE COMPOUNDS

FIELD OF ART

This invention relates to novel purine derivatives and to their use, particularly in viral and cancer therapy.

BACKGROUND ART

Deregulation of the mechanisms controlling cell-cycle progression is a hallmark of neoplasia. Cyclin-dependent kinases (CDKs) constitute a family of well conserved serine/threonine protein kinases which are active in complexes with their regulatory subunits, the cyclins. The human genome encodes 13 CDKs, 48 CDK related kinases and 25 cyclins. The different members of the CDK family have been implicated in a range of key cellular processes: CDK1, 2, 3, 4, 6, and 7 regulate the cell cycle, CDK7, 8, and 9 interact directly with transcription factors, CDK5 and 11 control neuronal functions, CDK2, 5, 6, and 9 cell differentiation and CDK1, 2, 4, 5, 6, and 11 affect apoptosis (Knockaert et al.: J. Biol. Chem. 277: 25493-25501, 2002). CDK functions are regulated by cyclins, CDK inhibitory proteins and subcellular localization. Since many CDKs are critical regulators of cell division, the pharmaceutical industry has been targeting the discovery and development of pharmacological CDK inhibitors (CDKIs) as potential anticancer drugs. CDKIs are a diverse and heterogeneous family of small, flat heterocycles-purines, pyrimidines, flavonoids or bis-indoles that bind to the ATP binding pocket of their target CDK where they can compete with the ATP (de Azevedo et al., Eur. J. Biochem. 243:518-526, 1997).

The key regulators of the cycle are represented by 3 groups of proteins: cyclins, cyclin-dependent kinases (CDK) and cyclin-dependent kinase inhibitors (CDKI).

The earliest significant CDKIs were the CDK oligo-specific Olomoucine and the CDK pan-specific Flavopiridol (Losiewicz et al., Biochem. Biophys. Res. Commun. 201(2): 589-95, 1994). Olomoucine belongs to C2, N6, N9-substituted adenines that show high efficiency and selectivity towards some CDKs; Olomoucine specifically inhibits CDK2, CDK5, and to a lesser extent Erk1 (Veselý et al., Eur. J. Biochem. 224: 771-786, 1994). With the specific objective of attaining enhanced inhibition of CDKs, Olomoucine was subjected to structural modifications. A classical structure-activity relationship study directed at modifying Olomoucine side chains generated two exceptionally potent CDKIs: Roscovitine (Seliciclib®, CYC202, Cyclacel Pharmaceuticals, Berkeley Heights, N.J.) and most recently Olomoucine II (Havlíček et al. 1997. J. Med. Chem. 40: 408-412; Kryštof et al. Bioorg Med Chem Lett 12: 3283-3286, 2002).

The increased potency of Roscovitine over Olomoucine is caused by the introduction of branched C2-side chain and more bulky N9-isopropyl moiety. These changes markedly increased the complementarity of the inhibitor to the ATP-binding site of CDK2, as demonstrated by X-ray crystallography (de Azevedo et al. Eur. J. Biochem. 243:518-526, 1997). Both structural changes did not alter the selectivity of Roscovitine, but increased the cellular potency of Roscovitine 10-fold towards CDK1 and CDK2, and 20-fold towards CDK5. Olomoucine II differs from Roscovitine in having an additional ortho-hydroxyl group on the benzyl ring, yet this single modification is associated with a 10-fold higher inhibitory activity for CDK9 (Kryštof et al., Cell Mol Life Sci. 62: 1763-1771, 2005). This increased affinity of Olomoucine II towards CDK9 is responsible for its enhanced effect on intracellular functional activities, when compared to Roscovitine. For example, Olomoucine II induces the nuclear accumulation and transcriptional activation of the tumor suppressor protein p53 at 2-3-fold lower concentrations than Roscovitine. At higher concentrations both inhibitors may inhibit some RNA synthesis by attenuating CTD domain phosphorylation of RNA polymerase II (Diwan et al., J Virol. 78: 9352-65, 2004).

The finding that Roscovitine possessed antiviral activity stimulated research aimed at targeting cellular functions, exemplified by CDKs, required for virus replication (Bresnahan et al., J. Gen. Virol. 78:1993-7, 1997; Schang et al., J Virol. 73:2161-72, 1999). Roscovitine, and other CDKIs, have the ability to inhibit replication of broad range of viruses, even in non-dividing cells and including agents that do not require cell cycle progression (Schang et al., Antivir. Chem. Chemother. 17:293-320, 2006). Human cytomegalovirus (HCMV), herpes simplex types 1 and 2 (HSV-1 & HSV-2), varicella zoster virus (VZV), Epstein Barr virus (EBV), human adenovirus (HAdV), human immunodeficiency virus (HIV), and human T cell leukemia virus (HTLV-1) are all susceptible to Roscovitine. Antiviral activities of CDK inhibitors correlate with the extent of CDK inhibition, rather than the core structure of the inhibitor (Schang et al., Antivir. Chem. Chemother. 17:293-320, 2006).

Although CDKIs were shown to inhibit multiple stages of viral replication, including splicing, DNA replication, reactivation from latency, activation of cellular or viral enzymes and intracellular trafficking, it is recognized that the antiviral activity of CDKIs is primarily mediated by inhibiting virus-encoded transcription (Kapasi and Spector, J. Virol. 82(1): 394-407, 2008). Interestingly, Roscovitine can prevent initiation of viral transcription that is specific to viral genomes and independent of promoter elements (Diwan et al., J. Virol. 78: 9352-65, 2004). While Flavopiridol is CDK panspecific and inhibits transcription of most cellular and viral genes, Roscovitine is CDK oligospecific and appears not to inhibit the cellular transcription. The selectivity of Roscovitine in suppressing viral and plasmid encoded gene expression resembles an activity described for interferon alpha (Nicholl and Preston, J. Virol. 70: 6336-9, 1996). In this context it is interesting to note that interferon alpha also inhibits CDKs and promotes cell cycle arrest (Mandal et al., Oncogene 16:217-225, 1998).

The mechanisms by which CDKIs suppress virus replication have not been fully defined and can be expected to differ between agents. Consequently, it was extremely important to compare and contrast the potential antiviral properties of Roscovitine and its analogues empirically. Our previous studies had determined that Olomoucine II and many other compounds were more potent inhibitors of CDK activities than Roscovitine (Kryštof et al., Cell Mol Life Sci. 62: 1763-1771, 2005).

DISCLOSURE OF THE INVENTION

Within the range of the present invention, it was found that Olomoucine II amino analogues inhibit virus-encoded transcription and virus replication at substantially lower concentrations than Roscovitine. In addition, these compounds exhibit antiviral activity across a wide range of human viruses, including orthopoxvirus, HAdV, HSV-1 and HCMV. Consistent with prior observations made with Roscovitine (Diwan et al., J Virol. 78:9352-65, 2004), the compounds were effective on viral promoters that were not incorporated into the cellular genomes. Furthermore, we demonstrate that the compounds and Cidofovir exerted a synergistic effect on adenovirus-infected cells when these two drugs were used in combination.

Substituted 6-(2-aminobenzylamino)purine derivatives according to this invention are useful for inhibition of cyclin-dependent kinase 9. This group of novel purine derivatives is characterised by selective CDK9 inhibitory activity, thus bringing very strong anticancer properties, mainly for virus-mediated cancers. Hence they can be used as antimitotic and apoptotic drugs, particularly as anticancer drugs. It is an object of this invention to provide compounds having anti-cancer and antiviral activity, compounds having improved selectivity and efficiency index, i.e. that are less toxic yet more efficacious than analogues known heretofore. Furthermore, the compounds provided by this invention inhibit virus-encoded transcription and replication more potently then any other derivatives described in prior art.

The object of the present invention are substituted 6-(2-aminobenzylamino)purines of general formula I

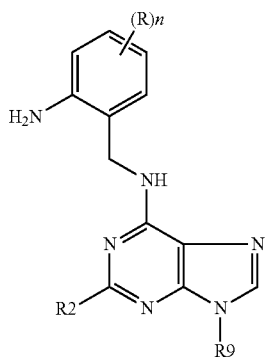

I wherein $(R)_n$ represents 1 to 4 substituents (n is 1-4), which can be the same or different, the substituents being selected from the group comprising hydrogen, alkyl, alkoxy, amino, halogen, hydroxy, nitro and mercapto group,
and
R2 is R2'-NH— wherein
R2' is selected from the group comprising alkyl, alkenyl, cycloalkyl, cycloalkyl alkyl, aryl and arylalkyl, wherein each of the groups can optionally be substituted by one or more substituents selected from the group comprising amino, halogen, hydroxy, alkoxy or mercapto group, and
R9 is selected from the group comprising alkyl, alkenyl, cycloalkyl, cycloalkyl alkyl, aryl and arylalkyl group, wherein each of the groups can optionally be substituted by one or more substituents selected from the group comprising amino, halogen, hydroxy, alkoxy or mercapto group,
and pharmaceutically acceptable salts thereof with alkali metals, ammonia or amines, or their addition salts with acids.

In case there is an enantiomeric carbon in the molecule, this invention includes also racemates as well as optically active isomers and their mixtures.

As used herein, the generic substituent groups have meanings defined in this legend, wherein:
alkoxy denotes the group —O—$R_a$, wherein $R_a$ is alkyl, or cycloalkyl,
amino denotes the group —$NH_2$,
halogen is selected from the group comprising fluorine, bromine, chlorine and iodine atom,
hydroxy denotes the group —OH,
mercapto denotes the group —SH,
nitro denotes the group —$NO_2$,
alkyl denotes
  linear or branched alkyl chain containing 1 to 8 carbon atoms, preferably selected from the group comprising methyl, ethyl, propyl, isopropyl, butyl, isobutyl, pentyl, isopentyl, hexyl, isohexyl,
alkenyl denotes
  linear or branched alkenyl chain containing 2 to 7 carbon atoms, preferably selected from the group comprising vinyl, allyl, 1-propenyl, 1-methylethenyl, but-1 to 3-enyl, pent-1 to 4-enyl, isopentenyl, hex-1 to 5-enyl, hept-1 to 6-enyl,
cycloalkyl denotes
  monocyclic or polycyclic alkyl group containing 3 to 15 carbon atoms, preferably cyclopropyl, cyclohexyl or cyclopentyl,
cycloalkyl alkyl denotes
  group —$R_b$(cycloalkyl) wherein cycloalkyl refers to a cycloalkyl group as defined above and $R_b$ is a bridging alkylene group containing 1 to 6 carbon atoms,
aryl denotes
  aromatic carbocyclic group containing 6 to 18 carbon atoms, which is formed by at least one aromatic ring or multiple condensed rings, from which at least one ring is aromatic, preferably, aryl is phenyl,
arylalkyl denotes
  group —$R_c$—Ar, wherein Ar refers to an aryl group and $R_c$ is a bridging alkylene group containing 1 to 6 carbon atoms, preferably, arylalkyl is benzyl.

It is an object of this invention to provide substituted 6-(2-aminobenzylamino)purines of the general formula I for use as medicaments.

It is an object of this invention to provide substituted 6-(2-aminobenzylamino)purines of the general formula I for use in the inhibition of the CDKs. The compounds of the formula I and their pharmaceutically acceptable salts inhibit particularly selectively the enzyme CDK9.

The novel derivatives of the general formula I show a very high activity against animal and human RNA and DNA viruses. The novel derivatives show an antiviral activity towards a wide range of viruses, particularly human viruses, such as othopoxviruses, HAdV, HSV1 and HCMV.

It is also an object of this invention to provide the novel derivatives of the general formula for use in the treatment of viral infections. Another aspect of this invention are the substituted 6-(2-aminobenzylamino)purines of the general formula I for use in the preparation of a medicament destined for the treatment of viral infections.

Moreover, surprisingly the chirally enriched or pure (S)-enantiomer is antivirally more active while the (R)-enantiomer was notably less antivirally active. An important aspect of the present invention is a method for inhibiting proliferation of a DNA virus dependent upon events associated with cell proliferation for replication. The DNA viruses include any of the herpesvirus family, and most particularly human cytomegalovirus. The method involves administering prophylactically or therapeutically effective amount of a CDK inhibitor to a patient or animal. The therapeutically effective amount is that sufficient to inhibit cellular CDK9 activity to the extent impending viral replication. Other herpesviruses such as herpes simplex, for example, and other cytomegalovirus are also treatable by the procedures of the present invention.

Exemplary viral infections include infections caused by DNA or RNA viruses including herpesviruses (herpes simplex virus type 1 (HSV-1), HSV-2), varicella zoster virus (VZV), Epstein-Barr virus (EBV), cytomegalovirus (CMV), human herpesvirus type 6 (HHV-6), HHV-7, HHV-8, bovine herpesvirus type 1, equine herpesvirus type 1, papillomaviruses (HPV types 1-55, including carcinogenic HPV), flaviviruses (including yellow fever virus, African swine fever virus and Japanese encephalitis virus), togaviruses (including Venezuelan equine encephalomyelitis virus), influenza viruses (types A-C), retroviruses (HIV-1, HIV-2, HTLV-I, HTLV-II, SIV, FeLV, FIV, MoMSV), adenoviruses (types 1-8), human adenovirus (HadV), poxviruses (vaccinia virus), enteroviruses (poliovirus types 1-3, Coxsackie, hepatitis A virus, and ECHO virus), gastroenteritis viruses (Norwalk viruses, rotaviruses), hantaviruses (Hantaan virus), polyomavirus, papovaviruses, rhinoviruses, parainfluenza virus types 1-4, rabies viruses, respiratory synctial virus (RSV), hepatitis viruses A, B, C and E, human immunodeficiency virus (HIV), human T cell leukemia virus (HTLV-1), orthopoxvirus and the like.

The object of this invention is also the use of the substituted 6-(2-aminobenzylamino)purine derivatives of the general formula I in the treatment of viral infections caused by DNA viruses, in combination with commonly used virostatics, such as acyclovir, cidofovir, tamiflu, and ribavirin.

The antiviral activity of individual compounds can be determined by routine assays of antiviral (or other antimicrobial) activity using enzyme inhibition assays, tissue culture assays, animal model assays and the like as will be understood by those skilled in the art.

The compounds of the invention can also be (1) applied to tissue culture systems to eliminate or reduce viral spread or growth during the production of biopharmaceutical or other products (such as proteins or vaccines), (2) used to eliminate or reduce viral spread or growth in clinical samples (such as blood), and (3) used to stop growth of tissue culture cells while leaving the cells to carry on with protein production. An aspect of the invention are thus the substituted 6-(2-aminobenzylamino)purine derivatives of the general formula I for use in elimination or reduction of viral spread or growth in tissue culture systems during the production of biopharmaceutical or other products, such as proteins and vaccines, in elimination or reduction of viral spread or growth in clinical samples, such as, e.g., blood, or in stopping the growth of tissue culture cells while leaving the cells to carry on with protein and secondary metabolites (antibiotics, secondary plant products, etc.) production, as well as methods of elimination or reduction of viral spread or growth in tissue culture systems during the production of biopharmaceutical or other products, such as proteins and vaccines, methods of elimination or reduction of viral spread or growth in clinical samples, such as, e.g., blood, and methods of stopping the growth of tissue culture cells while leaving the cells to carry on with protein and secondary metabolites production using the substituted 6-(2-aminobenzylamino)purine derivatives of the general formula I.

It is another object of this invention to provide substituted 6-(2-aminobenzylamino)purines of the general formula I for use for inhibiting cell proliferation and/or inducing apoptosis. In another embodiment, this invention is a method for inhibiting CDKs, particularly for selectively inhibiting CDK9, and cell proliferation and/or for inducing apoptosis in mammals, comprising administering a therapeutically effective amount of the composition of the general formula I to the mammal in need of such treatment.

It is a further object of this invention to provide substituted 6-(2-aminobenzylamino)purines of the general formula I for use in the manufacture of a medicament for the treatment of disorders which involve cell proliferation, such as cancer, restenosis, psoriasis, rheumatoid arthritis, lupus, type I diabetes, multiple sclerosis, Alzheimer's disease, parasitoses caused by animal, funghi and protists, polycystic kidney disease, graft rejection (host versus graft disease), graft versus host disease, gout, and proliferative skin diseases.

In addition to other CDK-related kinases, the CDK9 kinase controls certain steps of cell division cycles, in particular the transition from the $G_1$ phase into the S phase and in particular the transition from the $G_2$ phase into the M-phase. The compounds of the formula I and their pharmaceutically acceptable salts can be used as antimitotic compounds and for the treatment of proliferative diseases. Thus in very low concentration (micromolar and lower), they are capable of inhibiting cell cycle transitions ($G_1$/S, $G_2$/M, M-phase/metaphase) occurring in animal bodies and embryos. Furthermore, the compounds are useful in treating auto-immune diseases, e.g. rheumatoid arthritis, lupus, type I diabetes, multiple sclerosis; in treating Alzheimer's disease, cardiovascular diseases such as restenosis, graft rejection (host vs. graft disease), graft vs. host disease, gout; and in treating cancer, polycystic kidney disease and other proliferative diseases whose pathogenesis involves abnormal cell proliferation.

Substituted-6-(2-aminobenzylamino)purines derivatives can be used in the treatment of disorders, the pathogenesis of which involves cell proliferation, in combination with usually used cytostatics, such as mitoxantrone, cis-platinum, methotrexate, taxol, or doxorubicin.

In addition to therapeutic applications (for both human and veterinary use), the compounds of the general formula I can be used as a cell culture additive for controlling proliferative and/or differentiation states of cells in vitro, for instance, by controlling the level of activation of a CDK9.

Another object of the invention is also the use of substituted 6-(2-aminobenzylamino)purine derivatives of the general formula I for the inhibition of the catalytic activity of cyclin-dependent kinases, mediated by the interaction of the compounds at the ATP-binding site of the enzyme. Such compounds are particularly desirable for reducing excessive cell growth, since they allow inhibition of the kinase activity regardless of the cause underlying the excessive kinase activity leading to hyperproliferation. Thus, the compounds of the invention are active in situations, in which the excessive kinase activity results from the kinase being a mutated hyperactive form of the kinase, and in situations, in which the kinase is present at excessive levels. The compounds of the invention can also block the excessive kinase activity in situations, in which the cyclin regulating the kinase is present at excessive levels, is mutated, or its binding to the kinase is enhanced. Furthermore, the compounds of the present invention, which block kinase activity by interacting with the ATP binding site of the enzyme, are also useful for inhibiting kinase activity in situations in which a natural inhibitor of cyclin-kinase complexes is mutated.

A further object of the invention is the use of substituted 6-(2-aminobenzylamino)purine derivatives of the general formula I for activation of p53, the mammal cell's own natural suppressor gene for stopping uncontrolled cell proliferation (cancer), thus being able to switch off the cancer development. p53 as well as retinoblastoma protein (pRb) are two well characterized tumour suppressors whose inactivation may lead to uncontrolled cell proliferation and malignancy. Phosphorylation of these two proteins, which are involved in the cell cycle regulatory mechanisms, is known to significantly modulate their function. Thus, a potent p53 regulators represent a good tool for treatment of cancers due to induction of wild type p53 protein in selected cancers.

Studies carried out on the derivatives of the invention have demonstrated, in addition, a strong effect on the apoptosis of many cancer cell lines. It has been observed that apoptosis can be induced at stage $G_1$ or $G_2$ and following DNA damage; some cells stop at stage $G_1$ and p53-dependent apoptotic pathway is then induced. In other situations, it seems that cells stop at $G_2$/M stage in response to damage caused to DNA, and activation of an independent p53 apoptotic path is then observed. This path has proved particularly significant in the therapy of tumours in which lack of active p53 is observed. Thus, it is important, that by application of the derivatives of the invention, p53-independent apoptosis will be stimulated in cells, which have stopped at stage $G_2$ through DNA damage using agents such as mitoxantrone or cis-platinum. The CDK inhibitors of this invention can thus increase the therapeutic potential of the anti-tumour agents currently used.

Another object of the present invention is a pharmaceutical preparation containing at least one substituted 6-(2-aminobenzylamino) purine derivative of the general formula I and a pharmaceutically acceptable carrier.

Novel compounds of the present invention can be used as such, or as intermediates in the preparation of new compounds having a variety of diagnostic, therapeutic and industrial uses.

The following derivatives are particularly preferred, namely: 2-({6-[(2-aminobenzyl)amino]-9-methyl-9H-purin-2-yl}amino)butan-1-ol, 2-({6-[(2-aminobenzyl)amino]-9-ethyl-9H-purin-2-yl}amino)butan-1-ol, 2-({6-[(2-aminobenzyl)amino]-9-isopropyl-9H-purin-2-yl}amino)butan-1-ol, 2-({6-[(2-aminobenzyl)amino]-9-cyclohexyl-9H-purin-2-yl}amino)butan-1-ol, 2-({6-[(2-aminobenzyl)amino]-9-benzyl-9H-purin-2-yl}amino)butan-1-ol, $N^6$-(2-aminobenzyl)-$N^2$-(2-aminopropyl)-9-methyl-9H-purine-2,6-diamine, $N^6$-(2-aminobenzyl)-$N^2$-(2-aminopropyl)-9-ethyl-9H-purine-2,6-diamine, $N^6$-(2-aminobenzyl)-$N^2$-(2-aminopropyl)-9-isopropyl-9H-purine-2,6-diamine, $N^6$-(2-aminobenzyl)-$N^2$-(2-aminopropyl)-9-cyclohexyl-9H-purine-2,6-diamine, $N^6$-(2-aminobenzyl)-$N^2$-(2-aminopropyl)-9-benzyl-9H-purine-2,6-diamine, 2-({6-[(2-aminobenzyl)amino]-9-methyl-9H-purin-2-yl}amino)-3-methyl-butan-1-ol, 2-({6-[(2-aminobenzyl)amino]-9-ethyl-9H-purin-2-yl}amino)-3-methyl-butan-1-ol, 2-({6-[(2-aminobenzyl)amino]-9-isopropyl-9H-purin-2-yl}amino)-3-methyl-butan-1-ol, 2-({6-[(2-aminobenzyl)amino]-9-cyclohexyl-9H-purin-2-yl}amino)-3-methyl-butan-1-ol, 2-({6-[(2-aminobenzyl)amino]-9-benzyl-9H-purin-2-yl}amino)-3-methyl-butan-1-ol, 1-({6-[(2-aminobenzyl)amino]-9-methyl-9H-purin-2-yl}amino)propan-2-ol, 1-({6-[(2-aminobenzyl)amino]-9-ethyl-9H-purin-2-yl}amino)propan-2-ol, 1-({6-[(2-aminobenzyl)amino]-9-isopropyl-9H-purin-2-yl}amino)propan-2-ol, 1-({6-[(2-aminobenzyl)amino]-9-cyclohexyl-9H-purin-2-yl}amino)propan-2-ol, 1-({6-[(2-aminobenzyl)amino]-9-benzyl-9H-purin-2-yl}amino)propan-2-ol, $N^6$-(2-aminobenzyl)-$N^2$-(4-aminocyclohexyl)-9-methyl-9H-purine-2,6-diamine, $N^6$-(2-aminobenzyl)-$N^2$-(4-aminocyclohexyl)-9-ethyl-9H-purine-2,6-diamine, $N^6$-(2-aminobenzyl)-$N^2$-(4-aminocyclohexyl)-9-isopropyl-9H-purine-2,6-diamine, $N^6$-(2-aminobenzyl)-$N^2$-(4-aminocyclohexyl)-9-cyclohexyl-9H-purine-2,6-diamine, $N^6$-(2-aminobenzyl)-$N^2$-(4-aminocyclohexyl)-9-benzyl-9H-purine-2,6-diamine, 1-({6-[(2-aminobenzyl)amino]-9-methyl-9H-purin-2-yl}amino)-2-methyl-propan-2-ol, 1-({6-[(2-aminobenzyl)amino]-9-ethyl-9H-purin-2-yl}amino)-2-methyl-propan-2-ol, 1-({6-[(2-aminobenzyl)amino]-9-isopropyl-9H-purin-2-yl}amino)-2-methyl-propan-2-ol, 1-({6-[(2-aminobenzyl)amino]-9-(3-pentyl)-9H-purin-2-yl}amino)-2-methyl-propan-2-ol, 3-({6-[(2-aminobenzyl)amino]-9-methyl-9H-purin-2-yl}amino)-2-methyl-butan-2-ol, 3-({6-[(2-aminobenzyl)amino]-9-ethyl-9H-purin-2-yl}amino)-2-methyl-butan-2-ol, 3-({6-[(2-aminobenzyl)amino]-9-isopropyl-9H-purin-2-yl}amino)-2-methyl-butan-2-ol, 3-({6-[(2-aminobenzyl)amino]-9-cyclohexyl-9H-purin-2-yl}amino)-2-methyl-butan-2-ol, 3-({6-[(2-aminobenzyl)amino]-9-benzyl-9H-purin-2-yl}amino)-2-methyl-butan-2-ol, 4-({6-[(2-aminobenzyl)amino]-9-methyl-9H-purin-2-yl}amino)-2-methyl-butan-2-ol, 4-({6-[(2-aminobenzyl)amino]-9-ethyl-9H-purin-2-yl}amino)-2-methyl-butan-2-ol, 4-({6-[(2-aminobenzyl)amino]-9-isopropyl-9H-purin-2-yl}amino)-2-methyl-butan-2-ol, 4-({6-[(2-aminobenzyl)amino]-9-cyclohexyl-9H-purin-2-yl}amino)-2-methyl-butan-2-ol, 4-({6-[(2-aminobenzyl)amino]-9-benzyl-9H-purin-2-yl}amino)-2-methyl-butan-2-ol, 4-({6-[(2-aminobenzyl)amino]-9-methyl-9H-purin-2-yl}amino)-2-methyl-pentan-2-ol, 4-({6-[(2-aminobenzyl)amino]-9-ethyl-9H-purin-2-yl}amino)-2-methyl-pentan-2-ol, 4-({6-[(2-aminobenzyl)amino]-9-isopropyl-9H-purin-2-yl}amino)-2-methyl-pentan-2-ol, 4-({6-[(2-aminobenzyl)amino]-9-cyclohexyl-9H-purin-2-yl}amino)-2-methyl-pentan-2-ol, 4-({6-[(2-aminobenzyl)amino]-9-benzyl-9H-purin-2-yl}amino)-2-methyl-pentan-2-ol, 4-({6-[(2-aminobenzyl)amino]-9-methyl-9H-purin-2-yl}amino)-2,3-dimethyl-butan-2-ol, 4-({6-[(2-aminobenzyl)amino]-9-ethyl-9H-purin-2-yl}amino)-2,3-dimethyl-butan-2-ol, 4-({6-[(2-aminobenzyl)amino]-9-isopropyl-9H-purin-2-yl}amino)-2,3-dimethyl-butan-2-ol, 4-({6-[(2-aminobenzyl)amino]-9-cyclohexyl-9H-purin-2-yl}amino)-2,3-dimethyl-butan-2-ol, 4-({6-[(2-aminobenzyl)amino]-9-benzyl-9H-purin-2-yl}amino)-2,3-dimethyl-butan-2-ol, 3-({6-[(2-aminobenzyl)amino]-9-methyl-9H-purin-2-yl}amino)-2-methyl-pentan-2-ol, 3-({6-[(2-aminobenzyl)amino]-9-ethyl-9H-purin-2-yl}amino)-2-methyl-pentan-2-ol, 3-({6-[(2-aminobenzyl)amino]-9-isopropyl-9H-purin-2-yl}amino)-2-methyl-pentan-2-ol, 3-({6-[(2-aminobenzyl)amino]-9-cyclohexyl-9H-purin-2-yl}amino)-2-methyl-pentan-2-ol, 3-({6-[(2-aminobenzyl)amino]-9-benzyl-9H-purin-2-yl}amino)-2-methyl-pentan-2-ol, 3-({6-[(2-aminobenzyl)amino]-9-methyl-9H-purin-2-yl]amino}pentan-2-ol, 3-({6-[(2-aminobenzyl)amino]-9-ethyl-9H-purin-2-yl]amino}pentan-2-ol, 3-({6-[(2-aminobenzyl)amino]-9-isopropyl-9H-purin-2-yl]amino}pentan-2-ol, 3-({6-[(2-aminobenzyl)amino]-9-cyclohexyl-9H-purin-2-yl]amino}pentan-2-ol, 3-({6-[(2-aminobenzyl)amino]-9-benzyl-9H-purin-2-yl]amino}pentan-2-ol, 1-({6-[(2-aminobenzyl)amino]-9-cyclopropyl-9H-purin-2-yl}amino)-2-methyl-propan-2-ol, 1-({6-[(2-aminobenzyl)amino]-9-cyclohexyl-9H-purin-2-yl}amino)-2-methyl-propan-2-ol, 1-({6-[(2-aminobenzyl)amino]-9-benzyl-9H-purin-2-yl}amino)-2-methyl-propan-2-ol, 2-({6-[(2-amino-5-chlorobenzyl)amino]-9-methyl-9H-purin-2-yl}amino)butan-1-ol, 2-({6-[(2-amino-5-chlorobenzyl)amino]-9-ethyl-9H-purin-2-yl}amino)butan-1-ol, 2-({6-[(2-amino-5-chlorobenzyl)amino]-9-cyclohexyl-9H-purin-2-yl}amino)butan-1-ol, 2-({6-[(2-amino-5-chlorobenzyl)amino]-9-benzyl-9H-purin-2-yl}amino)butan-1-ol, 1$N^6$-(2-amino-5-chlorobenzyl)-$N^2$-(2-aminopropyl)-9-methyl-9H-purine-2,6-diamine, $N^6$-(2-amino-5-chlorobenzyl)-$N^2$-(2-aminopropyl)-9-ethyl-9H-purine-2,6-diamine, $N^6$-(2-amino-5-chlorobenzyl)-$N^2$-(2-aminopropyl)-9-isopropyl-9H-purine-2,6-diamine, $N^6$-(2-amino-5-chlorobenzyl)-$N^2$-(2-aminopropyl)-9-cyclohexyl-9H-purine-2,6-diamine, $N^6$-(2-amino-5-chlorobenzyl)-$N^2$-(2-aminopropyl)-9-benzyl-9H-purine-2,6-diamine, 2-({6-[(2-amino-5-chlorobenzyl)amino]-9-methyl-9H-purin-2-yl}amino)-3-methyl-butan-1-ol, 2-({6-[(2-amino-5-chlorobenzyl)amino]-9-ethyl-9H- purin-2-yl}amino)-3-methyl-butan-1-ol, 2-({6-[(2-amino-5-chlorobenzyl)amino]-9-isopropyl-9H-purin-2-yl}amino)-3-methyl-butan-1-ol, 2-({6-[(2-amino-5-chlorobenzyl)amino]-9-cyclohexyl-9H-purin-2-yl}amino)-3-methyl-butan-1-ol, 2-({6-[(2-amino-5-chlorobenzyl)amino]-9-benzyl-9H-purin-2-yl}amino)-3-methyl-butan-1-ol, $N^6$-(2-amino-5-chlorobenzyl)-$N^2$-(4-aminocyclohexyl)-9-methyl-9H-purine-2,6-diamine, $N^6$-(2-amino-5-chlorobenzyl)-$N^2$-(4-aminocyclohexyl)-9-ethyl-9H-purine-2,6-diamine, $N^6$-(2-amino-5-chlorobenzyl)-$N^2$-(4-aminocyclohexyl)-9-isopropyl-9H-purine-2,6-diamine, $N^6$-(2-amino-5-chlorobenzyl)-$N^2$-(4-aminocyclohexyl)-9-cyclohexyl-9H-purine-2,6-diamine, $N^6$-(2-amino-5-chlorobenzyl)-$N^2$-(4-aminocyclohexyl)-9-benzyl-9H-purine-2,6-diamine, 1-({6-[(2-amino-5-chlorobenzyl)amino]-9-methyl-9H-purin-2-yl}amino)-2-methyl-propan-2-ol, 1-({6-[(2-amino-5-chlorobenzyl)amino]-9-ethyl-9H-purin-2-yl}amino)-2-methyl-propan-2-ol, 1-({6-[(2-amino-5-chlorobenzyl)amino]-9-isopropyl-9H-purin-2-yl}amino)-2-methyl-propan-2-ol, 3-({6-[(2-amino-5-chlorobenzyl)amino]-9-methyl-9H-purin-2-yl}amino)-2-methyl-butan-2-ol, 3-({6-[(2-amino-5-chlorobenzyl)amino]-9-ethyl-9H-purin-2-yl}amino)-2-methyl-butan-2-ol, 3-({6-[(2-amino-5-chlorobenzyl)amino]-9-isopropyl-9H-purin-2-yl}amino)-2-methyl-butan-2-ol, 3-({6-[(2-amino-5-chlorobenzyl)amino]-9-cyclohexyl-9H-purin-2-yl}amino)-2-methyl-butan-2-ol, 3-({6-[(2-amino-5-chlorobenzyl)amino]-9-benzyl-9H-purin-2-yl}amino)-2-methyl-butan-2-ol, 4-({6-[(2-amino-5-chlorobenzyl)amino]-9-methyl-9H-purin-2-yl}amino)-2-methyl-butan-2-ol, 4-({6-[(2-amino-5-chlorobenzyl)amino]-9-ethyl-9H-purin-2-yl}amino)-2-methyl-butan-2-ol, 4-({6-[(2-amino-5-chlorobenzyl)amino]-9-isopropyl-9H-purin-2-yl}amino)-2-methyl-butan-2-ol, 4-({6-[(2-amino-5-chlorobenzyl)amino]-9-cyclohexyl-9H-purin-2-yl}amino)-2-methyl-butan-2-ol, 4-({6-[(2-amino-5-chlorobenzyl)amino]-9-benzyl-9H-purin-2-yl}amino)-2-methyl-butan-2-ol, 4-({6-[(2-amino-5-chlorobenzyl)amino]-9-methyl-9H-purin-2-yl}amino)-2-methyl-pentan-2-ol, 4-({6-[(2-amino-5-chlorobenzyl)amino]-9-ethyl-9H-purin-2-yl}amino)-2-methyl-pentan-2-ol, 4-({6-[(2-amino-5-chlorobenzyl)amino]-9-isopropyl-9H-purin-2-yl}amino)-2-methyl-pentan-2-ol, 4-({6-[(2-amino-5-chlorobenzyl)amino]-9-cyclohexyl-9H-purin-2-yl}amino)-2-methyl-pentan-2-ol, 4-({6-[(2-amino-5-chlorobenzyl)amino]-9-benzyl-9H-purin-2-yl}amino)-2-methyl-pentan-2-ol, 1-({6-[(2-amino-5-chlorobenzyl)amino]-9-methyl-9H-purin-2-yl}amino)propan-2-ol, 1-({6-[(2-amino-5-chlorobenzyl)amino]-9-ethyl-9H-purin-2-yl}amino)propan-2-ol, 1-({6-[(2-amino-5-chlorobenzyl)amino]-9-isopropyl-9H-purin-2-yl}amino)propan-2-ol, 1-({6-[(2-amino-5-chlorobenzyl)amino]-9-cyclohexyl-9H-purin-2-yl}amino)propan-2-ol, 1-({6-[(2-amino-5-chlorobenzyl)amino]-9-benzyl-9H-purin-2-yl}amino)propan-2-ol, 4-({6-[(2-amino-5-chlorobenzyl)amino]-9-methyl-9H-purin-2-yl}amino)-2,3-dimethyl-butan-2-ol, 4-({6-[(2-amino-5-chlorobenzyl)amino]-9-ethyl-9H-purin-2-yl}amino)-2,3-dimethyl-butan-2-ol, 4-({6-[(2-amino-5-chlorobenzyl)amino]-9-isopropyl-9H-purin-2-yl}amino)-2,3-dimethyl-butan-2-ol, 4-({6-[(2-amino-5-chlorobenzyl)amino]-9-cyclohexyl-9H-purin-2-yl}amino)-2,3-dimethyl-butan-2-ol, 4-({6-[(2-amino-5-chlorobenzyl)amino]-9-benzyl-9H-purin-2-yl}amino)-2,3-dimethyl-butan-2-ol, 3-({6-[(2-amino-5-chlorobenzyl)amino]-9-methyl-9H-purin-2-yl}amino)-2-methyl-pentan-2-ol, 3-({6-[(2-amino-5-chlorobenzyl)amino]-9-ethyl-9H-purin-2-yl}amino)-2-methyl-pentan-2-ol, 3-({6-[(2-amino-5-chlorobenzyl)amino]-9-isopropyl-9H-purin-2-yl}amino)-2-methyl-pentan-2-ol, 3-({6-[(2-amino-5-chlorobenzyl)amino]-9-cyclohexyl-9H-purin-2-yl}amino)-2-methyl-pentan-2-ol, 3-({6-[(2-amino-5-chlorobenzyl)amino]-9-benzyl-9H-purin-2-yl}amino)-2-methyl-pentan-2-ol, 3-({6-[(2-amino-5-chlorobenzyl)amino]-9-methyl-9H-purin-2-yl]amino}pentan-2-ol, 3-({6-[(2-amino-5-chlorobenzyl)amino]-9-ethyl-9H-purin-2-yl]amino}pentan-2-ol, 3-({6-[(2-amino-5-chlorobenzyl)amino]-9-isopropyl-9H-purin-2-yl]amino}pentan-2-ol, 3-({6-[(2-amino-5-chlorobenzyl)amino]-9-cyclohexyl-9H-purin-2-yl]amino}pentan-2-ol, 3-({6-[(2-amino-5-chlorobenzyl)amino]-9-benzyl-9H-purin-2-yl]amino}pentan-2-ol, 1-({6-[(2-amino-5-chlorobenzyl)amino]-9-cyclopropyl-9H-purin-2-yl}amino)-2-methyl-propan-2-ol, 1-({6-[(2-amino-5-chlorobenzyl)amino]-9-cyclohexyl-9H-purin-2-yl}amino)-2-methyl-propan-2-ol, 1-({6-[(2-amino-5-chlorobenzyl)amino]-9-benzyl-9H-purin-2-yl}amino)-2-methyl-propan-2-ol, 2-({6-[(2-amino-3-chlorobenzyl)amino]-9-methyl-9H-purin-2-yl}amino)butan-1-ol, 2-({6-[(2-amino-3-chlorobenzyl)amino]-9-ethyl-9H-purin-2-yl}amino)butan-1-ol, 2-({6-[(2-amino-3-chlorobenzyl)amino]-9-cyclohexyl-9H-purin-2-yl}amino)butan-1-ol, 2-({6-[(2-amino-3-chlorobenzyl)amino]-9-benzyl-9H-purin-2-yl}amino)butan-1-ol, $N^6$-(2-amino-3-chlorobenzyl)-$N^2$-(2-aminopropyl)-9-methyl-9H-purine-2,6-diamine, $N^6$-(2-amino-3-chlorobenzyl)-$N^2$-(2-aminopropyl)-9-ethyl-9H-purine-2,6-diamine, $N^6$-(2-amino-3-chlorobenzyl)-$N^2$-(2-aminopropyl)-9-isopropyl-9H-purine-2,6-diamine, $N^6$-(2-amino-3-chlorobenzyl)-$N^2$-(2-aminopropyl)-9-cyclohexyl-9H-purine-2,6-diamine, $N^6$-(2-amino-3-chlorobenzyl)-$N^2$-(2-aminopropyl)-9-benzyl-9H-purine-2,6-diamine, 2-({6-[(2-amino-3-chlorobenzyl)amino]-9-methyl-9H-purin-2-yl}amino)-3-methyl-butan-1-ol, 2-({6-[(2-amino-3-chlorobenzyl)amino]-9-ethyl-9H-purin-2-yl}amino)-3-methyl-butan-1-ol, 2-({6-[(2-amino-3-chlorobenzyl)amino]-9-isopropyl-9H-purin-2-yl}amino)-3-methyl-butan-1-ol, 2-({6-[(2-amino-3-chlorobenzyl)amino]-9-cyclohexyl-9H-purin-2-yl}amino)-3-methyl-butan-1-ol, 2-({6-[(2-amino-3-chlorobenzyl)amino]-9-benzyl-9H-purin-2-yl}amino)-3-methyl-butan-1-ol, $N^6$-(2-amino-3-chlorobenzyl)-$N^2$-(4-aminocyclohexyl)-9-methyl-9H-purine-2,6-diamine, $N^6$-(2-amino-3-chlorobenzyl)-$N^2$-(4-aminocyclohexyl)-9-ethyl-9H-purine-2,6-diamine, $N^6$-(2-amino-3-chlorobenzyl)-$N^2$-(4-aminocyclohexyl)-9-isopropyl-9H-purine-2,6-diamine, $N^6$-(2-amino-3-chlorobenzyl)-$N^2$-(4-aminocyclohexyl)-9-methyl-9H-purine-2,6-diamine, $N^6$-(2-amino-3-chlorobenzyl)-$N^2$-(4-aminocyclohexyl)-9-cyclohexyl-9H-purine-2,6-diamine, $N^6$-(2-amino-3-chlorobenzyl)-$N^2$-(4-aminocyclohexyl)-9-benzyl-9H-purine-2,6-diamine, 1-({6-[(2-amino-3-chlorobenzyl)amino]-9-methyl-9H-purin-2-yl}amino)propan-2-ol, 1-({6-[(2-amino-3-chlorobenzyl)amino]-9-ethyl-9H-purin-2-yl}amino)propan-2-ol, 1-({6-[(2-amino-3-chlorobenzyl)amino]-9-isopropyl-9H-purin-2-yl}amino)propan-2-ol, 1-({6-[(2-amino-3-chlorobenzyl)amino]-9-cyclohexyl-9H-purin-2-yl}amino)propan-2-ol, 1-({6-[(2-amino-3-chlorobenzyl)amino]-9-benzyl-9H-purin-2-yl}amino)propan-2-ol, 1-({6-[(2-amino-3-chlorobenzyl)amino]-9-methyl-9H-purin-2-yl}amino)-2-methyl-propan-2-ol, 1-({6-[(2-amino-3-chlorobenzyl)amino]-9-ethyl-9H-purin-2-yl}amino)-2-methyl-propan-2-ol, 1-({6-[(2-amino-3-chlorobenzyl)amino]-9-isopropyl-9H-purin-2-yl}amino)-2-methyl-propan-2-ol, 3-({6-[(2-amino-3-chlorobenzyl)amino]-9-methyl-9H-purin-2-yl}amino)-2-methyl-butan-2-ol, 3-({6-[(2-amino-3-chlorobenzyl)amino]-9-ethyl-9H-purin-2-yl}amino)-2-methyl-butan-2-ol, 3-({6-[(2-amino-3-chlorobenzyl)amino]-9-isopropyl-9H-purin-2-yl}amino)-2-methyl-butan-2-ol, 3-({6-[(2-amino-3-chlorobenzyl)

amino]-9-cyclohexyl-9H-purin-2-yl}amino)-2-methyl-butan-2-ol, 3-({6-[(2-amino-3-chlorobenzyl)amino]-9-benzyl-9H-purin-2-yl}amino)-2-methyl-butan-2-ol, 4-({6-[(2-amino-3-chlorobenzyl)amino]-9-methyl-9H-purin-2-yl}amino)-2-methyl-butan-2-ol, 4-({6-[(2-amino-3-chlorobenzyl)amino]-9-ethyl-9H-purin-2-yl}amino)-2-methyl-butan-2-ol, 4-({6-[(2-amino-3-chlorobenzyl)amino]-9-isopropyl-9H-purin-2-yl}amino)-2-methyl-butan-2-ol, 4-({6-[(2-amino-3-chlorobenzyl)amino]-9-cyclohexyl-9H-purin-2-yl}amino)-2-methyl-butan-2-ol, 4-({6-[(2-amino-3-chlorobenzyl)amino]-9-benzyl-9H-purin-2-yl}amino)-2-methyl-butan-2-ol, 4-({6-[(2-amino-3-chlorobenzyl)amino]-9-methyl-9H-purin-2-yl}amino)-2-methyl-pentan-2-ol, 4-({6-[(2-amino-3-chlorobenzyl)amino]-9-ethyl-9H-purin-2-yl}amino)-2-methyl-pentan-2-ol, 4-({6-[(2-amino-3-chlorobenzyl)amino]-9-isopropyl-9H-purin-2-yl}amino)-2-methyl-pentan-2-ol, 4-({6-[(2-amino-3-chlorobenzyl)amino]-9-cyclohexyl-9H-purin-2-yl}amino)-2-methyl-pentan-2-ol, 4-({6-[(2-amino-3-chlorobenzyl)amino]-9-benzyl-9H-purin-2-yl}amino)-2-methyl-pentan-2-ol, 4-({6-[(2-amino-3-chlorobenzyl)amino]-9-methyl-9H-purin-2-yl}amino)-2,3-dimethyl-butan-2-ol, 4-({6-[(2-amino-3-chlorobenzyl)amino]-9-ethyl-9H-purin-2-yl}amino)-2,3-dimethyl-butan-2-ol, 4-({6-[(2-amino-3-chlorobenzyl)amino]-9-isopropyl-9H-purin-2-yl}amino)-2,3-dimethyl-butan-2-ol, 4-({6-[(2-amino-3-chlorobenzyl)amino]-9-cyclohexyl-9H-purin-2-yl}amino)-2,3-dimethyl-butan-2-ol, 4-({6-[(2-amino-3-chlorobenzyl)amino]-9-benzyl-9H-purin-2-yl}amino)-2,3-dimethyl-butan-2-ol, 3-({6-[(2-amino-3-chlorobenzyl)amino]-9-methyl-9H-purin-2-yl}amino)-2-methyl-pentan-2-ol, 3-({6-[(2-amino-3-chlorobenzyl)amino]-9-ethyl-9H-purin-2-yl}amino)-2-methyl-pentan-2-ol, 3-({6-[(2-amino-3-chlorobenzyl)amino]-9-isopropyl-9H-purin-2-yl}amino)-2-methyl-pentan-2-ol, 3-({6-[(2-amino-3-chlorobenzyl)amino]-9-cyclohexyl-9H-purin-2-yl}amino)-2-methyl-pentan-2-ol, 3-({6-[(2-amino-3-chlorobenzyl)amino]-9-benzyl-9H-purin-2-yl}amino)-2-methyl-pentan-2-ol, 3-({6-[(2-amino-3-chlorobenzyl)amino]-9-methyl-9H-purin-2-yl]amino}pentan-2-ol, 3-({6-[(2-amino-3-chlorobenzyl)amino]-9-ethyl-9H-purin-2-yl]amino}pentan-2-ol, 3-({6-[(2-amino-3-chlorobenzyl)amino]-9-isopropyl-9H-purin-2-yl]amino}pentan-2-ol, 3-({6-[(2-amino-3-chlorobenzyl)amino]-9-cyclohexyl-9H-purin-2-yl]amino}pentan-2-ol, 3-({6-[(2-amino-3-chlorobenzyl)amino]-9-benzyl-9H-purin-2-yl]amino}pentan-2-ol, 1-({6-[(2-amino-3-chlorobenzyl)amino]-9-cyclohexyl-9H-purin-2-yl}amino)-2-methyl-propan-2-ol, 1-({6-[(2-amino-3-chlorobenzyl)amino]-9-benzyl-9H-purin-2-yl}amino)-2-methyl-propan-2-ol, 2-({6-[(2-amino-5-fluorobenzyl)amino]-9-methyl-9H-purin-2-yl}amino)butan-1-ol, 2-({6-[(2-amino-5-fluorobenzyl)amino]-9-ethyl-9H-purin-2-yl}amino)butan-1-ol, 2-({6-[(2-amino-5-fluorobenzyl)amino]-9-isopropyl-9H-purin-2-yl}amino)butan-1-ol, 2-({6-[(2-amino-5-fluorobenzyl)amino]-9-cyclopropyl-9H-purin-2-yl}amino)butan-1-ol, 2-({6-[(2-amino-5-fluorobenzyl)amino]-9-cyclohexyl-9H-purin-2-yl}amino)butan-1-ol, 2-({6-[(2-amino-5-fluorobenzyl)amino]-9-benzyl-9H-purin-2-yl}amino)butan-1-ol, $N^6$-(2-amino-5-fluorobenzyl)-$N^2$-(2-aminopropyl)-9-methyl-9H-purine-2,6-diamine, $N^6$-(2-amino-5-fluorobenzyl)-$N^2$-(2-aminopropyl)-9-ethyl-9H-purine-2,6-diamine, $N^6$-(2-amino-5-fluorobenzyl)-$N^2$-(2-aminopropyl)-9-isopropyl-9H-purine-2,6-diamine, $N^6$-(2-amino-5-fluorobenzyl)-$N^2$-(2-aminopropyl)-9-cyclohexyl-9H-purine-2,6-diamine, $N^6$-(2-amino-5-fluorobenzyl)-$N^2$-(2-aminopropyl)-9-benzyl-9H-purine-2,6-diamine, 1-({6-[(2-amino-5-fluorobenzyl)amino]-9-methyl-9H-purin-2-yl}amino)propan-2-ol, 1-({6-[(2-amino-5-fluorobenzyl)amino]-9-ethyl-9H-purin-2-yl}amino)propan-2-ol, 1-({6-[(2-amino-5-fluorobenzyl)amino]-9-isopropyl-9H-purin-2-yl}amino)propan-2-ol, 1-({6-[(2-amino-5-fluorobenzyl)amino]-9-cyclohexyl-9H-purin-2-yl}amino)propan-2-ol, 1-({6-[(2-amino-5-fluorobenzyl)amino]-9-benzyl-9H-purin-2-yl}amino)propan-2-ol, 2-({6-[(2-amino-5-fluorobenzyl)amino]-9-methyl-9H-purin-2-yl}amino)-3-methyl-butan-1-ol, 2-({6-[(2-amino-5-fluorobenzyl)amino]-9-ethyl-9H-purin-2-yl}amino)-3-methyl-butan-1-ol, 2-({6-[(2-amino-5-fluorobenzyl)amino]-9-isopropyl-9H-purin-2-yl}amino)-3-methyl-butan-1-ol, 2-({6-[(2-amino-5-fluorobenzyl)amino]-9-cyclohexyl-9H-purin-2-yl}amino)-3-methyl-butan-1-ol, 2-({6-[(2-amino-5-fluorobenzyl)amino]-9-benzyl-9H-purin-2-yl}amino)-3-methyl-butan-1-ol, $N^6$-(2-amino-5-fluorobenzyl)-$N^2$-(4-aminocyclohexyl)-9-methyl-9H-purine-2,6-diamine, $N^6$-(2-amino-5-fluorobenzyl)-$N^2$-(4-aminocyclohexyl)-9-ethyl-9H-purine-2,6-diamine, $N^6$-(2-amino-5-fluorobenzyl)-$N^2$-(4-aminocyclohexyl)-9-isopropyl-9H-purine-2,6-diamine, $N^6$-(2-amino-5-fluorobenzyl)-$N^2$-(4-aminocyclohexyl)-9-methyl-9H-purine-2,6-diamine, $N^6$-(2-amino-5-fluorobenzyl)-$N^2$-(4-aminocyclohexyl)-9-cyclohexyl-9H-purine-2,6-diamine, $N^6$-(2-amino-5-fluorobenzyl)-$N^2$-(4-aminocyclohexyl)-9-benzyl-9H-purine-2,6-diamine, 1-({6-[(2-amino-5-fluorobenzyl)amino]-9-methyl-9H-purin-2-yl}amino)-2-methyl-propan-2-ol, 1-({6-[(2-amino-5-fluorobenzyl)amino]-9-ethyl-9H-purin-2-yl}amino)-2-methyl-propan-2-ol, 1-({6-[(2-amino-5-fluorobenzyl)amino]-9-isopropyl-9H-purin-2-yl}amino)-2-methyl-propan-2-ol, 1-({6-[(2-amino-5-fluorobenzyl)amino]-9-(3-pentyl)-9H-purin-2-yl}amino)-2-methyl-propan-2-ol, 3-({6-[(2-amino-5-fluorobenzyl)amino]-9-methyl-9H-purin-2-yl}amino)-2-methyl-butan-2-ol, 3-({6-[(2-amino-5-fluorobenzyl)amino]-9-ethyl-9H-purin-2-yl}amino)-2-methyl-butan-2-ol, 3-({6-[(2-amino-5-fluorobenzyl)amino]-9-isopropyl-9H-purin-2-yl}amino)-2-methyl-butan-2-ol, 3-({6-[(2-amino-5-fluorobenzyl)amino]-9-cyclohexyl-9H-purin-2-yl}amino)-2-methyl-butan-2-ol, 3-({6-[(2-amino-5-fluorobenzyl)amino]-9-benzyl-9H-purin-2-yl}amino)-2-methyl-butan-2-ol, 4-({6-[(2-amino-5-fluorobenzyl)amino]-9-methyl-9H-purin-2-yl}amino)-2-methyl-butan-2-ol, 4-({6-[(2-amino-5-fluorobenzyl)amino]-9-ethyl-9H-purin-2-yl}amino)-2-methyl-butan-2-ol, 4-({6-[(2-amino-5-fluorobenzyl)amino]-9-isopropyl-9H-purin-2-yl}amino)-2-methyl-butan-2-ol, 4-({6-[(2-amino-5-fluorobenzyl)amino]-9-cyclohexyl-9H-purin-2-yl}amino)-2-methyl-butan-2-ol, 4-({6-[(2-amino-5-fluorobenzyl)amino]-9-benzyl-9H-purin-2-yl}amino)-2-methyl-butan-2-ol, 4-({6-[(2-amino-5-fluorobenzyl)amino]-9-methyl-9H-purin-2-yl}amino)-2-methyl-pentan-2-ol, 4-({6-[(2-amino-5-fluorobenzyl)amino]-9-ethyl-9H-purin-2-yl}amino)-2-methyl-pentan-2-ol, 4-({6-[(2-amino-5-fluorobenzyl)amino]-9-isopropyl-9H-purin-2-yl}amino)-2-methyl-pentan-2-ol, 4-({6-[(2-amino-5-fluorobenzyl)amino]-9-cyclohexyl-9H-purin-2-yl}amino)-2-methyl-pentan-2-ol, 4-({6-[(2-amino-5-fluorobenzyl)amino]-9-benzyl-9H-purin-2-yl}amino)-2-methyl-pentan-2-ol, 4-({6-[(2-amino-5-fluorobenzyl)amino]-9-methyl-9H-purin-2-yl}amino)-2,3-dimethyl-butan-2-ol, 4-({6-[(2-amino-5-fluorobenzyl)amino]-9-ethyl-9H-purin-2-yl}amino)-2,3-dimethyl-butan-2-ol, 4-({6-[(2-amino-5-fluorobenzyl)amino]-9-isopropyl-9H-purin-2-yl}amino)-2,3-dimethyl-butan-2-ol, 4-({6-[(2-amino-5-fluorobenzyl)amino]-9-cyclohexyl-9H-purin-2-yl}amino)-2,3-dimethyl-butan-2-ol, 4-({6-[(2-amino-5-fluorobenzyl)amino]-9-benzyl-9H-purin-2-yl}amino)-2,3-dimethyl-butan-2-ol, 3-({6-[(2-amino-5-fluorobenzyl)amino]-9-methyl-9H-purin-2-yl}amino)-2-methyl-pentan-2-ol, 3-({6-

[(2-amino-5-fluorobenzyl)amino]-9-ethyl-9H-purin-2-yl}amino)-2-methyl-pentan-2-ol, 3-({6-[(2-amino-5-fluorobenzyl)amino]-9-isopropyl-9H-purin-2-yl}amino)-2-methyl-pentan-2-ol, 3-({6-[(2-amino-5-fluorobenzyl)amino]-9-cyclohexyl-9H-purin-2-yl}amino)-2-methyl-pentan-2-ol, 3-({6-[(2-amino-5-fluorobenzyl)amino]-9-benzyl-9H-purin-2-yl}amino)-2-methyl-pentan-2-ol, 3-({6-[(2-amino-5-fluorobenzyl)amino]-9-methyl-9H-purin-2-yl]amino}pentan-2-ol, 3-({6-[(2-amino-5-fluorobenzyl)amino]-9-ethyl-9H-purin-2-yl]amino}pentan-2-ol, 3-({6-[(2-amino-5-fluorobenzyl)amino]-9-isopropyl-9H-purin-2-yl}amino pentan-2-ol, 3-({6-[(2-amino-5-fluorobenzyl)amino]-9-cyclohexyl-9H-purin-2-yl]amino}pentan-2-ol, 3-({6-[(2-amino-5-fluorobenzyl)amino]-9-benzyl-9H-purin-2-yl]amino}pentan-2-ol, 1-({6-[(2-amino-5-fluorobenzyl)amino]-9-cyclopropyl-9H-purin-2-yl}amino)-2-methyl-propan-2-ol, 1-({6-[(2-amino-5-fluorobenzyl)amino]-9-cyclohexyl-9H-purin-2-yl}amino)-2-methyl-propan-2-ol, 1-({6-[(2-amino-5-fluorobenzyl)amino]-9-benzyl-9H-purin-2-yl}amino)-2-methyl-propan-2-ol, 2-({6-[(2-amino-5-iodobenzyl)amino]-9-methyl-9H-purin-2-yl}amino)butan-1-ol, 2-({6-[(2-amino-5-iodobenzyl)amino]-9-ethyl-9H-purin-2-yl}amino)butan-1-ol, 2-({6-[(2-amino-5-iodobenzyl)amino]-9-cyclohexyl-9H-purin-2-yl}amino)butan-1-ol, {6-[(2-amino-5-iodobenzyl)amino]-9-benzyl-9H-purin-2-yl}amino)butan-1-ol, $N^6$-(2-amino-5-iodobenzyl)-$N^2$-(2-aminopropyl)-9-methyl-9H-purine-2,6-diamine, $N^6$-(2-amino-5-iodobenzyl)-$N^2$-(2-aminopropyl)-9-ethyl-9H-purine-2,6-diamine, $N^6$-(2-amino-5-iodobenzyl)-$N^2$-(2-aminopropyl)-9-isopropyl-9H-purine-2,6-diamine, $N^6$-(2-amino-5-iodobenzyl)-$N^2$-(2-aminopropyl)-9-cyclohexyl-9H-purine-2,6-diamine, $N^6$-(2-amino-5-iodobenzyl)-$N^2$-(2-aminopropyl)-9-benzyl-9H-purine-2,6-diamine, 2-({6-[(2-amino-5-iodobenzyl)amino]-9-methyl-9H-purin-2-yl}amino)-3-methyl-butan-1-ol, 2-({6-[(2-amino-5-iodobenzyl)amino]-9-ethyl-9H-purin-2-yl}amino)-3-methyl-butan-1-ol, 2-({6-[(2-amino-5-iodobenzyl)amino]-9-isopropyl-9H-purin-2-yl}amino)-3-methyl-butan-1-ol, 2-({6-[(2-amino-5-iodobenzyl)amino]-9-cyclohexyl-9H-purin-2-yl}amino)-3-methyl-butan-1-ol, 2-({6-[(2-amino-5-iodobenzyl)amino]-9-benzyl-9H-purin-2-yl}amino)-3-methyl-butan-1-ol, 1-({6-[(2-amino-5-iodobenzyl)amino]-9-methyl-9H-purin-2-yl}amino)propan-2-ol, 1-({6-[(2-amino-5-iodobenzyl)amino]-9-ethyl-9H-purin-2-yl}amino)propan-2-ol, 1-({6-[(2-amino-5-iodobenzyl)amino]-9-isopropyl-9H-purin-2-yl}amino)propan-2-ol, 1-({6-[(2-amino-5-iodobenzyl)amino]-9-cyclohexyl-9H-purin-2-yl}amino)propan-2-ol, 1-({6-[(2-amino-5-iodobenzyl)amino]-9-benzyl-9H-purin-2-yl}amino)propan-2-ol, $N^6$-(2-amino-5-iodobenzyl)-$N^2$-(4-aminocyclohexyl)-9-methyl-9H-purine-2,6-diamine, $N^6$-(2-amino-5-iodobenzyl)-$N^2$-(4-aminocyclohexyl)-9-ethyl-9H-purine-2,6-diamine, $N^6$-(2-amino-5-iodobenzyl)-$N^2$-(4-aminocyclohexyl)-9-isopropyl-9H-purine-2,6-diamine, $N^6$-(2-amino-5-iodobenzyl)-$N^2$-(4-aminocyclohexyl)-9-cyclohexyl-9H-purine-2,6-diamine, $N^6$-(2-amino-5-iodobenzyl)-$N^2$-(4-aminocyclohexyl)-9-benzyl-9H-purine-2,6-diamine, 1-({6-[(2-amino-5-iodobenzyl)amino]-9-methyl-9H-purin-2-yl}amino)-2-methyl-propan-2-ol, 1-({6-[(2-amino-5-iodobenzyl)amino]-9-ethyl-9H-purin-2-yl}amino)-2-methyl-propan-2-ol, 1-({6-[(2-amino-5-iodobenzyl)amino]-9-isopropyl-9H-purin-2-yl}amino)-2-methyl-propan-2-ol, 3-({6-[(2-amino-5-iodobenzyl)amino]-9-methyl-9H-purin-2-yl}amino)-2-methyl-butan-2-ol, 3-({6-[(2-amino-5-iodobenzyl)amino]-9-ethyl-9H-purin-2-yl}amino)-2-methyl-butan-2-ol, 3-({6-[(2-amino-5-iodobenzyl)amino]-9-isopropyl-9H-purin-2-yl}amino)-2-methyl-butan-2-ol, 3-({6-[(2-amino-5-iodobenzyl)amino]-9-cyclohexyl-9H-purin-2-yl}amino)-2-methyl-butan-2-ol, 3-({6-[(2-amino-5-iodobenzyl)amino]-9-benzyl-9H-purin-2-yl}amino)-2-methyl-butan-2-ol, 4-({6-[(2-amino-5-iodobenzyl)amino]-9-methyl-9H-purin-2-yl}amino)-2-methyl-butan-2-ol, 4-({6-[(2-amino-5-iodobenzyl)amino]-9-ethyl-9H-purin-2-yl}amino)-2-methyl-butan-2-ol, 4-({6-[(2-amino-5-iodobenzyl)amino]-9-isopropyl-9H-purin-2-yl}amino)-2-methyl-butan-2-ol, 4-({6-[(2-amino-5-iodobenzyl)amino]-9-cyclohexyl-9H-purin-2-yl}amino)-2-methyl-butan-2-ol, 4-({6-[(2-amino-5-iodobenzyl)amino]-9-benzyl-9H-purin-2-yl}amino)-2-methyl-butan-2-ol, 4-({6-[(2-amino-5-iodobenzyl)amino]-9-methyl-9H-purin-2-yl}amino)-2-methyl-pentan-2-ol, 4-({6-[(2-amino-5-iodobenzyl)amino]-9-ethyl-9H-purin-2-yl}amino)-2-methyl-pentan-2-ol, 4-({6-[(2-amino-5-iodobenzyl)amino]-9-isopropyl-9H-purin-2-yl}amino)-2-methyl-pentan-2-ol, 4-({6-[(2-amino-5-iodobenzyl)amino]-9-cyclohexyl-9H-purin-2-yl}amino)-2-methyl-pentan-2-ol, 4-({6-[(2-amino-5-iodobenzyl)amino]-9-benzyl-9H-purin-2-yl}amino)-2-methyl-pentan-2-ol, 4-({6-[(2-amino-5-iodobenzyl)amino]-9-methyl-9H-purin-2-yl}amino)-2,3-dimethyl-butan-2-ol, 4-({6-[(2-amino-5-iodobenzyl)amino]-9-ethyl-9H-purin-2-yl}amino)-2,3-dimethyl-butan-2-ol, 4-({6-[(2-amino-5-iodobenzyl)amino]-9-isopropyl-9H-purin-2-yl}amino)-2,3-dimethyl-butan-2-ol, 4-({6-[(2-amino-5-iodobenzyl)amino]-9-cyclohexyl-9H-purin-2-yl}amino)-2,3-dimethyl-butan-2-ol, 4-({6-[(2-amino-5-iodobenzyl)amino]-9-benzyl-9H-purin-2-yl}amino)-2,3-dimethyl-butan-2-ol, 3-({6-[(2-amino-5-iodobenzyl)amino]-9-methyl-9H-purin-2-yl}amino)-2-methyl-pentan-2-ol, 3-({6-[(2-amino-5-iodobenzyl)amino]-9-ethyl-9H-purin-2-yl}amino)-2-methyl-pentan-2-ol, 3-({6-[(2-amino-5-iodobenzyl)amino]-9-isopropyl-9H-purin-2-yl}amino)-2-methyl-pentan-2-ol, 3-({6-[(2-amino-5-iodobenzyl)amino]-9-cyclohexyl-9H-purin-2-yl}amino)-2-methyl-pentan-2-ol, 3-({6-[(2-amino-5-iodobenzyl)amino]-9-benzyl-9H-purin-2-yl}amino)-2-methyl-pentan-2-ol, 3-({6-[(2-amino-5-iodobenzyl)amino]-9-methyl-9H-purin-2-yl]amino}pentan-2-ol, 3-({6-[(2-amino-5-iodobenzyl)amino]-9-ethyl-9H-purin-2-yl]amino}pentan-2-ol, 3-({6-[(2-amino-5-iodobenzyl)amino]-9-isopropyl-9H-purin-2-yl]amino}pentan-2-ol, 3-({6-[(2-amino-5-iodobenzyl)amino]-9-cyclohexyl-9H-purin-2-yl]amino}pentan-2-ol, 3-({6-[(2-amino-5-iodobenzyl)amino]-9-benzyl-9H-purin-2-yl]amino}pentan-2-ol, 1-({6-[(2-amino-5-iodobenzyl)amino]-9-cyclopropyl-9H-purin-2-yl}amino)-2-methyl-propan-2-ol, 1-({6-[(2-amino-5-iodobenzyl)amino]-9-cyclohexyl-9H-purin-2-yl}amino)-2-methyl-propan-2-ol, 1-({6-[(2-amino-5-iodobenzyl)amino]-9-benzyl-9H-purin-2-yl}amino)-2-methyl-propan-2-ol, 2-({6-(2,3-diaminobenzyl)amino]-9-methyl-9H-purin-2-yl}amino)butan-1-ol, 2-({6-(2,3-diaminobenzyl)amino]-9-ethyl-9H-purin-2-yl}amino)butan-1-ol, 2-({6-(2,3-diaminobenzyl)amino]-9-cyclohexyl-9H-purin-2-yl}amino)butan-1-ol, 2-({6-(2,3-diaminobenzyl)amino]-9-benzyl-9H-purin-2-yl}amino)butan-1-ol, $N^6$-(2,3-diaminobenzyl)amino]-$N^2$-(2-aminopropyl)-9-methyl-9H-purine-2,6-diamine, $N^6$-(2,3-diaminobenzyl)amino]-$N^2$-(2-aminopropyl)-9-ethyl-9H-purine-2,6-diamine, $N^6$-(2,3-diaminobenzyl)amino]-$N^2$-(2-aminopropyl)-9-isopropyl-9H-purine-2,6-diamine, $N^6$-(2,3-diaminobenzyl)amino]-$N^2$-(2-aminopropyl)-9-cyclohexyl-9H-purine-2,6-diamine, $N^6$-(2,3-diaminobenzyl)amino]-$N^2$-(2-aminopropyl)-9-benzyl-9H-purine-2,6-diamine, 2-({6-(2,3-diaminobenzyl)amino]-9-methyl-9H-purin-2-yl}amino)-3-methyl-butan-1-ol, 2-({6-(2,3-diaminobenzyl)amino]-9-ethyl-9H-purin-2-yl}amino)-3-methyl-butan-1-ol, 2-({6-(2,3-diaminobenzyl)amino]-9-isopropyl-9H-purin-2-yl}amino)-3-methyl-butan- 1-ol, 2-({6-(2,3-diaminobenzyl)amino]-9-cyclohexyl-9H-purin-2-yl}amino)-3-methyl-butan-1-ol, 2-({6-(2,3-diaminobenzyl)amino]-9-benzyl-9H-purin-2-yl}amino)-3-methyl-butan-1-ol, $N^6$-(2,3-diaminobenzyl)amino]-$N^2$-(4-aminocyclohexyl)-9-methyl-9H-purine-2,6-diamine, $N^6$-(2,3-diaminobenzyl)amino]-$N^2$-(4-aminocyclohexyl)-9-ethyl-9H-purine-2,6-diamine, $N^6$-(2,3-diaminobenzyl)amino]-$N^2$-(4-aminocyclohexyl)-9-isopropyl-9H-purine-2,6-diamine, $N^6$-(2,3-diaminobenzyl)amino]-$N^2$-(4-aminocyclohexyl)-9-cyclohexyl-9H-purine-2,6-diamine, $N^6$-(2,3-diaminobenzyl)amino]-$N^2$-(4-aminocyclohexyl)-9-benzyl-9H-purine-2,6-diamine, 1-({6-(2,3-diaminobenzyl)amino]-9-methyl-9H-purin-2-yl}amino)-2-methyl-propan-2-ol, 1-({6-(2,3-diaminobenzyl)amino]-9-ethyl-9H-purin-2-yl}amino)-2-methyl-propan-2-ol, 1-({6-(2,3-diaminobenzyl)amino]-9-isopropyl-9H-purin-2-yl}amino)-2-methyl-propan-2-ol, 3-({diaminobenzyl)amino]-9-methyl-9H-purin-2-yl}amino)-2-methyl-butan-2-ol, 3-({6-(2,3-diaminobenzyl)amino]-9-ethyl-9H-purin-2-yl}amino)-2-methyl-butan-2-ol, 3-({6-(2,3-diaminobenzyl)amino]-9-isopropyl-9H-purin-2-yl}amino)-2-methyl-butan-2-ol, 3-({6-(2,3-diaminobenzyl)amino]-9-cyclohexyl-9H-purin-2-yl}amino)-2-methyl-butan-2-ol, 3-({6-(2,3-diaminobenzyl)amino]-9-benzyl-9H-purin-2-yl}amino)-2-methyl-butan-2-ol, 4-({6-(2,3-diaminobenzyl)amino]-9-methyl-9H-purin-2-yl}amino)-2-methyl-butan-2-ol, 4-({6-(2,3-diaminobenzyl)amino]-9-ethyl-9H-purin-2-yl}amino)-2-methyl-butan-2-ol, 4-({6-(2,3-diaminobenzyl)amino]-9-isopropyl-9H-purin-2-yl}amino)-2-methyl-butan-2-ol, 4-({6-(2,3-diaminobenzyl)amino]-9-cyclohexyl-9H-purin-2-yl}amino)-2-methyl-butan-2-ol, 4-({6-(2,3-diaminobenzyl)amino]-9-benzyl-9H-purin-2-yl}amino)-2-methyl-butan-2-ol, 4-({6-(2,3-diaminobenzyl)amino]-9-methyl-9H-purin-2-yl}amino)-2-methyl-pentan-2-ol, 4-({6-(2,3-diaminobenzyl)amino]-9-ethyl-9H-purin-2-yl}amino)-2-methyl-pentan-2-ol, 4-({6-(2,3-diaminobenzyl)amino]-9-isopropyl-9H-purin-2-yl}amino)-2-methyl-pentan-2-ol, 4-({6-(2,3-diaminobenzyl)amino]-9-cyclohexyl-9H-purin-2-yl}amino)-2-methyl-pentan-2-ol, 4-({6-(2,3-diaminobenzyl)amino]-9-benzyl-9H-purin-2-yl}amino)-2-methyl-pentan-2-ol, 4-({6-(2,3-diaminobenzyl)amino]-9-methyl-9H-purin-2-yl}amino)-2,3-dimethyl-butan-2-ol, 4-({6-(2,3-diaminobenzyl)amino]-9-ethyl-9H-purin-2-yl}amino)-2,3-dimethyl-butan-2-ol, 4-({6-(2,3-diaminobenzyl)amino]-9-isopropyl-9H-purin-2-yl}amino)-2,3-dimethyl-butan-2-ol, 4-({6-(2,3-diaminobenzyl)amino]-9-cyclohexyl-9H-purin-2-yl}amino)-2,3-dimethyl-butan-2-ol, 4-{6-(2,3-diaminobenzyl)amino]-9-benzyl-9H-purin-2-yl}amino)-2,3-dimethyl-butan-2-ol, 3-{6-(2,3-diaminobenzyl)amino]-9-methyl-9H-purin-2-yl}amino)-2-methyl-pentan-2-ol, 3-({6-(2,3-diaminobenzyl)amino]-9-ethyl-9H-purin-2-yl}amino)-2-methyl-pentan-2-ol, 3-({6-(2,3-diaminobenzyl)amino]-9-isopropyl-9H-purin-2-yl}amino)-2-methyl-pentan-2-ol, 3-({6-(2,3-diaminobenzyl)amino]-9-cyclohexyl-9H-purin-2-yl}amino)-2-methyl-pentan-2-ol, 3-{6-(2,3-diaminobenzyl)amino]-9-benzyl-9H-purin-2-yl}amino)-2-methyl-pentan-2-ol, 3-({6-(2,3-diaminobenzyl)amino]-9-methyl-9H-purin-2-yl]amino}pentan-2-ol, 3-{6-(2,3-diaminobenzyl)amino]-9-ethyl-9H-purin-2-yl]amino}pentan-2-ol, 3-({6-(2,3-diaminobenzyl)amino]-9-isopropyl-9H-purin-2-yl]amino}pentan-2-ol, 3-({6-(2,3-diaminobenzyl)amino]-9-cyclohexyl-9H-purin-2-yl]amino}pentan-2-ol, 3-({6-(2,3-diaminobenzyl)amino]-9-benzyl-9H-purin-2-yl]amino}pentan-2-ol, 1-({6-(2,3-diaminobenzyl)amino]-9-cyclopropyl-9H-purin-2-yl}amino)-2-methyl-propan-2-ol, 1-({6-(2,3-diaminobenzyl)amino]-9-cyclohexyl-9-H-purin-2-yl}amino)-2-methyl-propan-2-ol, 1-({6-[(2,3-diaminobenzyl)amino]amino]-9-benzyl-9H-purin-2-yl}amino)-2-methyl-propan-2-ol, 1-({6-[(2,3-diaminobenzyl)amino]-9-methyl-9H-purin-2-yl}amino)propan-2-ol, 1-({6-[(2,3-diaminobenzyl)amino]-9-ethyl-9H-purin-2-yl}amino)propan-2-ol, 1-({6-[(2,3-diaminobenzyl)amino]-9-isopropyl-9H-purin-2-yl}amino)propan-2-ol, 1-({6-[(2,3-diaminobenzyl)amino]-9-cyclohexyl-9H-purin-2-yl}amino)propan-2-ol, 1-({6-[(2,3-diaminobenzyl)amino]-9-benzyl-9H-purin-2-yl}amino)propan-2-ol, 2-({6-[(2-amino-5-methylbenzyl)amino]-9-methyl-9H-purin-2-yl}amino)butan-1-ol, 2-({6-[(2-amino-5-methylbenzyl)amino]-9-ethyl-9H-purin-2-yl}amino)butan-1-ol, 2-({6-[(2-amino-5-methylbenzyl)amino]-9-cyclohexyl-9H-purin-2-yl}amino)butan-1-ol, 2-({6-[(2-amino-5-methylbenzyl)amino]-9-benzyl-9H-purin-2-yl}amino)butan-1-ol, $N^6$-(2-amino-5-methylbenzyl)-$N^2$-(2-aminopropyl)-9-methyl-9H-purine-2,6-diamine, $N^6$-(2-amino-5-methylbenzyl)-$N^2$-(2-aminopropyl)-9-ethyl-9H-purine-2,6-diamine, $N^6$-(2-amino-5-methylbenzyl)-$N^2$-(2-aminopropyl)-9-isopropyl-9H-purine-2,6-diamine, $N^6$-(2-amino-5-methylbenzyl)-$N^2$-(2-aminopropyl)-9-cyclohexyl-9H-purine-2,6-diamine, $N^6$-(2-amino-5-methylbenzyl)-$N^2$-(2-aminopropyl)-9-benzyl-9H-purine-2,6-diamine, 2-({6-[(2-amino-5-methylbenzyl)amino]-9-methyl-9H-purin-2-yl}amino)-3-methyl-butan-1-ol, 2-({6-[(2-amino-5-methylbenzyl)amino]-9-ethyl-9H-purin-2-yl}amino)-3-methyl 1-butan-1-ol, 2-({6-[(2-amino-5-methylbenzyl)amino]-9-isopropyl-9H-purin-2-yl}amino)-3-methyl-butan-1-ol, 2-({6-[(2-amino-5-methylbenzyl)amino]-9-cyclohexyl-9H-purin-2-yl}amino)-3-methyl-butan-1-ol, 2-({6-[(2-amino-5-methylbenzyl)amino]-9-benzyl-9H-purin-2-yl}amino)-3-methyl-butan-1-ol, $N^6$-(2-amino-5-methylbenzyl)-$N^2$-(4-aminocyclohexyl)-9-methyl-9H-purine-2,6-diamine, $N^6$-(2-amino-5-methylbenzyl)-$N^2$-(4-aminocyclohexyl)-9-ethyl-9H-purine-2,6-diamine, $N^6$-(2-amino-5-methylbenzyl)-$N^2$-(4-amino cyclohexyl)-9-isopropyl-9H-purine-2,6-diamine, $N^6$-(2-amino-5-methylbenzyl)-$N^2$-(4-aminocyclohexyl)-9-methyl-9H-purine-2,6-diamine, $N^6$-(2-amino-5-methylbenzyl)-$N^2$-(4-aminocyclohexyl)-9-cyclohexyl-9H-purine-2,6-diamine, $N^6$-(2-amino-5-methylbenzyl)-$N^2$-(4-aminocyclohexyl)-9-benzyl-9H-purine-2,6-diamine, 1-({6-[(2-amino-5-methylbenzyl)amino]-9-methyl-9H-purin-2-yl}amino)-2-methyl-propan-2-ol, 1-({6-[(2-amino-5-methylbenzyl)amino]-9-ethyl-9H-purin-2-yl}amino)-2-methyl-propan-2-ol, 1-({6-[(2-amino-5-methylbenzyl)amino]-9-isopropyl-9H-purin-2-yl}amino)-2-methyl 1-propan-2-ol, 1-({6-[(2-amino-5-methylbenzyl)amino]-9-methyl-9H-purin-2-yl}amino)propan-2-ol, 1-({6-[(2-amino-5-methylbenzyl)amino]-9-ethyl-9H-purin-2-yl}amino)propan-2-ol, 1-({6-[(2-amino-5-methylbenzyl)amino]-9-isopropyl-9H-purin-2-yl}amino)propan-2-ol, 1-({6-[(2-amino-5-methylbenzyl)amino]-9-cyclohexyl-9H-purin-2-yl}amino)propan-2-ol, 1-({6-[(2-amino-5-methylbenzyl)amino]-9-benzyl-9H-purin-2-yl}amino)propan-2-ol, 3-({6-[(2-amino-5-methylbenzyl)amino]-9-methyl-9H-purin-2-yl}amino)-2-methyl-butan-2-ol, 3-({6-[(2-amino-5-methylbenzyl)amino]-9-ethyl-9H-purin-2-yl}amino)-2-methyl-butan-2-ol, 3-({6-[(2-amino-5-methylbenzyl)amino]-9-isopropyl-9H-purin-2-yl}amino)-2-methyl-butan-2-ol, 3-({6-[(2-amino-5-methylbenzyl)amino]-9-cyclohexyl-9H-purin-2-yl}amino)-2-methyl-butan-2-ol, 3-({6-[(2-amino-5-methylbenzyl)amino]-9-benzyl-9H-purin-2-yl}amino)-2-methyl-butan-2-ol, 4-({6-[(2-amino-5-methylbenzyl)amino]-9-methyl-9H-purin-2-yl}amino)-2-methyl-butan-2-ol, 4-({6-[(2-amino-5-methylbenzyl)amino]-9-ethyl-9H-purin-2-yl}amino)-2-methyl-butan-2-ol, 4-({6-[(2-amino-5-methylbenzyl)

amino]-9-isopropyl-9H-purin-2-yl}amino)-2-methyl-butan-2-ol, 4-({6-[(2-amino-5-methylbenzyl)amino]-9-cyclohexyl-9H-purin-2-yl}amino)-2-methyl-butan-2-ol, 4-({6-[(2-amino-5-methylbenzyl)amino]-9-benzyl-9H-purin-2-yl}amino)-2-methyl-butan-2-ol, 4-({6-[(2-amino-5-methylbenzyl)amino]-9-methyl-9H-purin-2-yl}amino)-2-methyl-pentan-2-ol, 4-({6-[(2-amino-5-methylbenzyl)amino]-9-ethyl-9H-purin-2-yl}amino)-2-methyl-pentan-2-ol, 4-({6-[(2-amino-5-methylbenzyl)amino]-9-isopropyl-9H-purin-2-yl}amino)-2-methyl-pentan-2-ol, 4-({6-[(2-amino-5-methylbenzyl)amino]-9-cyclohexyl-9H-purin-2-yl}amino)-2-methyl-pentan-2-ol, 4-({6-[(2-amino-5-methylbenzyl)amino]-9-benzyl-9H-purin-2-yl}amino)-2-methyl-pentan-2-ol, 4-({6-[(2-amino-5-methylbenzyl)amino]-9-methyl-9H-purin-2-yl}amino)-2,3-dimethyl-butan-2-ol, 4-({6-[(2-amino-5-methylbenzyl)amino]-9-ethyl-9H-purin-2-yl}amino)-2,3-dimethyl-butan-2-ol, 4-({6-[(2-amino-5-methylbenzyl)amino]-9-isopropyl-9H-purin-2-yl}amino)-2,3-dimethyl-butan-2-ol, 4-({6-[(2-amino-5-methylbenzyl)amino]-9-cyclohexyl-9H-purin-2-yl}amino)-2,3-dimethyl-butan-2-ol, 4-({6-[(2-amino-5-methylbenzyl)amino]-9-benzyl-9H-purin-2-yl}amino)-2,3-dimethyl-butan-2-ol, 3-({6-[(2-amino-5-methylbenzyl)amino]-9-methyl-9H-purin-2-yl}amino)-2-methyl-pentan-2-ol, 3-({6-[(2-amino-5-methylbenzyl)amino]-9-ethyl-9H-purin-2-yl}amino)-2-methyl-pentan-2-ol, 3-({6-[(2-amino-5-methylbenzyl)amino]-9-isopropyl-9H-purin-2-yl}amino)-2-methyl-pentan-2-ol, 3-({6-[(2-amino-5-methylbenzyl)amino]-9-cyclohexyl-9H-purin-2-yl}amino)-2-methyl-pentan-2-ol, 3-({6-[(2-amino-5-methylbenzyl)amino]-9-benzyl-9H-purin-2-yl}amino)-2-methyl-pentan-2-ol, 3-({6-[(2-amino-5-methylbenzyl)amino]-9-methyl-9H-purin-2-yl]amino}pentan-2-ol, 3-({6-[(2-amino-5-methylbenzyl)amino]-9-ethyl-9H-purin-2-yl]amino}pentan-2-ol, 3-({6-[(2-amino-5-methylbenzyl)amino]-9-isopropyl-9H-purin-2-yl]amino}pentan-2-ol, 3-({6-[(2-amino-5-methylbenzyl)amino]-9-cyclohexyl-9H-purin-2-yl]amino}pentan-2-ol, 3-({6-[(2-amino-5-methylbenzyl)amino]-9-benzyl-9H-purin-2-yl]amino}pentan-2-ol, 1-({6-[(2-amino-5-methylbenzyl)amino]-9-cyclopropyl-9H-purin-2-yl}amino)-2-methyl-propan-2-ol, 1-({6-[(2-amino-5-methylbenzyl)amino]-9-cyclohexyl-9H-purin-2-yl}amino)-2-methyl-propan-2-ol, 1-({6-[(2-amino-5-methylbenzyl)amino]-9-benzyl-9H-purin-2-yl}amino)-2-methyl-propan-2-ol, 2-({6-[(2-amino-4-methylbenzyl)amino]-9-methyl-9H-purin-2-yl}amino)butan-1-ol, 2-({6-[(2-amino-4-methylbenzyl)amino]-9-ethyl-9H-purin-2-yl}amino)butan-1-ol, 2-({6-[(2-amino-4-methylbenzyl)amino]-9-cyclohexyl-9H-purin-2-yl}amino)butan-1-ol, 2-({6-[(2-amino-4-methylbenzyl)amino]-9-benzyl-9H-purin-2-yl}amino)butan-1-ol, $N^6$-(2-amino-4-methylbenzyl)-$N^2$-(2-aminopropyl)-9-methyl-9H-purine-2,6-diamine, $N^6$-(2-amino-4-methylbenzyl)-$N^2$-(2-aminopropyl)-9-ethyl-9H-purine-2,6-diamine, $N^6$-(2-amino-4-methylbenzyl)-$N^2$-(2-aminopropyl)-9-isopropyl-9H-purine-2,6-diamine, $N^6$-(2-amino-5-fluorobenzyl)-$N^2$-(2-aminopropyl)-9-cyclohexyl-9H-purine-2,6-diamine, $N^6$-(2-amino-5-fluorobenzyl)-$N^2$-(2-aminopropyl)-9-benzyl-9H-purine-2,6-diamine, 2-({6-[(2-amino-5-fluorobenzyl)amino]-9-methyl-9H-purin-2-yl}amino)-3-methyl-butan-1-ol, 2-({6-[(2-amino-5-fluorobenzyl)amino]-9-ethyl-9H-purin-2-yl}amino)-3-methyl-butan-1-ol, 2-({6-[(2-amino-5-fluorobenzyl)amino]-9-isopropyl-9H-purin-2-yl}amino)-3-methyl-butan-1-ol, 2-({6-[(2-amino-4-methylbenzyl)amino]-9-cyclohexyl-9H-purin-2-yl}amino)-3-methyl-butan-1-ol, 2-({6-[(2-amino-4-methylbenzyl)amino]-9-benzyl-9H-purin-2-yl}amino)-3-methyl-butan-1-ol, $N^6$-(2-amino-4-methylbenzyl)-$N^2$-(4-aminocyclohexyl)-9-methyl-9H-purine-2,6-diamine, $N^6$-(2-amino-4-methylbenzyl)-$N^2$-(4-aminocyclohexyl)-9-ethyl-9H-purine-2,6-diamine, $N^6$-(2-amino-4-methylbenzyl)-$N^2$-(4-aminocyclohexyl)-9-isopropyl-9H-purine-2,6-diamine, $N^6$-(2-amino-4-methylbenzyl)-$N^2$-(4-aminocyclohexyl)-9-methyl-9H-purine-2,6-diamine, $N^6$-(2-amino-4-methylbenzyl)-$N^2$-(4-aminocyclohexyl)-9-cyclohexyl-9H-purine-2,6-diamine, $N^6$-(2-amino-4-methylbenzyl)-$N^2$-(4-aminocyclohexyl)-9-benzyl-9H-purine-2,6-diamine, 1-({6-[(2-amino-4-methylbenzyl)amino]-9-methyl-9H-purin-2-yl}amino)-2-methyl-propan-2-ol, 1-({6-[(2-amino-4-methylbenzyl)amino]-9-ethyl-9H-purin-2-yl}amino)-2-methyl-propan-2-ol, 1-({6-[(2-amino-4-methylbenzyl)amino]-9-isopropyl-9H-purin-2-yl}amino)-2-methyl-propan-2-ol, 1-({6-[(2-amino-4-methylbenzyl)amino]-9-methyl-9H-purin-2-yl}amino)propan-2-ol, 1-({6-[(2-amino-4-methylbenzyl)amino]-9-ethyl-9H-purin-2-yl}amino)propan-2-ol, 1-({6-[(2-amino-4-methylbenzyl)amino]-9-isopropyl-9H-purin-2-yl}amino)propan-2-ol, 1-({6-[(2-amino-4-methylbenzyl)amino]-9-cyclohexyl-9H-purin-2-yl}amino)propan-2-ol, 1-({6-[(2-amino-4-methylbenzyl)amino]-9-benzyl-9H-purin-2-yl}amino)propan-2-ol, 3-({6-[(2-amino-4-methylbenzyl)amino]-9-methyl-9H-purin-2-yl}amino)-2-methyl-butan-2-ol, 3-({6-[(2-amino-4-methylbenzyl)amino]-9-ethyl-9H-purin-2-yl}amino)-2-methyl-butan-2-ol, 3-({6-[(2-amino-4-methylbenzyl)amino]-9-isopropyl-9H-purin-2-yl}amino)-2-methyl-butan-2-ol, 3-({6-[(2-amino-4-methylbenzyl)amino]-9-cyclohexyl-9H-purin-2-yl}amino)-2-methyl-butan-2-ol, 3-({6-[(2-amino-4-methylbenzyl)amino]-9-benzyl-9H-purin-2-yl}amino)-2-methyl-butan-2-ol, 4-({6-[(2-amino-4-methylbenzyl)amino]-9-methyl-9H-purin-2-yl}amino)-2-methyl-butan-2-ol, 4-({6-[(2-amino-4-methylbenzyl)amino]-9-ethyl-9H-purin-2-yl}amino)-2-methyl-butan-2-ol, 4-({6-[(2-amino-4-methylbenzyl)amino]-9-isopropyl-9H-purin-2-yl}amino)-2-methyl-butan-2-ol, 4-({6-[(2-amino-4-methylbenzyl)amino]-9-cyclohexyl-9H-purin-2-yl}amino)-2-methyl-butan-2-ol, 4-({6-[(2-amino-4-methylbenzyl)amino]-9-benzyl-9H-purin-2-yl}amino)-2-methyl-butan-2-ol, 4-({6-[(2-amino-4-methylbenzyl)amino]-9-methyl-9H-purin-2-yl}amino)-2-methyl-pentan-2-ol, 4-({6-[(2-amino-4-methylbenzyl)amino]-9-ethyl-9H-purin-2-yl}amino)-2-methyl-pentan-2-ol, 4-({6-[(2-amino-4-methylbenzyl)amino]-9-isopropyl-9H-purin-2-yl}amino)-2-methyl-pentan-2-ol, 4-({6-[(2-amino-4-methylbenzyl)amino]-9-cyclohexyl-9H-purin-2-yl}amino)-2-methyl-pentan-2-ol, 4-({6-[(2-amino-4-methylbenzyl)amino]-9-benzyl-9H-purin-2-yl}amino)-2-methyl-pentan-2-ol, 4-({6-[(2-amino-4-methylbenzyl)amino]-9-methyl-9H-purin-2-yl}amino)-2,3-dimethyl-butan-2-ol, 4-({6-[(2-amino-4-methylbenzyl)amino]-9-ethyl-9H-purin-2-yl}amino)-2,3-dimethyl-butan-2-ol, 4-({6-[(2-amino-4-methylbenzyl)amino]-9-isopropyl-9H-purin-2-yl}amino)-2,3-dimethyl-butan-2-ol, 4-({6-[(2-amino-4-methylbenzyl)amino]-9-cyclohexyl-9H-purin-2-yl}amino)-2,3-dimethyl-butan-2-ol, 4-({6-[(2-amino-4-methylbenzyl)amino]-9-benzyl-9H-purin-2-yl}amino)-2,3-dimethyl-butan-2-ol, 3-({6-[(2-amino-4-methylbenzyl)amino]-9-methyl-9H-purin-2-yl}amino)-2-methyl-pentan-2-ol, 3-({6-[(2-amino-4-methylbenzyl)amino]-9-ethyl-9H-purin-2-yl}amino)-2-methyl-pentan-2-ol, 3-({6-[(2-amino-4-methylbenzyl)amino]-9-isopropyl-9H-purin-2-yl}amino)-2-methyl-pentan-2-ol, 3-({6-[(2-amino-4-methylbenzyl)amino]-9-cyclohexyl-9H-purin-2-yl}amino)-2-methyl-pentan-2-ol, 3-({6-[(2-amino-4-methylbenzyl)amino]-9-benzyl-9H-purin-2-yl}amino)-2-methyl-pentan-2-ol, 3-({6-[(2-amino-4-methylbenzyl)amino]-9-methyl-9H-purin-2-yl]amino}pentan-2-ol, 3-({6-[(2-amino-4-methylbenzyl)

amino]-9-ethyl-9H-purin-2-yl]amino}pentan-2-ol, 3-({6-[(2-amino-4-methylbenzyl)amino]-9-isopropyl-9H-purin-2-yl]amino}pentan-2-ol, 3-({6-[(2-amino-4-methylbenzyl)amino]-9-cyclohexyl-9H-purin-2-yl]amino}pentan-2-ol, 3-({6-[(2-amino-4-methylbenzyl)amino]-9-benzyl-9H-purin-2-yl]amino}pentan-2-ol, 1-({6-[(2-amino-4-methylbenzyl)amino]-9-cyclopropyl-9H-purin-2-yl}amino)-2-methyl-propan-2-ol, 1-({6-[(2-amino-4-methylbenzyl)amino]-9-cyclohexyl-9H-purin-2-yl}amino)-2-methyl-propan-2-ol, 1-({6-[(2-amino-4-methylbenzyl)amino]-9-benzyl-9H-purin-2-yl}amino)-2-methyl-propan-2-ol, 2-({6-[(2-amino-3-methoxylbenzyl)amino]-9-methyl-9H-purin-2-yl}amino)butan-1-ol, 2-({6-[(2-amino-3-methoxylbenzyl)amino]-9-ethyl-9H-purin-2-yl}amino)butan-1-ol, 2-({6-[(2-amino-3-methoxylbenzyl)amino]-9-cyclohexyl-9H-purin-2-yl}amino)butan-1-ol, 2-({6-[(2-amino-3-methoxylbenzyl)amino]-9-benzyl-9H-purin-2-yl}amino)butan-1-ol, $N^6$-(2-amino-3-methoxylbenzyl)-$N^2$-(2-aminopropyl)-9-methyl-9H-purine-2,6-diamine, $N^6$-(2-amino-3-methoxylbenzyl)-$N^2$-(2-aminopropyl)-9-ethyl-9H-purine-2,6-diamine, $N^6$-(2-amino-3-methoxylbenzyl)-$N^2$-(2-aminopropyl)-9-isopropyl-9H-purine-2,6-diamine, $N^6$-(2-amino-3-methoxylbenzyl)-$N^2$-(2-aminopropyl)-9-cyclohexyl-9H-purine-2,6-diamine, $N^6$-(2-amino-3-methoxylbenzyl)-$N^2$-(2-aminopropyl)-9-benzyl-9H-purine-2,6-diamine, 2-({6-[(2-amino-3-methoxylbenzyl)amino]-9-methyl-9H-purin-2-yl}amino)-3-methyl-butan-1-ol, 2-({6-[(2-amino-3-methoxylbenzyl)amino]-9-ethyl-9H-purin-2-yl}amino)-3-methyl-butan-1-ol, 2-({6-[(2-amino-3-methoxylbenzyl)amino]-9-isopropyl-9H-purin-2-yl}amino)-3-methyl-butan-1-ol, 2-({6-[(2-amino-3-methoxylbenzyl)amino]-9-cyclohexyl-9H-purin-2-yl}amino)-3-methyl-butan-1-ol, 2-({6-[(2-amino-3-methoxylbenzyl)amino]-9-benzyl-9H-purin-2-yl}amino)-3-methyl-butan-1-ol, $N^6$-(2-amino-3-methoxylbenzyl)-$N^2$-(4-aminocyclohexyl)-9-methyl-9H-purine-2,6-diamine, $N^6$-(2-amino-3-methoxylbenzyl)-$N^2$-(4-aminocyclohexyl)-9-ethyl-9H-purine-2,6-diamine, $N^6$-(2-amino-3-methoxylbenzyl)-$N^2$-(4-aminocyclohexyl)-9-isopropyl-9H-purine-2,6-diamine, $N^6$-(2-amino-3-methoxylbenzyl)-$N^2$-(4-aminocyclohexyl)-9-methyl-9H-purine-2,6-diamine, $N^6$-(2-amino-3-methoxylbenzyl)-$N^2$-(4-aminocyclohexyl)-9-cyclohexyl-9H-purine-2,6-diamine, $N^6$-(2-amino-3-methoxylbenzyl)-$N^2$-(4-aminocyclohexyl)-9-benzyl-9H-purine-2,6-diamine, 1-({6-[(2-amino-3-methoxylbenzyl)amino]-9-methyl-9H-purin-2-yl}amino)-2-methyl-propan-2-ol, 1-({6-[(2-amino-3-methoxylbenzyl)amino]-9-ethyl-9H-purin-2-yl}amino)-2-methyl-propan-2-ol, 1-({6-[(2-amino-3-methoxylbenzyl)amino]-9-isopropyl-9H-purin-2-yl}amino)-2-methyl-propan-2-ol, 1-({6-[(2-amino-3-methoxybenzyl)amino]-9-methyl-9H-purin-2-yl}amino)propan-2-ol, 1-({6-[(2-amino-3-methoxybenzyl)amino]-9-ethyl-9H-purin-2-yl}amino)propan-2-ol, 1-({6-[(2-amino-3-methoxybenzyl)amino]-9-isopropyl-9H-purin-2-yl}amino)propan-2-ol, 1-({6-[(2-amino-3-methoxybenzyl)amino]-9-cyclohexyl-9H-purin-2-yl}amino)propan-2-ol, 1-({6-[(2-amino-3-methoxybenzyl)amino]-9-benzyl-9H-purin-2-yl}amino)propan-2-ol, 3-({6-[(2-amino-3-methoxylbenzyl)amino]-9-methyl-9H-purin-2-yl}amino)-2-methyl-butan-2-ol, 3-({6-[(2-amino-3-methoxylbenzyl)amino]-9-ethyl-9H-purin-2-yl}amino)-2-methyl-butan-2-ol, 3-({6-[(2-amino-3-methoxylbenzyl)amino]-9-isopropyl-9H-purin-2-yl}amino)-2-methyl-butan-2-ol, 3-({6-[(2-amino-3-methoxylbenzyl)amino]-9-cyclohexyl-9H-purin-2-yl}amino)-2-methyl-butan-2-ol, 3-({6-[(2-amino-3-methoxylbenzyl)amino]-9-benzyl-9H-purin-2-yl}amino)-2-methyl-butan-2-ol, 4-({6-[(2-amino-3-methoxylbenzyl)amino]-9-methyl-9H-purin-2-yl}amino)-2-methyl-butan-2-ol, 4-({6-[(2-amino-3-methoxylbenzyl)amino]-9-ethyl-9H-purin-2-yl}amino)-2-methyl-butan-2-ol, 4-({6-[(2-amino-3-methoxylbenzyl)amino]-9-isopropyl-9H-purin-2-yl}amino)-2-methyl-butan-2-ol, 4-({6-[(2-amino-3-methoxylbenzyl)amino]-9-cyclohexyl-9H-purin-2-yl}amino)-2-methyl-butan-2-ol, 4-({6-[(2-amino-3-methoxylbenzyl)amino]-9-benzyl-9H-purin-2-yl}amino)-2-methyl-butan-2-ol, 4-({6-[(2-amino-3-methoxylbenzyl)amino]-9-methyl-9H-purin-2-yl}amino)-2-methyl-pentan-2-ol, 4-({6-[(2-amino-3-methoxylbenzyl)amino]-9-ethyl-9H-purin-2-yl}amino)-2-methyl-pentan-2-ol, 4-({6-[(2-amino-3-methoxylbenzyl)amino]-9-isopropyl-9H-purin-2-yl}amino)-2-methyl-pentan-2-ol, 4-({6-[(2-amino-3-methoxylbenzyl)amino]-9-cyclohexyl-9H-purin-2-yl}amino)-2-methyl-pentan-2-ol, 4-({6-[(2-amino-3-methoxylbenzyl)amino]-9-benzyl-9H-purin-2-yl}amino)-2-methyl-pentan-2-ol, 4-({6-[(2-amino-3-methoxylbenzyl)amino]-9-methyl-9H-purin-2-yl}amino)-2,3-dimethyl-butan-2-ol, 4-({6-[(2-amino-3-methoxylbenzyl)amino]-9-ethyl-9H-purin-2-yl}amino)-2,3-dimethyl-butan-2-ol, 4-({6-[(2-amino-3-methoxylbenzyl)amino]-9-isopropyl-9H-purin-2-yl}amino)-2,3-dimethyl-butan-2-ol, 4-({6-[(2-amino-3-methoxylbenzyl)amino]-9-cyclohexyl-9H-purin-2-yl}amino)-2,3-dimethyl-butan-2-ol, 4-({6-[(2-amino-3-methoxylbenzyl)amino]-9-benzyl-9H-purin-2-yl}amino)-2,3-dimethyl-butan-2-ol, 3-({6-[(2-amino-3-methoxylbenzyl)amino]-9-methyl-9H-purin-2-yl}amino)-2-methyl-pentan-2-ol, 3-({6-[(2-amino-3-methoxylbenzyl)amino]-9-ethyl-9H-purin-2-yl}amino)-2-methyl-pentan-2-ol, 3-({6-[(2-amino-3-methoxylbenzyl)amino]-9-isopropyl-9H-purin-2-yl}amino)-2-methyl-pentan-2-ol, 3-({6-[(2-amino-3-methoxylbenzyl)amino]-9-cyclohexyl-9H-purin-2-yl}amino)-2-methyl-pentan-2-ol, 3-({6-[(2-amino-3-methoxylbenzyl)amino]-9-benzyl-9H-purin-2-yl}amino)-2-methyl-pentan-2-ol, 3-({6-[(2-amino-3-methoxylbenzyl)amino]-9-methyl-9H-purin-2-yl]amino}pentan-2-ol, 3-({6-[(2-amino-3-methoxylbenzyl)amino]-9-ethyl-9H-purin-2-yl]amino}pentan-2-ol, 3-({6-[(2-amino-3-methoxylbenzyl)amino]-9-isopropyl-9H-purin-2-yl]amino}pentan-2-ol, 3-({6-[(2-amino-3-methoxylbenzyl)amino]-9-cyclohexyl-9H-purin-2-yl]amino}pentan-2-ol, 3-({6-[(2-amino-3-methoxylbenzyl)amino]-9-benzyl-9H-purin-2-yl]amino}pentan-2-ol, 1-({6-[(2-amino-3-methoxylbenzyl)amino]-9-cyclopropyl-9H-purin-2-yl}amino)-2-methyl-propan-2-ol, 1-({6-[(2-amino-3-methoxylbenzyl)amino]-9-cyclohexyl-9H-purin-2-yl}amino)-2-methyl-propan-2-ol, 1-({6-[(2-amino-3-methoxylbenzyl)amino]-9-benzyl-9H-purin-2-yl}amino)-2-methyl-propan-2-ol, 1-({6-[(2-amino-5-methoxybenzyl)amino]-9-methyl-9H-purin-2-yl}amino)propan-2-ol, 1-({6-[(2-amino-5-methoxybenzyl)amino]-9-ethyl-9H-purin-2-yl}amino)propan-2-ol, 1-({6-[(2-amino-5-methoxybenzyl)amino]-9-isopropyl-9H-purin-2-yl}amino)propan-2-ol, 1-({6-[(2-amino-5-methoxybenzyl)amino]-9-cyclohexyl-9H-purin-2-yl}amino)propan-2-ol, 1-({6-[(2-amino-5-methoxybenzyl)amino]-9-benzyl-9H-purin-2-yl}amino)propan-2-ol, 2-({6-[(2-amino-5-methoxylbenzyl)amino]-9-methyl-9H-purin-2-yl}amino)butan-1-ol, 2-({6-[(2-amino-5-methoxylbenzyl)amino]-9-ethyl-9H-purin-2-yl}amino)butan-1-ol, 2-({6-[(2-amino-5-methoxylbenzyl)amino]-9-cyclohexyl-9H-purin-2-yl}amino)butan-1-ol, 2-({6-[(2-amino-5-methoxylbenzyl)amino]-9-benzyl-9H-purin-2-yl}amino)butan-1-ol, $N^6$-(2-amino-5-methoxylbenzyl)-$N^2$-(2-aminopropyl)-9-methyl-9H-purine-2,6-diamine, $N^6$-(2-amino-5-methoxylbenzyl)-$N^2$-(2-aminopropyl)-9-ethyl-9H-purine-2,6-diamine, $N^6$-(2-amino-5-methoxylbenzyl)-$N^2$-(2-aminopropyl)-9-isopropyl-9H-purine-2,6-diamine, $N^6$-(2-amino-5- fluorobenzyl)-N²-(2-aminopropyl)-9-cyclohexyl-9H-purine-2,6-diamine, N⁶-(2-amino-5-fluorobenzyl)-N²-(2-aminopropyl)-9-benzyl-9H-purine-2,6-diamine, 2-({6-[(2-amino-5-fluorobenzyl)amino]-9-methyl-9H-purin-2-yl}amino)-3-methyl-butan-1-ol, 2-({6-[(2-amino-5-fluorobenzyl)amino]-9-ethyl-9H-purin-2-yl}amino)-3-methyl-butan-1-ol, 2-({6-[(2-amino-5-fluorobenzyl)amino]-9-isopropyl-9H-purin-2-yl}amino)-3-methyl-butan-1-ol, 2-({6-[(2-amino-5-methoxylbenzyl)amino]-9-cyclohexyl-9H-purin-2-yl}amino)-3-methyl-butan-1-ol, 2-({6-[(2-amino-5-methoxylbenzyl)amino]-9-benzyl-9H-purin-2-yl}amino)-3-methyl-butan-1-ol, N⁶-(2-amino-5-methoxylbenzyl)-N²-(4-aminocyclohexyl)-9-methyl-9H-purine-2,6-diamine, N⁶-(2-amino-5-methoxylbenzyl)-N²-(4-aminocyclohexyl)-9-ethyl-9H-purine-2,6-diamine, N⁶-(2-amino-5-methoxylbenzyl)-N²-(4-aminocyclohexyl)-9-isopropyl-9H-purine-2,6-diamine, N⁶-(2-amino-5-methoxylbenzyl)-N²-(4-aminocyclohexyl)-9-methyl-9H-purine-2,6-diamine, N⁶-(2-amino-5-methoxylbenzyl)-N²-(4-aminocyclohexyl)-9-cyclohexyl-9H-purine-2,6-diamine, N⁶-(2-amino-5-methoxylbenzyl)-N²-(4-aminocyclohexyl)-9-benzyl-9H-purine-2,6-diamine, 1-({6-[(2-amino-5-methoxylbenzyl)amino]-9-methyl-9H-purin-2-yl}amino)-2-methyl-propan-2-ol, 1-({6-[(2-amino-5-methoxylbenzyl)amino]-9-ethyl-9H-purin-2-yl}amino)-2-methyl-propan-2-ol, 1-({6-[(2-amino-5-methoxylbenzyl)amino]-9-isopropyl-9H-purin-2-yl}amino)-2-methyl-propan-2-ol, 3-({6-[(2-amino-5-methoxylbenzyl)amino]-9-methyl-9H-purin-2-yl}amino)-2-methyl-butan-2-ol, 3-({6-[(2-amino-5-methoxylbenzyl)amino]-9-ethyl-9H-purin-2-yl}amino)-2-methyl-butan-2-ol, 3-({6-[(2-amino-5-methoxylbenzyl)amino]-9-isopropyl-9H-purin-2-yl}amino)-2-methyl-butan-2-ol, 3-({6-[(2-amino-5-methoxylbenzyl)amino]-9-cyclopropyl-9H-purin-2-yl}amino)-2-methyl-butan-2-ol, 3-({6-[(2-amino-5-methoxylbenzyl)amino]-9-cyclohexyl-9H-purin-2-yl}amino)-2-methyl-butan-2-ol, 3-({6-[(2-amino-5-methoxylbenzyl)amino]-9-benzyl-9H-purin-2-yl}amino)-2-methyl-butan-2-ol, 4-({6-[(2-amino-5-methoxylbenzyl)amino]-9-methyl-9H-purin-2-yl}amino)-2-methyl-butan-2-ol, 4-({6-[(2-amino-5-methoxylbenzyl)amino]-9-ethyl-9H-purin-2-yl}amino)-2-methyl-butan-2-ol, 4-({6-[(2-amino-5-methoxylbenzyl)amino]-9-isopropyl-9H-purin-2-yl}amino)-2-methyl-butan-2-ol, 4-({6-[(2-amino-5-methoxylbenzyl)amino]-9-cyclohexyl-9H-purin-2-yl}amino)-2-methyl-butan-2-ol, 4-({6-[(2-amino-5-methoxylbenzyl)amino]-9-benzyl-9H-purin-2-yl}amino)-2-methyl-butan-2-ol, 4-({6-[(2-amino-5-methoxylbenzyl)amino]-9-methyl-9H-purin-2-yl}amino)-2-methyl-pentan-2-ol, 4-({6-[(2-amino-5-methoxylbenzyl)amino]-9-ethyl-9H-purin-2-yl}amino)-2-methyl-pentan-2-ol, 4-({6-[(2-amino-5-methoxylbenzyl)amino]-9-isopropyl-9H-purin-2-yl}amino)-2-methyl-pentan-2-ol, 4-({6-[(2-amino-5-methoxylbenzyl)amino]-9-cyclohexyl-9H-purin-2-yl}amino)-2-methyl-pentan-2-ol, 4-({6-[(2-amino-5-methoxylbenzyl)amino]-9-benzyl-9H-purin-2-yl}amino)-2-methyl-pentan-2-ol, 4-({6-[(2-amino-5-methoxylbenzyl)amino]-9-methyl-9H-purin-2-yl}amino)-2,3-dimethyl-butan-2-ol, 4-({6-[(2-amino-5-methoxylbenzyl)amino]-9-ethyl-9H-purin-2-yl}amino)-2,3-dimethyl-butan-2-ol, 4-({6-[(2-amino-5-methoxylbenzyl)amino]-9-isopropyl-9H-purin-2-yl}amino)-2,3-dimethyl-butan-2-ol, 4-({6-[(2-amino-5-methoxylbenzyl)amino]-9-cyclohexyl-9H-purin-2-yl}amino)-2,3-dimethyl-butan-2-ol, 4-({6-[(2-amino-5-methoxylbenzyl)amino]-9-benzyl-9H-purin-2-yl}amino)-2,3-dimethyl-butan-2-ol, 3-({6-[(2-amino-5-methoxylbenzyl)amino]-9-methyl-9H-purin-2-yl}amino)-2-methyl-pentan-2-ol, 3-({6-[(2-amino-5-methoxylbenzyl)amino]-9-ethyl-9H-purin-2-yl}amino)-2-methyl-pentan-2-ol, 3-({6-[(2-amino-5-methoxylbenzyl)amino]-9-isopropyl-9H-purin-2-yl}amino)-2-methyl-pentan-2-ol, 3-({6-[(2-amino-5-methoxylbenzyl)amino]-9-cyclohexyl-9H-purin-2-yl}amino)-2-methyl-pentan-2-ol, 3-({6-[(2-amino-5-methoxylbenzyl)amino]-9-benzyl-9H-purin-2-yl}amino)-2-methyl-pentan-2-ol, 3-({6-[(2-amino-5-methoxylbenzyl)amino]-9-methyl-9H-purin-2-yl]amino}pentan-2-ol, 3-({6-[(2-amino-5-methoxylbenzyl)amino]-9-ethyl-9H-purin-2-yl]amino}pentan-2-ol, 3-({6-[(2-amino-5-methoxylbenzyl)amino]-9-isopropyl-9H-purin-2-yl]amino}pentan-2-ol, 3-({6-(2-amino-5-methoxylbenzyl)amino]-9-cyclohexyl-9H-purin-2-yl]amino}pentan-2-ol, 3-({6-[(2-amino-5-methoxylbenzyl)amino]-9-benzyl-9H-purin-2-yl]amino}pentan-2-ol, 1-({6-[(2-amino-5-methoxylbenzyl)amino]-9-cyclopropyl-9H-purin-2-yl}amino)-2-methyl-propan-2-ol, 1-({6-[(2-amino-5-methoxylbenzyl)amino]-9-cyclohexyl-9H-purin-2-yl}amino)-2-methyl-propan-2-ol, 1-({6-[(2-amino-5-methoxylbenzyl)amino]-9-benzyl-9H-purin-2-yl}amino)-2-methyl-propan-2-ol.

Processes for Preparation

The starting material for the compounds of the formula I is 2,6-dichloropurine prepared from hypoxanthine and hypoxanthine-1-N-oxide by chlorination with $POCl_3$ (Davoll and Blowy, *J. Am. Chem. Soc.* 1957; 73:2936). The starting material is also available from commercial sources (Sigma, Aldrich, Fluka, etc.).

In one approach the 2,6-disubstituted purines of the formula I are prepared from 2,6-dichloropurine by reaction with an appropriate nucleophile. 2,6-Dichloropurine is dissolved in n-butanol and the appropriate $R^6$-amine (1.5-5 eq.) and several-fold excess of triethylamine is added. After heating for several hours, the reaction mixture is cooled and the 2-chloro-6-substituted purine is obtained. $R^9$ substituted derivatives are prepared from 2-chloro-6-substituted purines (in DMSO or DMF), to which powdered calcium carbonate (approximately 3 eq.) is added, followed by $R^9$-halogen. After several hours or days of vigorous stirring the product is isolated by means of liquid chromatography. Substitution of $C^2$—Cl is then achieved by reaction with the second nucleophile (5-30 equivalents of substituted amines, aminoalkanols; mercapto derivatives with the presence of N-methylpyrrolidinone or N-ethyl-diisopropylamine) at temperature of 160-180° C. Product is finally isolated by liquid chromatography or crystallized from n-BuOH or water.

Therapeutic Administration

Suitable routes for administration include oral, rectal, topical (including dermal, ocular, buccal and sublingual), vaginal and parenteral (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutical composition comprises about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of convectional mixing, granulating, coating, dissolving or lyophilising processes.

Preferably, solutions of the active ingredient, and in addition also suspensions or dispersions, especially isotonic aqueous solutions, dispersions or suspensions, are used, it being possible for these to be prepared before use, for example in the case of lyophilised compositions which comprise the active substance by itself or together with a carrier, for example mannitol. The pharmaceutical compositions can be sterilised and/or comprise excipients, for example preservatives, stabilisers, wetting agents and/or emulsifiers, solubilizing agents, salts for regulating the osmotic pressure and/or buffers, and they are prepared in a manner known per se, for example by means of convectional dissolving or lyophilising processes. The solutions or suspensions mentioned can comprise viscosity-increasing substances, such as sodium carboxymethylcellulose, carboxymethylcellulose, dextran, polyvinylpyrrolidone or gelatin.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, acid, arachidonic acid, behenic acid or corresponding unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris) and/or "Miglyol 812" (triglyceride of saturated fatty acids of chain length $C_8$ to $C_{12}$ from Hüls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients. Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, are also hard capsules of gelatin and soft, closed capsules of gelatin and a plasticiser, such as glycerol or sorbitol. The hard capsules can contain the active ingredient in the form of granules, mixed for example with fillers, such as maize starch, binders and/or lubricants, such as talc or magnesium stearate, and stabilisers if appropriate. In soft capsules, the active ingredient is preferably dissolved or suspended in suitable liquid excipients, such as greasy oils, paraffin oil or liquid polyethylene glycols or fatty acid esters of ethylene glycol or propylene glycol, it being likewise possible to add stabilisers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilisers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists of, in particular, hydrocarbons, for example vaseline, paraffin oil or hard paraffins, which preferably comprise suitable hydroxy compounds, such as fatty alcohols or esters thereof, for example cetyl alcohol or wool wax alcohols, such as wool wax, to improve the water-binding capacity. Emulsifiers are lipophilic substances, such as sorbitan fatty acid esters (Spans), preferably sorbitan oleate or sorbitan isostearate. Additives to the aqueous phase are, for example, humectants, such as polyalcohols, for example glycerol, propylene glycol, sorbitol and polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or hydrogenated oils, for example hydrogenated groundnut or castor oil, and furthermore fatty acid partial esters of glycerol, for example glycerol mono- and distearate. They also contain e.g. fatty alcohols, emulsifiers and additives mentioned in connection with ointments which increase the uptake of water.

Creams are oil-in-water emulsions, which comprise more than 50% of water. Oily bases used are, in particular, fatty alcohols, for example isopropyl myristate, wool wax, beeswax, or hydrocarbons, for example vaseline (petrolatum) or paraffin oil.

Emulsifiers are surface-active substances with predominantly hydrophilic properties, such as corresponding non-ionic emulsifiers, for example fatty acid esters of polyalcohols or ethyleneoxy adducts thereof, such as polyglyceric fatty acid esters or polyethylene sorbitan fatty acid esters or acidic polyglyceric fatty acid esters (Tween), and furthermore polyoxyethylene fatty alcohol ethers or polyoxyethylene fatty acid esters, or ionic emulsifiers, such as alkali metal salts of fatty alcohol sulphates, preferably sodium lauryl sulphate, sodium cetyl sulphate or sodium stearyl sulphate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and polyethylene glycols, and furthermore preservatives and odoriferous substances.

Pastes are creams or ointments containing secretion-absorbing powder constituents, such as metal oxides, for example titanium oxide or zinc oxide, and in addition talc or aluminium silicates, which have the task of binding the moisture or secretions present.

Foams are administered from pressurised containers and they are liquid oil-in-water emulsions present in aerosol foam. As the propellant gases halogenated hydrocarbons, such as polyhalogenated alkanes, for example dichlorofluoromethane and dichlorotetrafluoroethane, or, preferably, non-halogenated gaseous hydrocarbons, air, $N_2O$, or carbon dioxide are used. The oily phases used are, inter alia, those mentioned above for ointments, and the additives mentioned there are likewise used.

Tinctures and solutions usually comprise an aqueous-ethanolic base to which, humectants for reducing evaporation, such as polyalcohols, for example glycerol, glycols and polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives are admixed.

This invention further provides veterinary preparations containing at least one active ingredient together with a veterinary carrier. Veterinary carriers are materials for the application of a composition and include solid, liquid or gaseous substances, which are inert or acceptable in veterinary medicine and are compatible with the active ingredient. These veterinary preparations can be administered orally, parenterally or by any other desired way.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

EXAMPLES OF CARRYING OUT THE INVENTION

Figure 1:
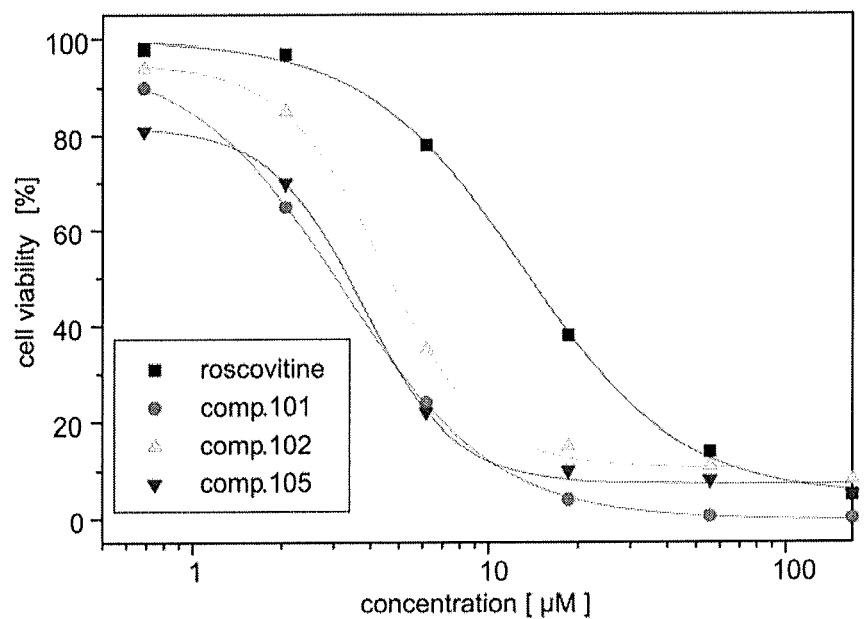
FIG. 1 displays the dose-dependent antiproliferative activities of selected purine derivatives against human tumor cell lines MCF7 and K562, with roscovitine as a standard.
Figure 1:
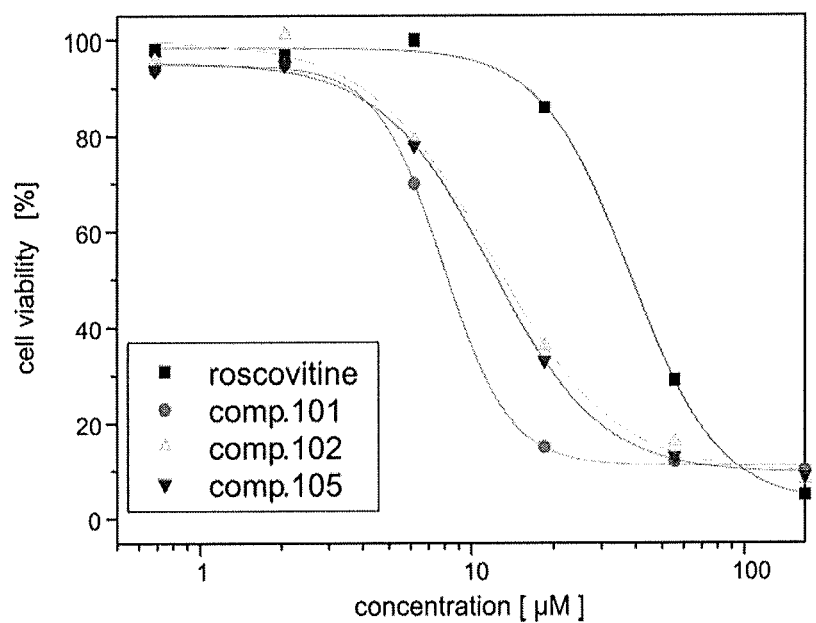

The following examples serve to illustrate the invention without limiting the scope thereof.

The starting material for the compounds of the formula I is 2,6-chloropurine, which is available from commercial sources (Sigma, Aldrich, Fluka, etc.). Melting points were determined on a Koffler block and are uncorrected. BÜCHI Melting Point B-540 Apparatus was used for melting point measurements. Elemental analyses (C, H, N) were measured on EA1108 CHN analysator (Thermo Finnigan). Evaporations were carried out on a rotary evaporator under vacuum at temperatures below 80° C. The NMR spectra (σ, ppm; J, Hz) were measured on Bruker Avance AV 300 instrument at the temperature 300 K and frequency 300.13 MHz ($^1$H), and 75.48 MHz ($^{13}$C), respectively. Samples were prepared by dissolving compounds in DMSO-$d_6$. All spectra were obtained at 25° C. using tetramethylsilane as an internal standard. Electron impact mass spectra were measured on Polaris Q (Finnigan) mass spectrometer equipped with a direct inlet probe (DIP) (70 eV, temperature gradient 40-450° C., interval m/z 50-1000 amu using cyclic scans of 3.0 sec (70 eV, 200° C., direct inlet). Quadrupole mass spectra were measured on a Micromass ZMD detector with electrospray ionization. ES+ mass spectra were measured using direct inlet on Waters ZMD 2000 mass spectrometer. Mass interval in the measurements was 10-1500 amu. The spectra were measured using cyclic scans of 3.0 sec, voltage on input slot was 25 V and temperature of the evaporation block 150° C., desolvation temperature 80° C. and desolvation gas flow 200 l/hour. The obtained data were worked-up using MassLynx data system. Merck silica gel Kieselgel 60 (230-400 mesh) was used for column chromatography. All compounds gave satisfactory elemental analyses (±0.4%). Analytical thin layer chromatography (TLC) was carried out on silica gel 60 WF$_{254}$ (Merck) plates, mobile phase CHCl$_3$:MeOH:conc.NH$_4$OH (8:2:0.2, v/v/v).

The starting 9-alkyl-2,6-dichloropurines were prepared using procedures described in the literature:

9-methyl-2,6-dichloropurine

1) Parker et al. Phytochemistry 25, 1986: 303-310
2) Brik et al. Bioorg. Med. Chem. 13, 2005: 4622-4626;

9-ethyl-2,6-dichloropurine

Pitts et al. Bioorg. Med. Chem. Let. 14, 2004: 2955-2958

9-isopropyl-2,6-dichloropurine

1) Rypka et al. Xenobiotica 32, 2002: 1017-1032
2) Lu et al. J. Org. Chem. 72, 2007: 5012-5015

9-benzyl-2,6-dichloropurine

1) Kelley et al. J. Med. Chem. 31; 1988: 2001-2004
2) Naito et al. Chem. Pharm. Bul. 30, 1982: 2011-2019
3) Dalby et al. Angew. Chem. German 105, 1993: 1822-1823
4) Brik et al. Bioorg. Med. Chem. 13, 2005; 4622-4626
5) Weterings et al. Bioorg. Med. Chem. Let. 16, 2006: 3258-3261
6) Toyota et al. Synth. Commun. 23, 1993: 1295-1305
7) Gundersen et al. Tetrahedron Let. 36, 1995: 1945-1948
8) Lu et al. J. Organ. Chem. 72, 2007: 5012-5015

9-cyclopropyl-2,6-dichloropurine 2,6-Dichloropurine (1 mmol), powdered potassium carbonate (4 mmol) and cyclopropyliodide were vigorously stirred in 5 mL DMSO overnight. After evaporation of the solvent the product was extracted (water/diethylether) and purified by column chromatography (silicagel/1% MeOH in CHCl$_3$). Crystallization from diethylether gave product in 35% yield, mp 121-124° C.

9-cyclopentyl-2,6-dichloropurine

1) Shum et al. Nucleos. Nucleot. 20, 2001: 1067-1078
2) Drezér et al. J. Med. Chem. 44, 2001: 524-530

9-cyclohexyl-2,6-dichloropurine 2,6-Dichloropurine (1 mmol), powdered potassium carbonate (4 mmol) and cyclohexyliodide were vigorously stirred in 5 mL DMSO overnight. After evaporation of the solvent the product was extracted (water/diethylether) and purified by column chromatography (silicagel/1% MeOH in CHCl$_3$). Crystallization from diethylether gave product in 41% yield, mp 116-121° C.

Example 1

Preparation of 9-alkyl-6-[(2-amino-$R_n$-benzyl)amino]-2-chloropurine precursor

9-Alkyl-2,6-dichloropurine (2 mmol), 2-aminobenzylamine (2.5 mmol) and triethylamine (0.4 mL) were heated in 5 mL of 1-butanol (110° C., 1.5 h). The product was crystallized from the reaction mixture during heating or after cooling in refrigerator to 4° C. The product was filtered and washed with 1-butanol. Only the 9-(pent-3-yl)-2-chloro-6-[(2-amino-$R_n$-benzyl)amino]purines were isolated by means of column chromatography (silica gel, CHCl$_3$/MeOH; 99/1). Products were recrystallized from CHCl$_3$-Et$_2$O.

6-[(2-aminobenzyl)amino]-2-chloro-9-methylpurine

Yield 91%; mp 202-210° C.; $^1$H-NMR (300.13 MHz, CDCl$_3$, 303K): 4.459 (2H, br s), 4.746 (2H, br s), 3.650 (3H, s), 6.446 (1H, br s), 6.673 (1H, dd, J=1.2, 7.9), 6.717 (1H, mt), 7.10 (1H, mt), 7.15 (1H, dd, J=7.7, 1.2), 7.682 (1H, s).

6-[(2-aminobenzyl)amino]-2-chloro-9-ethylpurine

Yield 90%; mp 190-198° C.; $^1$H-NMR (300.13 MHz, CDCl$_3$, 303K): 1.552 (3H, t, J=6.8), 4.150 (2H, q, J=6.8), 4.459 (2H, br s), 4.746 (2H, br s), 6.446 (1H, br s), 6.673 (1H, dd, J=1.2, J=7.9), 6.717 (1H, mt), 7.10 (1H, mt), 7.15 (1H, dd, J=7.7, 1.2), 7.682 (1H, s).

6-[(2-aminobenzyl)amino]-2-chloro-9-isopropylpurine

Yield 93%; mp 190-192° C.; $^1$H-NMR (300.13 MHz, CDCl$_3$, 303K): 1.560 (61-1, d, J=6.8), 4.459 (2H, br s), 4.746 (2H, br s), 4.792 (1H, sept, J=6.8), 6.446 (1H, br s), 6.673 (1H, dd, J=1.2, J=7.9), 6.717 (1H, mt), 7.10 (1H, mt), 7.15 (1H, dd, J=7.7, 1.2), 7.682 (1H, s).

6-[(2-aminobenzyl)amino]-2-chloro-9-cyclopropylpurine

Yield 88%; mp 204-220° C.; $^1$H-NMR (300.13 MHz, CDCl$_3$, 303K): 1.68 (4H, mt), 3.61 (1H, mt), 4.22 (2H, br s), 5.90 (2H, br s), 6.61 (2H, mt), 6.75 (1H, d, J=7.7), 7.0 (1H, t, 7.7), 7.90 (1H, br s), 7.84 (1H, s).

6-[(2-aminobenzyl)amino]-2-chloro-9-(pent-3-yl)purine

Yield 90%; mp 172-183° C.; $^1$H-NMR (300.13 MHz, CDCl$_3$, 303K): 1.05 (6H, t, J=3.4), 1.75 (2H, mt), 1.87 (2H, mt), 4.11 (1H, m), 4.22 (2H, br s), 5.90 (2H, br s), 6.61 (2H, mt), 6.75 (1H, d, J=7.7), 7.00 (1H, t, J=7.7), 7.91 (1H, br s), 8.89 (1H, s).

6-[(2-aminobenzyl)amino]-2-chloro-9-cyclopentylpurine

Yield 89%; mp 164-176° C.; $^1$H-NMR (300.13 MHz, CDCl$_3$, 303K): 1.80-1.90 (2H, mt), 1.93-2.10 (4H, mt), 2.25-2.40 (2H, mt), 4.459 (2H, br s), 4.746 (2H, br s), 4.99 (1H, pent, J=7.0), 6.446 (1H, br s), 6.673 (1H, dd, J=1.2, J=7.9), 6.717 (1H, mt), 7.10 (1H, mt), 7.15 (1H, dd, J=7.7, 1.2), 7.682 (1H, s).

6-[(2-aminobenzyl)amino]-2-chloro-9-cyclohexylpurine

Yield 89%; mp 165-174° C.; $^1$H-NMR (300.13 MHz, CDCl$_3$, 303K): 1.29 (2H, mt), 1.49 (2H, mt), 1.73 (2H, mt), 1.91 (2H, mt), 2.06 (2H, mt), 4.22 (2H, br s), 5.38 (1H, mt), 5.93 (2H, br s), 6.62 (2H, mt), 6.74 (1H, d, J=7.7), 7.02 (1H, t, J=7.7), 7.91 (1H, br s), 8.52 (1H, s).

6-[(2-aminobenzyl)amino]-2-chloro-9-benzylpurine

Yield 94%; mp 200-211° C.; $^1$H-NMR (300.13 MHz, CDCl$_3$, 303K): 4.21 (2H, br s), 5.91 (2H, br s), 6.60 (2H, m), 6.74 (1H, d, J=7.7), 7.02 (4H, mt), 7.14 (2H, dd, J=7.5, 1.2), 7.90 (1H, br s), 8.49 (1H, s).

Example 2

Preparation of 2-alkylamino-9-alkyl-6-[(2-amino-R$_n$-benzyl)amino]purines

6-[(2-amino-R$_n$-benzyl)amino]-2-chloro-9-alkylpurine (1 mmol), appropriate reactive amine (3 mmol) and diisopropylethylamine (2 mmol) were heated (the temperature and incubation period is specified for each below-listed substance) in N-methylpyrrolidone (5 mL, sealed ampule). The reaction mixture was then partitioned between water and CHCl$_3$ (1:1, v/v). Column chromatography (silica gel, chloroform/methanol) afforded pure product.

N-6-(2-aminobenzyl)-N-2-heptyl-9-isopropyl-9H-purin-2,6-diamine

Reaction conditions: 155° C., 2 h. Liquid chromatography 1% MeOH in CHCl$_3$; crystallization from abs. Et$_2$O; mp 65-72° C. $^1$H-NMR, δ ppm: 0.90 (31-1, t, J=6.8, C$^{25}$H), 1.31 (4H, m, C$^{20,21}$H), 1.38 (2H, m, C$^{22}$H), 1.54 (6H, d, J=6.8, C$^{17,18}$H), 1.64 (2H, m, C$^{24}$H), 2.39 (2H, t, J=8.2, C$^{23}$H), 3.44 (2H, q, J=6.8, C$^{19}$H), 4.65 (1H, sep, J=6.8, C$^{16}$H), 4.70 (2H, bs, N$^{11}$H), 4.78 (2H, d, J=5.9, C$^9$H), 5.40 (1H, bs, N$^2$H), 6.34 (1H, bs, N$^6$H), 6.65 (1H, dd, J=7.7, 1.1, C$^{12}$H), 6.71 (1H, tt, J=7.7, 1.3, C$^{14}$H), 7.10 (1H, tt, J=7.7, 1.5, C$^{13}$H), 7.14 (1H, dd, J=7.7, 1.3, C$^{15}$H), 7.44 (1H, s, C$^8$H). $^{13}$H-NMR, δ ppm: 14.74 (C25), 23.18 (C16,17), 23.30 (C24), 27.71 (C22), 29.78 (C21), 30.43 (C23), 32.47 (C20), 42.61 (C19), 42.81 (C9), 47.27 (C16), 114.48 (C5), 116.52 (C12), 118.76 (C14), 123.11 (C10), 129.75 (C13), 131.21 (C15), 135.63 (C8), 146.24 (C11), 151.07 (C4), 154.58 (C6), 158.69 (C2).

(RS)-1-({6-[(2-aminobenzyl)amino]-9-isopropyl-9-H-purin-2-yl}amino)propan-2-ol Reaction conditions: 155° C., 2 h. Liquid chromatography 1.5% MeOH in CHCl$_3$; crystallization from abs. CHCl$_3$; mp 175-179° C. $^1$H-NMR, δ ppm: 1.26 (3H, d, J=6.4, C$^{21}$H), 1.55 (6H, d, J=6.8, C$^{17,18}$H), 3.41 (1H, m, C$^{19}$H$_a$), 3.55 (1H, m, C$^{19}$H$_b$), 4.07 (1H, quiqui, J=6.8, 2.6, C$^{20}$H), 4.60 (1H, bs, O$^{20}$H), 4.64 (1H, sep, J=6.8, C$^{16}$H), 4.68 (2H, bs, N$^{11}$H), 4.79 (2H, bs, C$^9$H), 6.08 (1H, bs, N$^2$H), 6.60 (1H, bs, N$^6$H), 6.68 (1H, dd, J=7.8, 1.1, C$^{12}$H), 6.74 (1H, tt, J=7.5, 1.1, C$^{14}$H), 7.12 (1H, tt, J=7.7, 1.5, C$^{13}$H), 7.18 (1H, dd, J=7.7, 1.3, C$^{15}$H), 7.53 (1H, s, C$^8$H). $^{13}$C-NMR, δ ppm: 21.54 (C21), 23.16 (C17,18), 43.09 (C9), 47.70 (C16), 50.57 (C19), 69.17 (20), 114.42 (C5), 117.00 (C12), 119.29 (C14), 122.76 (C10), 129.93 (C13), 131.16 (C15), 136.02 (C8), 145.79 (C11), 150.20 (C4), 154.06 (C6), 158.68 (C2).

(R)-1-({6-(2-aminobenzyl)aminal-9-isopropyl-9-H-purin-2-yl}amino)propan-2-ol Reaction conditions: 155° C., 2 h. Liquid chromatography 1.5% MeOH in CHCl$_3$; crystallization from abs. CHCl$_3$; mp 169-175° C. $^1$H-NMR, δ ppm: 1.26 (3H, d, J=6.7, C$^{21}$H), 1.55 (6H, d, J=6.8, C$^{17,18}$H), 3.41 (1H, m, C$^{19}$H$_a$), 3.55 (1H, m, C$^{19}$H$_b$), 4.07 (1H, quiqui, J=6.8, 2.6, C$^{20}$H), 4.60 (1H, bs, O$^{20}$H), 4.64 (1H, sep, J=6.8, C$^{16}$H), 4.68 (2H, bs, N$^{11}$H), 4.79

(2H, bs, C$^9$H), 6.08 (1H, bs, N$^2$H), 6.60 (1H, bs, N$^6$H), 6.68 (1H, dd, J=7.8, 1.1, C$^{12}$H), 6.74 (1H, tt, J=7.5, 1.1, C$^{14}$H), 7.12 (1H, tt, J=7.7, 1.5, C$^{13}$H), 7.18 (1H, dd, J=7.7, 1.3, C$^{15}$H), 7.53 (1H, s, C$^8$H). $^{13}$C-NMR, δ ppm: 21.54 (C21), 23.16 (C17,18), 43.09 (C9), 47.70 (C16), 50.57 (C19), 69.17 (20), 114.42 (C5), 117.00 (C12), 119.29 (C14), 122.76 (C10), 129.93 (C13), 131.16 (C15), 136.02 (C8), 145.79 (C11), 150.20 (C4), 154.06 (C6), 158.68 (C2).

(RS)-2-({6-[(2-aminobenzyl)amino]-9-isopropyl-9-H-purin-2-yl}amino)butan-1-ol

Reaction conditions: 160° C., 6 h. Liquid chromatography 1.5% MeOH in CHCl$_3$; crystallization from abs. CHCl$_3$/abs. Et$_2$O; mp 152-156° C. $^1$H-NMR, δ ppm: 1.04 (3H, t, J=7.3, C$^{22}$H), 1.53 (6H, d, J=6.8, C$^{17,18}$H), 1.63 (2H, m, C$^{21}$H), 3.66 (1H, m, C$^{20}$H$_a$), 3.83 (1H, dd, J=11.0, 2.6, C$^{20}$H$_b$), 3.96 (1H, qui, J=6.8, C$^{19}$H), 4.58 (2H, bs, N$^{11}$H), 4.58 (1H, bs, O$^{20}$H), 4.59 (1H, sep, J=6.8, C$^{16}$H), 4.73 (2H, bs, C$^9$H), 5.33 (1H, bs, N$^2$H), 6.47 (1H, bs, N$^6$H), 6.65 (1H, dd, J=7.6, 1.1, C$^{12}$H), 6.71 (1H, tt, J=7.7, 1.3, C$^{14}$H), 7.10 (1H, tt, J=7.7, 1.5, C$^{13}$H), 7.14 (1H, dd, J=7.7, 1.3, C$^{15}$H), 7.44 (1H, s, C$^8$H). $^{13}$C-NMR, δ ppm: 11.55 (C22), 23.12 (C17), 23.18 (C18), 25.57 (C21), 42.72 (C9), 47.40 (C16), 56.88 (C19), 68.22 (C20), 114.91 (C5), 116.62 (C12), 118.90 (C14), 123.04 (C10), 129.76 (C13), 131.15 (C15), 135.66 (C8), 146.09 (C11), 150.59 (C4), 154.87 (C6), 159.54 (C2).

(R)-2-({6-[(2-aminobenzyl)amino]-9-isopropyl-9-H-purin-2-yl}amino)butan-1-ol

Reaction conditions: 160° C., 6 h. Liquid chromatography 1.5% MeOH in CHCl$_3$; crystallization from abs. CHCl$_3$/abs. Et$_2$O; mp 149-151° C. $^1$H-NMR, δ ppm: 1.04 (3H, t, J=7.3, C$^{22}$H), 1.53 (6H, d, J=6.8, C$^{17,18}$H), 1.62 (2H, m, C$^{21}$H), 3.66 (1H, m, C$^{20}$H$_a$), 3.83 (1H, dd, J=11.0, 2.6, C$^{20}$H$_b$), 3.96 (1H, qui, J=6.8, C$^{19}$H), 4.56 (2H, bs, N$^{11}$H), 4.58 (1H, bs, O$^{20}$H), 4.59 (1H, sep, J=6.8, C$^{16}$H), 4.73 (2H, bs, C$^9$H), 5.33 (1H, bs, N$^2$H), 6.46 (1H, bs, N$^6$H), 6.65 (1H, dd, J=7.7, 1.1, C$^{12}$H), 6.71 (1H, tt, J=7.7, 1.3, C$^{14}$H), 7.10 (1H, tt, J=7.7, 1.5, C$^{13}$H), 7.14 (1H, dd, J=7.7, 1.3, C$^{15}$H), 7.44 (1H, s, C$^8$H). $^{13}$C-NMR, δ ppm: 11.55 (C22), 23.12 (C17), 23.18 (C18), 25.57 (C21), 42.72 (C9), 47.40 (C16), 56.88 (C19), 68.22 (C20), 114.91 (C5), 116.62 (C12), 118.90 (C14), 123.04 (C10), 129.76 (C13), 131.15 (C15), 135.66 (C8), 146.09 (C11), 150.59 (C4), 154.87 (C6), 159.54 (C2).

(E/Z)—N-2-(2-aminocyclohexyl)-N-6-(2-aminobenzyl)-9-isopropyl-9H-purin-2,6-diamine Reaction conditions: 160° C., 4 h. Liquid chromatography stepwise 1, 2, 3, 4, 5% MeOH in CHCl$_3$, 0.1% of concentrated NH$_4$OH; amorphous substance. $^1$H-NMR, δ ppm: 1.27 (3H, m, C$^{22}$H, C$^{24}$H) 1.51 (6H, d, J=6.8, C$^{17,18}$H), 1.70 (3H, m, C$^{23}$H, C$^{21}$H$_b$), 2.08 (1H, d, J=10.8, C$^{24}$H$_b$), 2.16 (1H, d, J=10.0, C$^{21}$H$_b$), 3.70 (1H, m, C$^{20}$H), 4.27 (1H, m, C$^{19}$H), 4.64 (1H, sep, J=6.8, C$^{16}$H), 4.72 (2H, bs, C$^9$H), 4.76 (2H, bs, N$^{11}$H), 4.82 (2H, bs, N$^{20}$H), 5.13 (1H, bs, N$^2$H), 6.17 (1H, bs, N$^6$H), 6.65 (1H, dd, J=7.7, 1.1, C$^{12}$H), 6.68 (1H, tt, J=7.7, 1.3, C$^{14}$H), 7.06 (1H, tt, J=7.7, 1.5, C$^{13}$H), 7.15 (1H, dd, J=7.7, 1.5, C$^{15}$H), 7.48 (1H, s, C$^8$H). $^{13}$C-NMR, δ ppm: 22.74 (C22), 23.33 (C17,18), 25.42 (C24), 29.72 (C21), 33.39 (C23), 42.40 (C9), 46.94 (C16), 52.11 (C19), 57.14 (C20), 115.33 (C5), 116.56 (C14), 118.76 (C14), 123.67 (C10), 129.47 (C13), 130.99 (C15), 135.51 (C8), 145.09 (C11), 151.62 (C4), 155.40 (C6), 159.96 (C2).

(Z)—N-2-(2-aminocyclohexyl)-N-6-(2-aminobenzyl)-9-isopropyl-9H-purin-2,6-diamine Reaction conditions: 160° C., 4 h. Liquid chromatography stepwise 1, 2, 3, 4, 5% MeOH in CHCl$_3$, 0.1% of concentrated NH$_4$OH; amorphous substance. $^1$H-NMR, δ ppm: 1.27 (3H, m, C$^{22}$H, C$^{24}$H$_a$), 1.51 (6H, d, J=6.7, C$^{17,18}$H), 1.70 (3H, m, C$^{23}$H, C$^{21}$H$_b$), 2.08 (1H, d, J=10.6, C$^{24}$H$_b$), 2.16 (1H, d, J=10.1, C$^{21}$H$_b$), 3.70 (1H, m, C$^{20}$H), 4.27 (1H, m, C$^{19}$H), 4.64 (1H, sep, J=6.8, C$^{16}$H), 4.72 (2H, bs, C$^9$H), 4.76 (2H, bs, N$^{11}$H), 4.83 (2H, bs, N$^{20}$H), 5.13 (1H, bs, N$^2$H), 6.17 (114, bs, N$^6$H), 6.65 (1H, dd, J=7.7, 1.1, C$^{12}$H), 6.68 (1H, tt, J=7.7, 1.3, C$^{14}$H), 7.06 (1H, tt, J=7.7, 1.5, C$^{13}$H), 7.15 (1H, dd, J=7.7, 1.5, C$^{15}$H), 7.48 (1H, s, C$^8$H).

(E)-N-2-(2-aminocyclohexyl)-N-6-(2-aminobenzyl)-9-isopropyl-9H-purin-2,6-diamine Reaction conditions: 160° C., 4 h. Liquid chromatography stepwise 1, 2, 3, 4, 5% MeOH in CHCl$_3$, 0.1% of concentrated NH$_4$OH; amorphous substance. $^1$H-NMR, δ ppm: 1.27 (3H, m, C$^{22}$H, C$^{24}$H$_a$), 1.51 (614, d, J=6.8, C$^{17,18}$H), 1.70 (3H, m, C$^{23}$H, C$^{21}$H$_b$), 2.08 (1H, d, J=10.7, C$^{24}$H$_b$), 2.16 (1H, d, J=10.2, C$^{21}$H$_b$), 3.70 (1H, m, C$^{20}$H), 4.27 (1H, m, C$^{19}$H), 4.64 (114, sep, J=6.8, C$^{16}$H), 4.72 (2H, bs, C$^9$H), 4.76 (214, bs, N$^{11}$H), 4.83 (2H, bs, N$^{20}$H), 5.13 (1H, bs, N$^2$H), 6.17 (1H, bs, N$^6$H), 6.65 (1H, dd, J=7.7, 1.1, C$^{12}$H), 6.68 (1H, tt, J=7.7, 1.3, C$^{14}$H), 7.06 (1H, tt, J=7.7, 1.5, C$^{13}$H), 7.15 (1H, dd, J=7.7, 1.5, C$^{15}$H), 7.48 (1H, s, C$^8$H).

(E)-N-2-(4-aminocyclohexyl)-N-6-(2-aminobenzyl)-9-isopropyl-9H-purin-2,6-diamine Reaction conditions: 160° C., 4 h. Liquid chromatography stepwise 1, 2, 3, 4, 5, 6% MeOH in CHCl$_3$, 0.1% of concentrated NH$_4$OH; amorphous substance. $^1$H-NMR, δ ppm: 0.85 (2H, m, C$^{21,23}$H$_{aa}$), 1.27 (2H, m, C$^{21,23}$H$_{bb}$), 1.54 (6H, d, J=6.8, C$^{17,18}$H), 2.08 (2H, d, J=11.0, C$^{20,24}$H$_{aa}$), 2.22 (2H, d, J=11.0, C$^{20,24}$H$_{bb}$), 3.70 (1H, m, C$^{19}$H), 3.84 (1H, m, C$^{22}$H), 4.64 (1H, sep, J=6.8, C$^{16}$H), 4.68 (2H, bs, N$^{11}$H), 4.71 (2H, s, C$^9$H), 4.72 (2H, bs, N$^2$H), 5.85 (1H, bs, N$^2$H), 6.30 (1H, bs, N$^6$H), 6.67 (1H, dd, J=7.7, 1.1, C$^{12}$H), 6.71 (1H, tt, J=7.7, 1.3, C$^{14}$H), 7.10 (1H, tt, J=7.7, 1.5, C$^{13}$H), 7.15 (1H, dd, J=7.7, 1.3, C$^{15}$H), 7.48 (1H, s, C$^8$H). $^{13}$C-NMR, δ ppm: 23.31 (C16,17), 30.41 (C20,24), 33.84 (C21,23), 42.35 (C9), 46.93 (C16), 51.02 (C22), 64.36 (C19), 115.10 (C5), 116.41 (C12), 118.76 (C14), 123.63 (C10), 129.62 (C13), 131.15 (C15), 135.31 (C8), 146.21 (C11), 151.85 (C4), 155.48 (C6), 159.43 (C2).

N-2-(4-methoxybenzyl)-N-6-(2-aminobenzyl)-9-isopropyl-9H-purin-2,6-diamine

Reaction conditions: 160° C., 1 h. Liquid chromatography stepwise 1, 2, % MeOH in CHCl$_3$; crystallization from abs. Et$_2$O; mp 90-112° C. $^1$H-NMR, δ ppm: 1.53 (6H, d, J=6.8, C$^{17,18}$H), 3.81 (3H, s, C$^{25}$H), 4.61 (2H, d, J=5.7, N$^{11}$H), 4.65 (1H, sep, J=6.8, C$^{16}$H), 4.74 (2H, d, J=5.9, C$^9$H), 5.54 (1H, bs, N$^2$H), 6.31 (1H, t, J=7.1, N$^6$H), 6.62 (1H, dd, J=7.7, 1.5, C$^{12}$H), 6.69 (1H, tt, J=7.7, 1.5, C$^{14}$H), 6.88 (2H, dd, J=8.6, 2.0, C$^{20,24}$H), 7.09 (1H, tt, J=7.7, 1.5, C$^{13}$H), 7.11 (1H, dd, J=7.7, 1.5, C$^{15}$H), 7.33 (2H, dd, J=8.4, 1.7, C$^{21,23}$H), 7.42 (114μs, C$^8$H). $^{13}$C-NMR, δ ppm: 23.18 (C17,18), 42.62 (C9), 47.24 (C16), 55.98 (C25), 114.56 (C20,24), 114.93 (C5), 116.41 (C12), 118.64 (C14), 123.22 (C10), 129.54 (C21,23), 129.68 (C13), 131.20 (C15), 132.62 (C19), 135.64 (C8), 146.27 (C11), 151.25 (C4), 154.93 (C6), 158.96 (C2), 159.43 (C22).

(E)-4-({6-[(2-aminobenzyl)amino]-9-isopropyl-9-H-purin-2-yl}amino)cyclohexanol

Reaction conditions: 160° C., 20 h. Liquid chromatography 1.5% MeOH in CHCl$_3$; amorphous substance. $^1$H-NMR, δ ppm: 0.85 (2H, m, C$^{21,23}$H$_{aa}$), 1.39 (2H, m, C$^{21,23}$H$_{bb}$), 1.56 (6H, d, J=6.8, C$^{17,18}$H), 2.04 (2H, m, C$^{20,24}$H$_{aa}$), 2.17 (2H, m, C$^{20,24}$H$_{bb}$), 3.70 (1H, m, C$^{19}$H), 3.80 (1H, bs, O$^{22}$H), 3.85 (1H, m, C$^{22}$H), 4.65 (2H, bs, N$^{11}$H), 4.66 (1H, sep, J=6.8, C$^{16}$H), 4.82 (2H, bs, C$^9$H), 5.76 (1H, bs, N$^2$H), 6.56 (1H, bs, N$^6$H), 6.67 (1H, dd, J=7.9, 1.1, C$^{12}$H), 6.73 (1H, tt, J=7.5, 1.1, C$^{14}$H), 7.12 (1H, t, J=7.7, 1.5, C$^{13}$H), 7.17 (1H, dd, J=7.7, 1.5, C$^{15}$H), 7.50 (1H, s, C$^8$H). $^{13}$C-NMR, δ ppm: 23.20 (C17, 18), 31.22 (C21,23), 34.54 (C20,24), 43.24 (C9), 47.65 (C16), 50.42 (C22), 70.48 (C19), 114.12 (C5), 116.77 (C12), 119.06 (C14), 122.64 (C10), 129.92 (C13), 131.09 (C15), 136.00 (C8), 146.09 (C11), 151.49 (C4), 156.63 (C6), 158.82 (C2).

TABLE 1

Compounds prepared by the method of Example 2

| No | SUBSTITUENTS ON PURINE | | | CHN ANALYSES | MS (ZMD)- ANALYSES | |
|---|---|---|---|---|---|---|
| | C2 | C6 | N9 | [%] | [M − H]$^−$ a) | [M + H]$^+$ b) |
| 1 | 2-aminocyclohexylamino | (2-aminobenzyl)amino | methyl | 62.3/7.1/30.6 | 365.5 | 367.5 |
| 2 | 4-aminocyclohexylamino | (2-aminobenzyl)amino | methyl | 62.3/7.1/30.6 | 365.5 | 367.5 |
| 3 | 4-hxydroxycyclohexylamino | (2-aminobenzyl)amino | methyl | 62.1/6.9/26.7 | 366.5 | 368.5 |
| 4 | 2-hydroxypropylamino | (2-aminobenzyl)amino | methyl | 58.7/6.5/29.9 | 326.3 | 328.3 |
| 5 | (1-hydroxymethyl)propylamino | (2-aminobenzyl)amino | methyl | 59.8/6.8/28.7 | 340.4 | 342.4 |
| 6 | heptylamino | (2-aminobenzyl)amino | methyl | 65.4/7.9/26.7 | 366.5 | 368.5 |
| 7 | (1-hydroxymethyl-2-methyl)propylamino | (2-aminobenzyl)amino | methyl | 60.8/7.1/27.6 | 354.4 | 356.4 |
| 8 | 2-hydroxy-2-methylpropylamino | (2-aminobenzyl)amino | methyl | 59.8/6.8/28.7 | 340.4 | 342.4 |
| 9 | 2-hydroxy-1,2-dimethyl-propylamino | (2-aminobenzyl)amino | methyl | 60.8/7.1/27.6 | 354.4 | 356.5 |
| 10 | 3-hydroxy-3-methylbutylamino | (2-aminobenzyl)amino | methyl | 60.8/7.1/27.6 | 354.4 | 356.5 |
| 11 | 3-hydroxy-1,3-dimethyl-butylamino | (2-aminobenzyl)amino | methyl | 61.8/7.4/26.5 | 368.5 | 370.5 |
| 12 | 3-hydroxy-2,3-dimethylbutylamino | (2-aminobenzyl)amino | methyl | 61.8/7.4/26.5 | 368.5 | 370.5 |
| 13 | 2-hydroxy-1-ethyl-2-methylpropylamino | (2-aminobenzyl)amino | methyl | 61.8/7.4/26.5 | 368.5 | 370.5 |
| 14 | 2-hydroxy-1-ethylpropylamino | (2-aminobenzyl)amino | methyl | 60.8/7.1/27.6 | 354.4 | 356.4 |
| 15 | 2-aminocyclohexylamino | (2-amino-5-chlorobenzyl)amino | methyl | 56.9/6.3/27.9 | 399.9 | 401.9 |
| 16 | 4-aminocyclohexylamino | (2-amino-5-chloro benzyl)amino | methyl | 56.9/6.3/27.9 | 399.9 | 401.9 |
| 17 | (1-hydroxymethyl)propylamino | (2-amino-5-chloro benzyl)amino | methyl | 54.3/5.9/26.1 | 374.8 | 376.8 |
| 18 | (1-hydroxymethyl-2-methyl)propylamino | (2-amino-5-chloro benzyl)amino | methyl | 55.4/6.2/25.1 | 388.9 | 390.9 |
| 19 | 3-hydroxy-1,3-dimethyl-butylamino | (2-amino-5-chloro benzyl)amino | methyl | 56.5/6.5/24.3 | 402.9 | 404.9 |
| 20 | 2-hydroxy-1-ethylpropylamino | (2-amino-5-chloro benzyl)amino | methyl | 55.4/6.2/25.1 | 388.9 | 390.9 |
| 21 | 2-aminocyclohexylamino | (2-amino-5-fluorobenzyl)amino | methyl | 59.4/6.6/29.1 | 383.4 | 385.4 |
| 22 | 4-aminocyclohexylamino | (2-amino-5-fluoro benzyl)amino | methyl | 59.4/6.6/29.1 | 383.4 | 385.4 |
| 23 | (1-hydroxymethyl)propylamino | (2-amino-5-fluorobenzyl)amino | methyl | 56.8/6.2/27.3 | 358.4 | 360.4 |
| 24 | 2-aminocyclohexylamino | (2-amino-3-chlorobenzyl)amino | methyl | 56.9/6.3/27.9 | 399.9 | 401.9 |
| 25 | 4-aminocyclohexylamino | (2-amino-3-chloro benzyl)amino | methyl | 56.9/6.3/27.9 | 399.9 | 401.9 |
| 26 | 2-hydroxy-1-ethylpropylamino | (2-amino-3-chlorobenzyl)amino | methyl | 55.4/6.2/25.1 | 388.9 | 390.9 |
| 27 | 2-aminocyclohexylamino | (2-amino-3-methylbenzyl)amino | methyl | 63.1/7.4/29.4 | 379.5 | 381.5 |
| 28 | 4-aminocyclohexylamino | (2-amino-3-methylbenzyl)amino | methyl | 63.1/7.4/29.4 | 379.5 | 381.5 |
| 29 | 2-hydroxypropylamino | (2-amino-3-methylbenzyl)amino | methyl | 59.8/6.8/28.7 | 340.4 | 342.4 |
| 30 | 2-hydroxy-1-ethyl-2-methylpropylamino | (2-amino-4-methylbenzyl)amino | methyl | 62.6/7.6/25.6 | 382.5 | 384.5 |
| 31 | 4-aminocyclohexylamino | (2-amino-5-methylbenzyl)amino | methyl | 63.1/7.4/29.4 | 379.5 | 381.5 |
| 32 | (1-hydroxymethyl)propylamino | (2-amino-5-methylbenzyl)amino | methyl | 60.8/7.1/27.6 | 354.4 | 356.4 |
| 33 | 3-hydroxy-3-methylbutylamino | (2-amino-5-methylbenzyl)amino | methyl | 61.8/7.4/26.5 | 368.5 | 370.5 |
| 34 | 2-aminocyclohexylamino | (2,3-diaminobenzyl)amino | methyl | 59.8/7.1/33.0 | 380.5 | 382.5 |
| 35 | 4-aminocyclohexylamino | (2,3-diaminobenzyl)amino | methyl | 59.8/7.1/33.0 | 380.5 | 382.5 |
| 36 | (1-hydroxymethyl)propylamino | (2,3-diaminobenzyl)amino | methyl | 57.3/6.8/31.4 | 355.4 | 357.4 |
| 37 | (1-hydroxymethyl-2-methyl)propylamino | (2,3-diaminobenzyl)amino | methyl | 58.4/7.1/30.2 | 369.4 | 371.4 |
| 38 | 2-hydroxy-1-ethylpropylamino | (2,3-diaminobenzyl)amino | methyl | 58.4/7.1/30.2 | 369.4 | 371.4 |
| 39 | 2-aminocyclohexylamino | (2,4-diaminobenzyl)amino | methyl | 59.8/7.1/33.0 | 380.5 | 382.5 |
| 40 | (1-hydroxymethyl)propylamino | (2,4-diaminobenzyl)amino | methyl | 57.3/6.831.4 | 355.4 | 357.4 |
| 41 | (1-hydroxymethyl-2-methyl)propylamino | (2,4-diaminobenzyl)amino | methyl | 58.4/7.1/30.2 | 369.4 | 371.4 |
| 42 | 2-aminocyclohexylamino | (2,5-diaminobenzyl)amino | methyl | 59.8/7.1/33.0 | 380.5 | 382.5 |
| 43 | 4-hydroxycyclohexylamino | (2,5-diaminobenzyl)amino | methyl | 59.7/6.8/29.3 | 381.5 | 383.5 |
| 44 | (1-hydroxymethyl)propylamino | (2,5-diaminobenzyl)amino | methyl | 57.3/6.8/31.4 | 355.4 | 357.4 |

TABLE 1-continued

Compounds prepared by the method of Example 2

| No | SUBSTITUENTS ON PURINE C2 | C6 | N9 | CHN ANALYSES [%] | MS (ZMD)-ANALYSES [M − H]⁻ a) | [M + H]⁺ b) |
|---|---|---|---|---|---|---|
| 45 | 2-aminocyclohexylamino | (2-amino-3-methoxybenzyl)amino | methyl | 60.6/7.1/28.3 | 395.5 | 397.5 |
| 46 | 4-aminocyclohexylamino | (2-amino-3-methoxybenzyl)amino | methyl | 60.6/7.1/28.3 | 395.5 | 397.5 |
| 47 | 2-hydroxypropylamino | (2-amino-3-methoxybenzyl)amino | methyl | 57.1/6.5/27.4 | 356.4 | 358.4 |
| 48 | (1-hydroxymethyl)propylamino | (2-amino-3-methoxybenzyl)amino | methyl | 58.2/6.8/26.4 | 370.4 | 372.4 |
| 50 | 2-aminocyclohexylamino | (2-amino-4-methoxybenzyl)amino | methyl | 60.6/7.1/28.3 | 395.5 | 397.5 |
| 51 | 4-hydroxycyclohexylamino | (2-amino-4-methoxybenzyl)amino | methyl | 60.4/6.9/24.7 | 396.5 | 398.5 |
| 52 | (1-hydroxymethyl)propylamino | (2-amino-4-methoxybenzyl)amino | methyl | 58.2/6.8/26.4 | 370.4 | 372.4 |
| 53 | (1-hydroxymethyl-2-methyl)propylamino | (2-amino-4-methoxybenzyl)amino | methyl | 59.2/7.1/25.4 | 384.5 | 386.5 |
| 54 | 2-hydroxy-1-ethylpropylamino | (2-amino-4-methoxybenzyl)amino | methyl | 59.2/7.1/25.4 | 384.5 | 386.5 |
| 55 | 2-aminocyclohexylamino | (2-amino-5-methoxybenzyl)amino | methyl | 60.6/7.1/28.2 | 395.5 | 397.5 |
| 56 | 4-hydroxycyclohexylamino | (2-amino-5-methoxybenzyl)amino | methyl | 60.4/6.8/24.6 | 396.5 | 398.5 |
| 57 | (1-hydroxymethyl)propylamino | (2-amino-5-methoxybenzyl)amino | methyl | 58.2/6.8/26.4 | 370.4 | 372.4 | a) solution: MeOH p.a. + HCOOH
b) solution: MeOH p.a. + H₂O + NH₃

TABLE 2

Compounds prepared by the method of Example 2

| No | SUBSTITUENTS ON PURINE C2 | C6 | N9 | CHN ANALYSES [%] | MS (ZMD)-ANALYSES [M − H]⁻ a) | [M + H]⁺ b) |
|---|---|---|---|---|---|---|
| 58 | 2-aminocyclohexylamino | (2-aminobenzyl)amino | ethyl | 63.1/7.4/29.4 | 379.5 | 381.5 |
| 59 | 4-aminocyclohexylamino | (2-aminobenzyl)amino | ethyl | 63.1/7.4/29.4 | 379.5 | 381.5 |
| 60 | 4-hydroxycyclohexylamino | (2-aminobenzyl)amino | ethyl | 63.0/7.1/25.7 | 380.5 | 382.5 |
| 61 | 2-hydroxypropylamino | (2-aminobenzyl)amino | ethyl | 59.8/6.8/28.7 | 340.4 | 342.4 |
| 62 | (1-hydroxymethyl)propylamino | (2-aminobenzyl)amino | ethyl | 60.8/7.1/27.6 | 354.4 | 356.4 |
| 63 | heptylamino | (2-aminobenzyl)amino | ethyl | 66.1/8.2/25.7 | 380.5 | 382.5 |
| 64 | (1-hydroxymethyl-2-methyl)propylamino | (2-aminobenzyl)amino | ethyl | 61.8/7.4/26.5 | 368.5 | 370.5 |
| 65 | 2-hydroxy-2-methylpropylamino | (2-aminobenzyl)amino | ethyl | 60.8/7.1/27.6 | 354.5 | 356.5 |
| 66 | 2-hydroxy-1,2-dimethylpropylamino | (2-aminobenzyl)amino | ethyl | 61.8/7.4/26.5 | 368.5 | 370.5 |
| 67 | 3-hydroxy-3-methylbutylamino | (2-aminobenzyl)amino | ethyl | 61.8/7.4/26.5 | 368.5 | 370.5 |
| 68 | 3-hydroxy-1,3-dimethylbutylamino | (2-aminobenzyl)amino | ethyl | 62.6/7.6/25.6 | 382.5 | 384.5 |
| 69 | 3-hydroxy-2,3-dimethylbutylamino | (2-aminobenzyl)amino | ethyl | 62.6/7.6/25.6 | 382.5 | 384.5 |
| 70 | 2-hydroxy-1-ethyl-2-methylpropylamino | (2-aminobenzyl)amino | ethyl | 62.6/7.6/25.6 | 382.5 | 384.5 |
| 71 | 2-hydroxy-1-ethylpropylamino | (2-aminobenzyl)amino | ethyl | 61.1/7.4/26.5 | 368.5 | 370.5 |
| 72 | 2-aminocyclohexylamino | (2-amino-5-chlorobenzyl)amino | ethyl | 57.9/6.5/27.0 | 413.9 | 415.9 |
| 73 | 4-aminocyclohexylamino | (2-amino-5-chlorobenzyl)amino | ethyl | 57.9/6.5/27.0 | 413.9 | 415.9 |
| 74 | 2-hydroxypropylamino | (2-amino-5-chlorobenzyl)amino | ethyl | 54.3/5.9/26.1 | 374.8 | 376.8 |
| 75 | (1-hydroxymethyl)propylamino | (2-amino-5-chlorobenzyl)amino | ethyl | 55.4/6.2/25.1 | 388.9 | 390.9 |
| 76 | 4-aminocyclohexylamino | (2-amino-5-fluorobenzyl)amino | ethyl | 60.3/6.8/28.1 | 397.5 | 399.5 |
| 77 | (1-hydroxymethyl)propylamino | (2-amino-5-fluorobenzyl)amino | ethyl | 57.9/6.5/26.2 | 372.4 | 374.4 |

TABLE 2-continued

Compounds prepared by the method of Example 2

| No | SUBSTITUENTS ON PURINE | | | CHN ANALYSES [%] | MS (ZMD)-ANALYSES | |
|---|---|---|---|---|---|---|
| | C2 | C6 | N9 | | [M − H]⁻ a) | [M + H]⁺ b) |
| 78 | 2-aminocyclohexylamine | (2-amino-3-chlorobenzyl)amino | ethyl | 57.9/6.6/27.0 | 413.9 | 415.9 |
| 79 | 4-aminocyclohexylamine | (2-amino-3-chlorobenzyl)amino | ethyl | 57.9/6.6/27.0 | 413.9 | 415.9 |
| 90 | 2-hydroxy-1-ethylpropylamino | (2-amino-3-chlorobenzyl)amino | ethyl | 56.5/6.5/24.3 | 402.9 | 404.9 |
| 81 | 2-aminocyclohexylamino | (2-amino-3-methylbenzyl)amino | ethyl | 63.9/7.6/28.4 | 393.5 | 395.5 |
| 82 | 4-aminocyclohexylamino | (2-amino-3-methylbenzyl)amino | ethyl | 63.9/7.6/28.4 | 393.5 | 395.5 |
| 83 | 2-hydroxy-1-ethyl-2-methylpropylamino | (2-amino-4-methylbenzyl)amino | ethyl | 62.6/7.6/25.6 | 382.5 | 384.5 |
| 84 | 2-aminocyclohexylamino | (2-amino-4-methylbenzyl)amino | ethyl | 63.9/7.6/28.4 | 393.5 | 395.5 |
| 85 | 4-aminocyclohexylamino | (2-amino-5-methylbenzyl)amino | ethyl | 63.9/7.6/28.4 | 393.5 | 395.5 |
| 86 | (1-hydroxymethyl)propylamino | (2-amino-5-methylbenzyl)amino | ethyl | 61.8/7.4/26.5 | 368.5 | 370.5 |
| 87 | 3-hydroxy-3-methylbutylamino | (2-amino-5-methylbenzyl)amino | ethyl | 62.6/7.6/25.6 | 382.5 | 384.5 |
| 88 | 4-aminocyclohexylamino | (2,3-diaminobenzyl)amino | ethyl | 60.7/7.4/31.9 | 394.5 | 396.5 |
| 89 | (1-hydroxymethyl)propylamino | (2,3-diaminobenzyl)amino | ethyl | 58.4/7.1/30.2 | 369.5 | 371.5 |
| 90 | 2-aminocyclohexylamino | (2,4-diaminobenzyl)amino | ethyl | 60.7/7.4/31.9 | 394.5 | 396.5 |
| 91 | (1-hydroxymethyl)propylamino | (2,4-diaminobenzyl)amino | ethyl | 58.4/7.1/30.2 | 369.5 | 371.5 |
| 92 | 2-aminocyclohexylamino | (2,5-diaminobenzyl)amino | ethyl | 60.7/7.4/31.9 | 394.5 | 396.5 |
| 93 | 4-hydroxycyclohexylamino | (2,5-diaminobenzyl)amino | ethyl | 60.6/7.1/28.3 | 395.5 | 397.5 |
| 94 | (1-hydroxymethyl)propylamino | (2,5-diaminobenzyl)amino | ethyl | 58.4/7.1/30.2 | 369.5 | 371.5 |
| 95 | 4-aminocyclohexylamino | (2-amino-3-methoxybenzyl)amino | ethyl | 61.4/7.4/27.3 | 409.5 | 411.5 |
| 96 | 2-hydroxypropylamino | (2-amino-3-methoxybenzyl)amino | ethyl | 58.2/6.8/26.4 | 370.4 | 372.4 |
| 97 | 2-aminocyclohexylamino | (2-amino-4-methoxybenzyl)amino | ethyl | 61.4/7.4/27.3 | 409.5 | 411.5 |
| 98 | (1-hydroxymethyl)propylamino | (2-amino-4-methoxybenzyl)amino | ethyl | 59.2/7.1/25.4 | 384.5 | 386.5 |
| 99 | 4-hydroxycyclohexylamino | (2-amino-5-methoxybenzyl)amino | ethyl | 61.3/7.1/23.8 | 410.5 | 412.5 |
| 100 | (1-hydroxymethyl)propylamino | (2-amino-5-methoxybenzyl)amino | ethyl | 59.2/7.1/25.4 | 384.5 | 386.5 | a) solution: MeOH p.a. + HCOOH
b) solution: MeOH p.a. + H₂O + NH₃

TABLE 3

Compounds prepared by the method of Example 2

| No | SUBSTITUENTS ON PURINE | | | CHN ANALYSES [%] | MS (ZMD)-ANALYSES | |
|---|---|---|---|---|---|---|
| | C2 | C6 | N9 | | [M − H]⁻ a) | [M + H]⁺ b) |
| 101 | 2-aminocyclohexylamino | (2-aminobenzyl)amino | isopropyl | 63.9/7.7/28.4 | 393.5 | 395.5 |
| 102 | 4-aminocyclohexylamino | (2-aminobenzyl)amino | isopropyl | 63.9/7.7/28.4 | 393.5 | 395.5 |
| 103 | 4-hydroxycyclohexylamino | (2-aminobenzyl)amino | isopropyl | 63.8/7.4/24.8 | 394.5 | 396.5 |
| 104 | 2-hydroxypropylamino | (2-aminobenzyl)amino | isopropyl | 60.8/7.1/27.6 | 354.4 | 356.4 |
| 105 | (1-hydroxymethyl)propylamino | (2-aminobenzyl)amino | isopropyl | 61.8/7.4/26.5 | 368.5 | 370.5 |
| 106 | heptylamino | (2-aminobenzyl)amino | isopropyl | 66.8/8.4/24.8 | 394.5 | 396.5 |
| 107 | (1-hydroxymethyl-2-methyl)propylamino | (2-aminobenzyl)amino | isopropyl | 62.6/7.6/25.6 | 382.5 | 384.5 |
| 108 | 2-hydroxy-2-methylpropylamino | (2-aminobenzyl)amino | isopropyl | 61.8/7.4/26.5 | 368.5 | 370.5 |
| 109 | 2-hydroxy-1,2-dimethylpropylamino | (2-aminobenzyl)amino | isopropyl | 62.6/7.6/25.6 | 382.5 | 384.5 |

TABLE 3-continued

Compounds prepared by the method of Example 2

| No | SUBSTITUENTS ON PURINE C2 | C6 | N9 | CHN ANALYSES [%] | MS (ZMD)-ANALYSES [M − H]− a) | [M + H]+ b) |
|---|---|---|---|---|---|---|
| 110 | 3-hydroxy-3-methylbutylamino | (2-aminobenzyl)amino | isopropyl | 62.6/7.6/25.6 | 382.5 | 384.5 |
| 111 | 3-hydroxy-1,3-dimethylbutylamino | (2-aminobenzyl)amino | isopropyl | 63.4/7.9/24.6 | 396.5 | 398.5 |
| 112 | 3-hydroxy-2,3-dimethylbutylamino | (2-aminobenzyl)amino | isopropyl | 63.4/7.9/24.6 | 396.5 | 398.5 |
| 113 | 2-hydroxy-1-ethyl-2-methylpropylamino | (2-aminobenzyl)amino | isopropyl | 63.4/7.9/24.6 | 396.5 | 398.5 |
| 114 | 2-hydroxy-1-ethylpropylamino | (2-aminobenzyl)amino | isopropyl | 62.6/7.6/25.6 | 382.5 | 384.5 |
| 115 | 2-aminocyclohexylamino | (2-amino-5-chlorobenzyl)amino | isopropyl | 63.4/7.9/24.6 | 396.5 | 398.5 |
| 116 | 4-aminocyclohexylamino | (2-amino-5-chlorobenzyl)amino | isopropyl | 63.4/7.9/24.6 | 396.5 | 398.5 |
| 117 | 2-hydroxypropylamino | (2-amino-5-chlorobenzyl)amino | isopropyl | 55.5/6.2/25.1 | 388.9 | 390.9 |
| 118 | (1-hydroxymethyl)propylamino | (2-amino-5-chlorobenzyl)amino | isopropyl | 56.5/6.5/24.3 | 402.9 | 404.9 |
| 119 | (1-hydroxymethyl-2-methyl)propylamino | (2-amino-5-chlorobenzyl)amino | isopropyl | 57.5/6.8/23.5 | 416.9 | 418.9 |
| 120 | 2-hydroxy-2-methylpropylamino | (2-amino-5-chlorobenzyl)amino | isopropyl | 56.5/6.5/24.3 | 402.9 | 404.9 |
| 121 | 2-hydroxy-1,2-dimethylpropylamino | (2-amino-5-chlorobenzyl)amino | isopropyl | 57.5/6.8/23.5 | 416.9 | 418.9 |
| 122 | 3-hydroxy-3-methylbutylamino | (2-amino-5-chlorobenzyl)amino | isopropyl | 57.5/6.8/23.5 | 416.9 | 418.9 |
| 123 | 4-hydroxy-4-methylpent-2-yllamino | (2-amino-5-chlorobenzyl)amino | isopropyl | 58.4/7.0/22.7 | 431.0 | 433.0 |
| 124 | 2-hydroxy-1-ethylpropylamino | (2-amino-5-chlorobenzyl)amino | isopropyl | 57.5/6.8/23.5 | 416.9 | 418.9 |
| 125 | 2-aminocyclohexylamino | (2-amino-5-fluorobenzyl)amino | isopropyl | 61.1/7.1/27.2 | 411.5 | 413.5 |
| 126 | 4-aminocyclohexylamino | (2-amino-5-fluorobenzyl)amino | isopropyl | 61.1/7.1/27.2 | 411.5 | 413.5 |
| 127 | 2-hydroxypropylamino | (2-amino-5-fluorobenzyl)amino | isopropyl | 57.9/6.5/26.2 | 372.4 | 374.4 |
| 128 | (1-hydroxymethyl)propylamino | (2-amino-5-fluorobenzyl)amino | isopropyl | 58.9/6.8/25.3 | 386.5 | 388.5 |
| 129 | 2-hydroxy-1-ethyl-2-methylpropylamino | (2-amino-5-fluorobenzyl)amino | isopropyl | 60.7/7.3/23.6 | 414.5 | 416.5 |
| 130 | 2-hydroxy-1-ethylpropylamino | (2-amino-5-fluorobenzyl)amino | isopropyl | 59.8/7.0/24.4 | 400.5 | 402.5 |
| 131 | 2-aminocyclohexylamino | (2-amino-3-chlorobenzyl)amino | isopropyl | 63.4/7.9/24.6 | 396.5 | 398.5 |
| 132 | 4-aminocyclohexylamino | (2-amino-3-chlorobenzyl)amino | isopropyl | 63.4/7.9/24.6 | 396.5 | 398.5 |
| 133 | (1-hydroxymethyl)propylamino | (2-amino-3-chlorobenzyl)amino | isopropyl | 56.5/6.5/24.3 | 402.9 | 404.9 |
| 134 | (1-hydroxymethyl-2-methyl)propylamino | (2-amino-3-chlorobenzyl)amino | isopropyl | 57.5/6.8/23.5 | 416.9 | 418.9 |
| 135 | 2-hydroxy-2-methylpropylamino | (2-amino-3-chlorobenzyl)amino | isopropyl | 56.5/6.5/24.3 | 402.9 | 404.9 |
| 136 | 2-hydroxy-1-ethylpropylamino | (2-amino-3-chlorobenzyl)amino | isopropyl | 57.5/6.8/23.5 | 416.9 | 418.9 |
| 137 | 2-aminocyclohexylamino | (2-amino-3-methylbenzyl)amino | isopropyl | 64.7/7.9/27.4 | 407.5 | 409.5 |
| 138 | 4-aminocyclohexylamino | (2-amino-3-methylbenzyl)amino | isopropyl | 64.7/7.9/27.4 | 407.5 | 409.5 |
| 139 | 2-hydroxypropylamino | (2-amino-3-methylbenzyl)amino | isopropyl | 61.7/7.4/26.5 | 368.5 | 370.5 |
| 140 | (1-hydroxymethyl)propylamino | (2-amino-3-methylbenzyl)amino | isopropyl | 62.6/7.6/25.6 | 382.5 | 384.5 |
| 141 | 3-hydroxy-3-methylbutylamino | (2-amino-3-methylbenzyl)amino | isopropyl | 63.4/7.9/24.6 | 396.5 | 398.5 |
| 142 | 2-hydroxy-1-ethyl-2-methylpropylamino | (2-amino-4-methylbenzyl)amino | isopropyl | 64.2/8.1/23.8 | 410.5 | 412.5 |
| 143 | 2-hydroxy-1-ethylpropylamino | (2-amino-4-methylbenzyl)amino | isopropyl | 63.4/7.9/24.6 | 396.5 | 398.5 |
| 144 | 2-aminocyclohexylamino | (2-amino-4-methylbenzyl)amino | isopropyl | 64.7/7.9/27.4 | 407.5 | 409.5 |
| 145 | 4-aminocyclohexylamino | (2-amino-5-methylbenzyl)amino | isopropyl | 64.7/7.9/27.4 | 407.5 | 409.5 |

TABLE 3-continued

Compounds prepared by the method of Example 2

| No | SUBSTITUENTS ON PURINE | | | CHN ANALYSES [%] | MS (ZMD)- ANALYSES | |
|---|---|---|---|---|---|---|
| | C2 | C6 | N9 | | [M − H]⁻ a) | [M + H]⁺ b) |
| 146 | (1-hydroxymethyl)propylamino | (2-amino-5-methylbenzyl)amino | isopropyl | 62.6/7.6/25.6 | 382.5 | 384.5 |
| 147 | 3-hydroxy-3-methylbutylamino | (2-amino-5-methylbenzyl)amino | isopropyl | 63.4/7.9/24.6 | 396.5 | 398.5 |
| 148 | 2-hydroxy-1-ethyl-2-methylpropylamino | (2-amino-5-methylbenzyl)amino | isopropyl | 64.2/8.1/23.8 | 410.5 | 412.5 |
| 149 | 2-hydroxy-1-ethylpropylamino | (2-amino-5-methylbenzyl)amino | isopropyl | 63.4/7.9/24.6 | 396.5 | 398.5 |
| 150 | 2-aminocyclohexylamino | (2,3-diaminobenzyl)amino | isopropyl | 61.6/7.6/30.8 | 408.5 | 410.5 |
| 151 | 4-aminocyclohexylamino | (2,3-diaminobenzyl)amino | isopropyl | 61.6/7.6/30.8 | 408.5 | 410.5 |
| 152 | (1-hydroxymethyl)propylamino | (2,3-diaminobenzyl)amino | isopropyl | 59.3/7.3/29.1 | 383.5 | 385.5 |
| 153 | (1-hydroxymethyl-2-methyl)propylamino | (2,3-diaminobenzyl)amino | isopropyl | 60.3/7.6/28.1 | 397.5 | 399.5 |
| 154 | 3-hydroxy-1,3-dimethylbutylamino | (2,3-diaminobenzyl)amino | isopropyl | 61.1/7.8/27.1 | 411.5 | 413.5 |
| 155 | 2-hydroxy-1-ethyl-2-methylpropylamino | (2,3-diaminobenzyl)amino | isopropyl | 61.1/7.8/27.1 | 411.5 | 413.5 |
| 156 | 2-hydroxy-1-ethylpropylamino | (2,3-diaminobenzyl)amino | isopropyl | 60.3/7.6/28.1 | 397.5 | 399.5 |
| 157 | 2-aminocyclohexylamino | (2,4-diaminobenzyl)amino | isopropyl | 61.6/7.6/30.8 | 408.5 | 410.5 |
| 158 | (1-hydroxymethyl)propylamino | (2,4-diaminobenzyl)amino | isopropyl | 59.3/7.3/29.1 | 383.5 | 385.5 |
| 159 | (1-hydroxymethyl-2-methyl)propylamino | (2,4-diaminobenzyl)amino | isopropyl | 60.3/7.6/28.1 | 397.5 | 399.5 |
| 160 | 2-aminocyclohexylamino | (2,5-diaminobenzyl)amino | isopropyl | 61.6/7.6/30.8 | 408.5 | 410.5 |
| 161 | 4-hydroxycyclohexylamino | (2,5-diaminobenzyl)amino | isopropyl | 61.4/7.4/27.3 | 409.5 | 411.5 |
| 162 | (1-hydroxymethyl)propylamino | (2,5-diaminobenzyl)amino | isopropyl | 59.3/7.3/29.1 | 383.5 | 385.5 |
| 163 | (1-hydroxymethyl-2-methyl)propylamino | (2,5-diaminobenzyl)amino | isopropyl | 60.3/7.6/28.1 | 397.5 | 399.5 |
| 164 | 2-aminocyclohexylamino | (2-amino-3-methoxybenzyl)amino | isopropyl | 62.2/7.6/26.4 | 423.5 | 425.5 |
| 165 | 4-aminocyclohexylamino | (2-amino-3-methoxybenzyl)amino | isopropyl | 62.2/7.6/26.4 | 423.5 | 425.5 |
| 166 | 2-hydroxypropylamino | (2-amino-3-methoxylbenzyl)amino | isopropyl | 59.2/7.1/25.4 | 384.5 | 386.5 |
| 167 | (1-hydroxymethyl)propylamino | (2-amino-3-methoxybenzyl)amino | isopropyl | 60.1/7.3/24.5 | 398.5 | 400.5 |
| 168 | (1-hydroxymethyl-2-methyl)propylamino | (2-amino-3-methoxybenzyl)amino | isopropyl | 61.0/7.6/23.7 | 412.5 | 414.5 |
| 169 | 2-hydroxy-2-methylpropylamino | (2-amino-3-methoxybenzyl)amino | isopropyl | 60.1/7.3/24.5 | 398.5 | 400.5 |
| 170 | 2-hydroxy-1,2-dimethylpropylamino | (2-amino-3-methoxybenzyl)amino | isopropyl | 61.0/7.6/23.7 | 412.5 | 414.5 |
| 171 | 3-hydroxy-3-methylbutylamino | (2-amino-3-methoxybenzyl)amino | isopropyl | 61.0/7.6/23.7 | 412.5 | 414.5 |
| 172 | 3-hydroxy-1,3-dimethylbutylamino | (2-amino-3-methoxybenzyl)amino | isopropyl | 61.8/7.8/22.9 | 426.5 | 428.5 |
| 173 | 2-hydroxy-1-ethylpropylamino | (2-amino-3-methoxybenzyl)amino | isopropyl | 61.0/7.6/23.7 | 412.5 | 414.5 |
| 174 | 2-aminocyclohexylamino | (2-amino-4-methoxybenzyl)amino | isopropyl | 62.2/7.6/26.4 | 423.5 | 425.5 |
| 175 | 4-hydroxycyclohexylamino | (2-amino-4-methoxybenzyl)amino | isopropyl | 62.1/7.3/23.0 | 424.5 | 426.5 |
| 176 | (1-hydroxymethyl)propylamino | (2-amino-4-methoxybenzyl)amino | isopropyl | 60.1/7.3/24.5 | 398.5 | 400.5 |
| 177 | (1-hydroxymethyl-2-methyl)propylamino | (2-amino-4-methoxybenzyl)amino | isopropyl | 61.0/7.6/23.7 | 412.5 | 414.5 |
| 178 | 2-hydroxy-2-methylpropylamino | (2-amino-4-methoxybenzyl)amino | isopropyl | 60.1/7.3/24.5 | 398.5 | 400.5 |
| 179 | 2-aminocyclohexylamino | (2-amino-4-methoxybenzyl)amino | isopropyl | 61.0/7.6/23.7 | 412.5 | 414.5 |
| 180 | (1-hydroxymethyl)propylamino | (2-amino-5-methoxybenzyl)amino | isopropyl | 62.2/7.6/26.4 | 423.5 | 425.5 |
| 181 | (1-hydroxymethyl-2-methyl)propylamino | (2-amino-5-methoxybenzyl)amino | isopropyl | 62.1/7.3/23.0 | 424.5 | 426.5 |
| 182 | (1-hydroxymethyl)propylamino | (2-amino-5-methoxybenzyl)amino | isopropyl | 60.1/7.3/24.5 | 398.5 | 400.5 |
| 183 | (1-hydroxymethyl)propylamino | (2-amino-5-methoxybenzyl)amino | isopropyl | 61.0/7.6/23.7 | 412.5 | 414.5 | a) solution: MeOH p.a. + HCOOH
b) solution: MeOH p.a. + H$_2$O + NH$_3$

TABLE 4

Compounds prepared by the method of Example 2

| No | SUBSTITUENTS ON PURINE | | | CHN ANALYSES [%] | MS (ZMD)-ANALYSES | |
|---|---|---|---|---|---|---|
| | C2 | C6 | N9 | | [M − H]− a) | [M + H]+ b) |
| 184 | 4-aminocyclohexylamino | (2-aminobenzyl)amino | propyl | 63.9/7.7/28.4 | 393.5 | 395.5 |
| 185 | 4-hydroxycyclohexylamino | (2-aminobenzyl)amino | propyl | 63.8/7.4/24.8 | 394.5 | 396.5 |
| 186 | 2-hydroxypropylamino | (2-aminobenzyl)amino | propyl | 60.8/7.1/27.6 | 354.4 | 356.4 |
| 187 | (1-hydroxymethyl)propylamino | (2-aminobenzyl)amino | propyl | 61.8/7.4/26.5 | 368.5 | 370.5 |
| 188 | heptylamino | (2-aminobenzyl)amino | propyl | 66.8/8.4/24.8 | 394.5 | 396.5 |
| 189 | (1-hydroxymethyl-2-methyl)propylamino | (2-aminobenzyl)amino | propyl | 62.6/7.6/25.6 | 382.5 | 384.5 |
| 190 | 2-hydroxy-2-methylpropylamino | (2-aminobenzyl)amino | propyl | 61.8/7.4/26.5 | 368.5 | 370.5 |
| 191 | 2-hydroxy-1,2-dimethylpropylamino | (2-aminobenzyl)amino | propyl | 62.6/7.6/25.6 | 382.5 | 384.5 |
| 192 | 3-hydroxy-3-methylbutylamino | (2-aminobenzyl)amino | propyl | 62.6/7.6/25.6 | 382.5 | 384.5 |
| 193 | 3-hydroxy-1,3-dimethylbutylamino | (2-aminobenzyl)amino | propyl | 63.4/7.9/24.6 | 396.5 | 398.5 | a) solution: MeOH p.a. + HCOOH
b) solution: MeOH p.a. + H$_2$O + NH$_3$

TABLE 5

Compounds prepared by the method of Example 2

| No | SUBSTITUENTS ON PURINE | | | CHN ANALYSES [%] | MS (ZMD)-ANALYSES | |
|---|---|---|---|---|---|---|
| | C2 | C6 | N9 | | [M − H]− a) | [M + H]+ b) |
| 194 | 2-aminocyclohexylamino | (2-aminobenzyl)amino | cyclohexyl | 66.3/7.9/25.8 | 433.6 | 435.6 |
| 195 | 4-aminocyclohexylamino | (2-aminobenzyl)amino | cyclohexyl | 66.3/7.9/25.8 | 433.6 | 435.6 |
| 196 | 4-hydroxycyclohexylamino | (2-aminobenzyl)amino | cyclohexyl | 66.2/7.6/22.5 | 434.6 | 436.6 |
| 197 | 2-hydroxypropylamino | (2-aminobenzyl)amino | cyclohexyl | 63.8/7.4/24.8 | 394.5 | 396.5 |
| 198 | (1-hydroxymethyl)propylamino | (2-aminobenzyl)amino | cyclohexyl | 64.5/7.6/23.9 | 408.5 | 410.5 |
| 199 | heptylamino | (2-aminobenzyl)amino | cyclohexyl | 68.9/8.6/22.5 | 434.6 | 436.6 |
| 200 | (1-hydroxymethyl-2-methyl)propylamino | (2-aminobenzyl)amino | cyclohexyl | 65.2/7.8/23.1 | 422.6 | 424.6 |
| 201 | 2-hydroxy-2-methylpropylamino | (2-aminobenzyl)amino | cyclohexyl | 64.5/7.6/23.9 | 408.5 | 410.5 |
| 202 | 2-hydroxy-1,2-dimethylpropylamino | (2-aminobenzyl)amino | cyclohexyl | 65.2/7.8/23.1 | 422.6 | 424.6 |
| 203 | 3-hydroxy-3-methylbutylamino | (2-aminobenzyl)amino | cyclohexyl | 65.2/7.8/23.1 | 422.6 | 424.6 |
| 204 | 3-hydroxy-1,3-dimethylbutylamino | (2-aminobenzyl)amino | cyclohexyl | 65.9/8.1/22.4 | 436.6 | 438.6 |
| 205 | 3-hydroxy-2,3-dimethylbutylamino | (2-aminobenzyl)amino | cyclohexyl | 65.9/8.1/22.4 | 436.6 | 438.6 |
| 206 | 2-hydroxy-1-ethyl-2-methylpropylamino | (2-aminobenzyl)amino | cyclohexyl | 65.9/8.1/22.4 | 436.6 | 438.6 |
| 207 | 2-hydroxy-1-ethylpropylamino | (2-aminobenzyl)amino | cyclohexyl | 65.2/7.8/23.1 | 422.6 | 424.6 |
| 208 | 4-aminocyclohexylamino | (2-amino-5-chloro benzyl)amino | cyclohexyl | 61.5/7.1/23.9 | 468.0 | 470.0 |
| 209 | (1-hydroxymethyl)propylamino | (2-amino-5-chloro benzyl)amino | cyclohexyl | 59.5/6.8/22.1 | 443.0 | 445.0 |
| 210 | (1-hydroxymethyl-2-methyl)propylamino | (2-amino-5-chloro benzyl)amino | cyclohexyl | 60.3/7.0/21.4 | 457.0 | 459.0 |
| 211 | 2-aminocyclohexylamino | (2-amino-5-fluorobenzyl)amino | cyclohexyl | 63.7/7.3/24.8 | 451.6 | 453.6 |
| 212 | 4-aminocyclohexylamino | (2-amino-5-fluoro benzyl)amino | cyclohexyl | 63.7/7.3/24.8 | 451.6 | 453.6 |
| 213 | (1-hydroxymethyl)propylamino | (2-amino-5-fluorobenzyl)amino | cyclohexyl | 61.8/7.1/22.9 | 426.5 | 428.5 |
| 214 | 4-aminocyclohexylamino | (2-amino-3-chlorobenzyl)amino | cyclohexyl | 61.5/7.1/23.9 | 468.0 | 470.0 |
| 215 | 4-aminocyclohexylamino | (2-amino-3-methylbenzyl)amino | cyclohexyl | 66.9/8.1/25.0 | 447.6 | 449.6 |
| 216 | 2-hydroxy-1-ethyl-2-methylpropylamino | (2-amino-4-methylbenzyl)amino | cyclohexyl | 66.5/8.3/21.7 | 450.6 | 452.6 |
| 217 | 4-aminocyclohexylamino | (2-amino-5-methylbenzyl)amino | cyclohexyl | 66.9/8.1/25.0 | 447.6 | 449.6 |

TABLE 5-continued

Compounds prepared by the method of Example 2

| No | SUBSTITUENTS ON PURINE | | | CHN ANALYSES [%] | MS (ZMD)-ANALYSES | |
|---|---|---|---|---|---|---|
| | C2 | C6 | N9 | | [M − H]⁻ a) | [M + H]⁺ b) |
| 218 | (1-hydroxymethyl)propylamino | (2-amino-5-methylbenzyl)amino | cyclohexyl | 65.2/7.8/23.1 | 422.6 | 424.6 |
| 219 | 3-hydroxy-3-methylbutylamino | (2-amino-5-methylbenzyl)amino | cyclohexyl | 65.9/8.1/22.4 | 436.6 | 438.6 |
| 220 | 2-aminocyclohexylamino | (2,3-diaminobenzyl)amino | cyclohexyl | 64.1/7.8/28.0 | 448.6 | 450.6 |
| 221 | 4-aminocyclohexylamino | (2,3-diaminobenzyl)amino | cyclohexyl | 64.1/7.8/28.0 | 448.6 | 450.6 |
| 222 | (1-hydroxymethyl)propylamino | (2,4-diaminobenzyl)amino | cyclohexyl | 62.2/7.6/26.4 | 423.5 | 425.5 |
| 223 | (1-hydroxymethyl-2-methyl)propylamino | (2,4-diaminobenzyl)amino | cyclohexyl | 63.0/7.8/25.5 | 437.6 | 439.6 |
| 224 | 2-aminocyclohexylamino | (2,5-diaminobenzyl)amino | cyclohexyl | 64.1/7.8/28.0 | 448.6 | 450.6 |
| 225 | 2-hydroxypropylamino | (2-amino-3-methoxybenzyl)amino | cyclohexyl | 62.1/7.3/23.0 | 424.5 | 426.5 |
| 226 | (1-hydroxymethyl)propylamino | (2-amino-3-methoxybenzyl)amino | cyclohexyl | 62.8/7.6/22.3 | 438.6 | 440.6 |
| 227 | 2-hydroxy-1-ethylpropylamino | (2-amino-3-methoxybenzyl)amino | cyclohexyl | 63.5/7.8/21.6 | 452.6 | 454.6 |
| 228 | 2-aminocyclohexylamino | (2-amino-4-methoxybenzyl)amino | cyclohexyl | 64.6/7.8/24.1 | 463.6 | 465.6 |
| 229 | (1-hydroxymethyl)propylamino | (2-amino-5-methoxybenzyl)amino | cyclohexyl | 62.8/7.6/22.3 | 438.6 | 440.6 | a) solution: MeOH p.a. + HCOOH
b) solution: MeOH p.a. + H₂O + NH₃

TABLE 6

Compounds prepared by the method of Example 2

| No | SUBSTITUENTS ON PURINE | | | CHN ANALYSES [%] | MS (ZMD)-ANALYSES | |
|---|---|---|---|---|---|---|
| | C2 | C6 | N9 | | [M − H]⁻ a) | [M + H]⁺ b) |
| 230 | 2-aminocyclohexylamino | (2-aminobenzyl)amino | benzyl | 67.8/6.8/25.3 | 441.6 | 443.6 |
| 231 | 4-aminocyclohexylamino | (2-aminobenzyl)amino | benzyl | 67.8/6.8/25.3 | 441.6 | 443.6 |
| 232 | 4-hydroxycyclohexylamino | (2-aminobenzyl)amino | benzyl | 67.7/6.6/22.1 | 442.6 | 444.6 |
| 233 | 2-hydroxypropylamino | (2-aminobenzyl)amino | benzyl | 65.5/6.2/24.3 | 402.5 | 404.5 |
| 234 | (1-hydroxymethyl)propylamino | (2-aminobenzyl)amino | benzyl | 66.2/6.5/23.5 | 416.5 | 418.5 |
| 235 | heptylamino | (2-aminobenzyl)amino | benzyl | 70.4/7.5/22.1 | 442.6 | 444.6 |
| 236 | (1-hydroxymethyl-2-methyl)propylamino | (2-aminobenzyl)amino | benzyl | 66.8/6.8/22.7 | 430.5 | 432.5 |
| 237 | 2-hydroxy-2-methylpropylamino | (2-aminobenzyl)amino | benzyl | 66.2/6.5/23.5 | 416.5 | 418.5 |
| 238 | 2-hydroxy-1,2-dimethylpropylamino | (2-aminobenzyl)amino | benzyl | 66.8/6.8/22.7 | 430.5 | 432.5 |
| 239 | 3-hydroxy-3-methylbutylamino | (2-aminobenzyl)amino | benzyl | 66.8/6.8/22.7 | 430.5 | 432.5 |
| 240 | 3-hydroxy-1,3-dimethylbutylamino | (2-aminobenzyl)amino | benzyl | 67.4/7.0/22.0 | 444.6 | 446.6 |
| 241 | 3-hydroxy-2,3-dimethylbutylamino | (2-aminobenzyl)amino | benzyl | 67.4/7.0/22.0 | 444.6 | 446.6 |
| 242 | 2-hydroxy-1-ethyl-2-methylpropylamino | (2-aminobenzyl)amino | benzyl | 67.4/7.0/22.0 | 444.6 | 446.6 |
| 243 | 2-hydroxy-1-ethylpropylamino | (2-aminobenzyl)amino | benzyl | 66.8/6.8/22.7 | 430.5 | 432.5 |
| 244 | 2-aminocyclohexylamino | (2-amino-5-chlorobenzyl)amino | benzyl | 62.9/6.1/23.5 | 476.0 | 478.0 |
| 245 | 4-aminocyclohexylamino | (2-amino-5-chlorobenzyl)amino | benzyl | 62.9/6.1/23.5 | 476.0 | 478.0 |
| 246 | 2-hydroxypropylamino | (2-amino-5-chlorobenzyl)amino | benzyl | 60.3/5.5/22.4 | 436.9 | 438.9 |
| 247 | (1-hydroxymethyl)propylamino | (2-amino-5-chlorobenzyl)amino | benzyl | 61.1/5.8/21.7 | 451.0 | 453.0 |
| 248 | (1-hydroxymethyl-2-methyl)propylamino | (2-amino-5-chlorobenzyl)amino | benzyl | 61.9/6.1/21.0 | 465.0 | 467.0 |
| 249 | 3-hydroxy-1,3-dimethylbutylamino | (2-amino-5-chlorobenzyl)amino | benzyl | 62.6/6.3/20.4 | 479.0 | 481.0 |
| 250 | 2-hydroxy-1-ethylpropylamino | (2-amino-5-chlorobenzyl)amino | benzyl | 61.9/6.1/21.0 | 465.0 | 467.0 |
| 251 | 2-aminocyclohexylamino | (2-amino-5-fluorobenzyl)amino | benzyl | 65.2/6.3/24.3 | 459.6 | 461.6 |

TABLE 6-continued

Compounds prepared by the method of Example 2

| | SUBSTITUENTS ON PURINE | | | CHN ANALYSES | MS (ZMD)- ANALYSES | |
|---|---|---|---|---|---|---|
| No | C2 | C6 | N9 | [%] | [M − H]⁻ a) | [M + H]⁺ b) |
| 252 | 4-aminocyclohexylamino | (2-amino-5-fluoro benzyl)amino | benzyl | 65.2/6.3/24.3 | 459.6 | 461.6 |
| 253 | (1-hydroxymethyl)propylamino | (2-amino-5-fluorobenzyl)amino | benzyl | 63.4/6.0/22.5 | 434.5 | 436.5 |
| 254 | 2-aminocyclohexylamino | (2-amino-3-chlorobenzyl)amino | benzyl | 62.9/6.1/23.5 | 476.0 | 478.0 |
| 255 | 4-aminocyclohexylamino | (2-amino-3-chloro benzyl)amino | benzyl | 62.9/6.1/23.5 | 476.0 | 478.0 |
| 256 | 2-hydroxy-1-ethylpropylamino | (2-amino-3-chlorobenzyl)amino | benzyl | 61.9/6.1/21.0 | 465.0 | 467.0 |
| 257 | 2-aminocyclohexylamino | (2-amino-3-methylbenzyl)amino | benzyl | 68.4/7.1/24.5 | 455.6 | 457.6 |
| 258 | 4-aminocyclohexylamino | (2-amino-3-methylbenzyl)amino | benzyl | 68.4/7.1/24.5 | 455.6 | 457.6 |
| 259 | 2-hydroxy-1-ethyl-2-methylpropylamino | (2-amino-4-methylbenzyl)amino | benzyl | 67.9/7.2/21.3 | 458.6 | 460.6 |
| 260 | 2-aminocyclohexylamino | (2-amino-5-methylbenzyl)amino | benzyl | 68.4/7.1/24.5 | 455.6 | 457.6 |
| 261 | 4-aminocyclohexylamino | (2-amino-5-methylbenzyl)amino | benzyl | 68.4/7.1/24.5 | 455.6 | 457.6 |
| 262 | (1-hydroxymethyl)propylamino | (2-amino-5-methylbenzyl)amino | benzyl | 66.8/6.8/22.7 | 430.5 | 432.5 |
| 263 | 3-hydroxy-3-methylbutylamino | (2-amino-5-methylbenzyl)amino | benzyl | 67.4/7.0/22.0 | 444.6 | 446.6 |
| 264 | 2-aminocyclohexylamino | (2,3-diaminobenzyl)amino | benzyl | 65.6/6.8/27.5 | 456.6 | 458.6 |
| 265 | 4-aminocyclohexylamino | (2,3-diaminobenzyl)amino | benzyl | 65.6/6.8/27.5 | 456.6 | 458.6 |
| 266 | (1-hydroxymethyl)propylamino | (2,3-diaminobenzyl)amino | benzyl | 63.9/6.5/25.9 | 431.5 | 433.5 |
| 267 | (1-hydroxymethyl-2-methyl)propylamino | (2,3-diaminobenzyl)amino | benzyl | 64.5/6.8/25.1 | 445.6 | 447.6 |
| 268 | 2-hydroxy-1-ethylpropylamino | (2,3-diaminobenzyl)amino | benzyl | 64.5/6.8/25.1 | 445.6 | 447.6 |
| 269 | 2-aminocyclohexylamino | (2,4-diaminobenzyl)amino | benzyl | 65.6/6.8/27.5 | 456.6 | 458.6 |
| 270 | (1-hydroxymethyl)propylamino | (2,4-diaminobenzyl)amino | benzyl | 63.9/6.5/25.9 | 431.5 | 433.5 |
| 271 | (1-hydroxymethyl-2-methyl)propylamino | (2,4-diaminobenzyl)amino | benzyl | 64.5/6.8/25.1 | 445.6 | 447.6 |
| 272 | 2-aminocyclohexylamino | (2,5-diaminobenzyl)amino | benzyl | 65.6/6.8/27.5 | 456.6 | 458.6 |
| 273 | 4-hydroxycyclohexylamino | (2,5-diaminobenzyl)amino | benzyl | 65.5/6.6/24.4 | 457.6 | 459.6 |
| 274 | (1-hydroxymethyl)propylamino | (2,5-diaminobenzyl)amino | benzyl | 63.9/6.5/25.9 | 431.5 | 433.5 |
| 275 | 2-aminocyclohexylamino | (2-amino-3-methoxybenzyl)amino | benzyl | 66.1/6.8/23.7 | 471.6 | 473.6 |
| 276 | 4-aminocyclohexylamino | (2-amino-3-methoxybenzyl)amino | benzyl | 66.1/6.8/23.7 | 471.6 | 473.6 |
| 277 | (1-hydroxymethyl)propylamino | (2-amino-3-methoxybenzyl)amino | benzyl | 64.4/6.5/21.9 | 446.5 | 448.5 |
| 278 | 2-hydroxy-1-ethylpropylamino | (2-amino-3-methoxybenzyl)amino | benzyl | 65.1/6.8/21.2 | 460.6 | 462.6 |
| 279 | 2-aminocyclohexylamino | (2-amino-4-methoxybenzyl)amino | benzyl | 66.1/6.8/23.7 | 471.6 | 473.6 |
| 280 | 4-hydroxycyclohexylamino | (2-amino-4-methoxybenzyl)amino | benzyl | 65.9/6.6/20.7 | 472.6 | 474.6 |
| 281 | (1-hydroxymethyl)propylamino | (2-amino-4-methoxybenzyl)amino | benzyl | 64.4/6.5/21.9 | 446.5 | 448.5 |
| 282 | (1-hydroxymethyl-2-methyl)propylamino | (2-amino-4-methoxybenzyl)amino | benzyl | 65.7/6.7/20.6 | 474.6 | 476.6 |
| 283 | 2-hydroxy-1-ethylpropylamino | (2-amino-4-methoxybenzyl)amino | benzyl | 65.7/6.7/20.6 | 474.6 | 476.6 |
| 284 | 2-aminocyclohexylamino | (2-amino-5-methoxybenzyl)amino | benzyl | 66.1/6.8/23.7 | 471.6 | 473.6 |
| 285 | 2-hydroxypropylamino | (2-amino-5-methoxybenzyl)amino | benzyl | 63.7/6.3/22.6 | 432.5 | 434.5 |
| 286 | 4-hydroxycyclohexylamino | (2-amino-5-methoxybenzyl)amino | benzyl | 65.9/6.6/20.7 | 472.6 | 474.6 |
| 287 | (1-hydroxymethyl)propylamino | (2-amino-5-methoxybenzyl)amino | benzyl | 64.4/6.5/21.9 | 446.5 | 448.5 | a) solution: MeOH p.a. + HCOOH
b) solution: MeOH p.a. + $H_2O$ + $NH_3$

Example 3

CDK Inhibition Assays

Selected compounds were tested for CDK1/cyclin B, CDK2/cyclin E and CDK9/cyclin T inhibitory activity to determine the basic relationships between their structure and the inhibitory activity. CDK/cyclin complexes were produced in Sf9, insect cells co-infected with an appropriate baculoviral construct. The cells were harvested 70 hours post infection in lysis buffer (50 mM Tris 7.4 pH, 150 mM NaCl, 5 mM EDTA, 20 mM NaF, 1% Tween 20, protease inhibitors) for 30 min on ice and the soluble fraction was recovered by centrifugation at 14,000 g for 10 min. The protein extract was stored at −80° C. until use. The final point test system for kinase activity measurement was used to carry out experiments on the kinetics under linear conditions. The assay mixture contained 1 mg/ml histone (Sigma Type III-S), 15 µM ATP, 0.2 µCi [$\gamma$-$^{32}$P] ATP and the tested compound in the final volume of 20 µl, all in reaction buffer: 50 mM Hepes 7.4 pH, 10 mM MgCl$_2$, 5 mM EGTA, 10 mM 2-glycerolphosphate, 1 mM NaF, 1 mM DTT and protease inhibitors. After 10 min, the incubations were stopped by adding SDS sample buffer and the proteins were separated using 12.5% SDS-PAGE. The measurement of kinase inhibition employed the digital imaging analyzer BAS 1800. The kinase activity was expressed as a percentage of maximum activity and the IC$_{50}$ value was determined by graphic analysis. The kinase activity is expressed as a percentage of maximum activity, the respective inhibition constants are determined by graphic analysis from dose-response curves.

TABLE 7

Kinase inhibitory activity of selected novel compounds

| | SUBSTITUENTS ON PURINE | | | IC$_{50}$ (µM) | | |
|---|---|---|---|---|---|---|
| No | C2 | C6 | N9 | CDK1 | CDK2 | CDK9 |
| OC | 2-hydroxyethylamino | benzylamino | methyl | 7 | 4 | 5 |
| RO | (1-hydroxymethyl)propylamino | benzylamino | isopropyl | 2.7 | 0.84 | 0.72 |
| 105 | (1-hydroxymethyl)propylamino | (2-aminobenzyl)amino | isopropyl | 0.09 | 0.03 | 0.005 |
| 118 | (1-hydroxymethyl)propylamino | (2-amino-5-chlorobenzyl)amino | isopropyl | 0.08 | 0.01 | 0.002 |
| 128 | (1-hydroxymethyl)propylamino | (2-amino-5-fluorobenzyl)amino | isopropyl | 0.07 | 0.008 | 0.0009 |
| 182 | (1-hydroxymethyl)propylamino | (2-amino-5-methoxybenzyl)amino | isopropyl | 0.2 | 0.1 | 0.001 |
| 5 | (1-hydroxymethyl)propylamino | (2-aminobenzyl)amino | methyl | 0.09 | 0.03 | 0.004 |
| 62 | (1-hydroxymethyl)propylamino | (2-aminobenzyl)amino | ethyl | 0.07 | 0.01 | 0.0007 |
| 187 | (1-hydroxymethyl)propylamino | (2-aminobenzyl)amino | propyl | 0.2 | 0.1 | 0.0007 |
| 198 | (1-hydroxymethyl)propylamino | (2-aminobenzyl)amino | cyclohexyl | 0.4 | 0.1 | 0.03 |
| 209 | (1-hydroxymethyl)propylamino | (2-amino-5-chlorobenzyl)amino | cyclohexyl | 0.5 | 0.3 | 0.04 |
| 234 | (1-hydroxymethyl)propylamino | (2-aminobenzyl)amino | benzyl | 0.7 | 0.4 | 0.03 |
| 247 | (1-hydroxymethyl)propylamino | (2-amino-5-chlorobenzyl)amino | benzyl | 0.8 | 0.6 | 0.07 |
| A1140 | 2-aminocyclohexylamino | benzylamino | methyl | 2.3 | 2.7 | 2.5 |
| 1 | 2-aminocyclohexylamino | (2-aminobenzyl)amino | methyl | 1.1 | 0.8 | 0.05 |
| 115 | 2-aminocyclohexylamino | (2-amino-5-chlorobenzyl)amino | isopropyl | 0.3 | 0.1 | 0.009 |
| 125 | 2-aminocyclohexylamino | (2-amino-5-fluorobenzyl)amino | isopropyl | 0.4 | 0.1 | 0.008 |
| A1141 | 4-aminocyclohexylamino | benzylamino | methyl | 3.1 | 3.4 | 3.3 |
| 2 | 4-aminocyclohexylamino | (2-aminobenzyl)amino | methyl | 0.7 | 0.4 | 0.01 |
| 46 | 4-aminocyclohexylamino | (2-amino-3-methoxybenzyl)amino | methyl | 0.5 | 0.3 | 0.05 |
| 59 | 4-aminocyclohexylamino | (2-aminobenzyl)amino | ethyl | 0.6 | 0.2 | 0.04 |
| 184 | 4-aminocyclohexylamino | (2-aminobenzyl)amino | propyl | 0.4 | 0.2 | 0.0009 |
| A2141 | 4-aminocyclohexylamino | benzylamino | isopropyl | 0.4 | 0.5 | 0.7 |
| 102 | 4-aminocyclohexylamino | (2-aminobenzyl)amino | isopropyl | 0.1 | 0.08 | 0.004 |
| 116 | 4-aminocyclohexylamino | (2-amino-5-chlorobenzyl)amino | isopropyl | 0.08 | 0.04 | 0.005 |
| 138 | 4-aminocyclohexylamino | (2-amino-3-methylbenzyl)amino | isopropyl | 0.1 | 0.07 | 0.0006 |
| 161 | 4-aminocyclohexylamino | (2,5-diaminobenzyl)amino | isopropyl | 0.9 | 0.6 | 0.08 |
| 195 | 4-aminocyclohexylamino | (2-aminobenzyl)amino | cyclohexyl | 0.6 | 0.3 | 0.05 |
| 231 | 4-aminocyclohexylamino | (2-aminobenzyl)amino | benzyl | 0.8 | 0.5 | 0.05 |
| A2144 | 4-hydroxycyclohexylamino | benzylamino | isopropyl | 0.6 | 0.8 | 0.6 |
| 103 | 4-hydroxycyclohexylamino | (2-aminobenzyl)amino | isopropyl | 0.2 | 0.15 | 0.003 |
| A216 | 2-hydroxypropylamino | benzylamino | isopropyl | 1.2 | 1.5 | 1.3 |
| 104 | 2-hydroxypropylamino | (2-aminobenzyl)amino | isopropyl | 0.09 | 0.03 | 0.006 |
| 166 | 2-hydroxypropylamino | (2-amino-3-methoxylbenzyl)amino | isopropyl | 0.4 | 0.1 | 0.002 |
| A218 | heptylamino | benzylamino | isopropyl | 160 | 165 | 152 |
| 101 | heptylamino | (2-aminobenzyl)amino | isopropyl | 0.6 | 0.4 | 0.02 |
| A2148 | 2-hydroxy-2-methylpropylamino | benzylamino | isopropyl | 0.6 | 0.4 | 0.5 |
| 8 | 2-hydroxy-2-methylpropylamino | (2-aminobenzyl)amino | methyl | 0.04 | 0.02 | 0.001 |
| 108 | 2-hydroxy-2-methylpropylamino | (2-aminobenzyl)amino | isopropyl | 0.02 | 0.008 | 0.0004 |
| 114 | 2-hydroxy-1-ethylpropylamino | (2-aminobenzyl)amino | isopropyl | 0.05 | 0.01 | 0.0008 |
| A2161 | (1-hydroxymethyl-2-methyl)propylamino | benzylamino | isopropyl | 0.6 | 0.4 | 0.5 |
| 7 | (1-hydroxymethyl-2-methyl)propylamino | (2-aminobenzyl)amino | methyl | 0.04 | 0.01 | 0.001 |
| 64 | (1-hydroxymethyl-2-methyl)propylamino | (2-aminobenzyl)amino | ethyl | 0.03 | 0.01 | 0.0009 |
| 107 | (1-hydroxymethyl-2-methyl)propylamino | (2-aminobenzyl)amino | isopropyl | 0.05 | 0.04 | 0.002 |
| 226 | (1-hydroxymethyl-2-methyl)propylamino | (2-amino-3-methoxylbenzyl)amino | cyclohexyl | 0.7 | 0.3 | 0.02 |

OC: olomoucine, RO: roscovitine, A1140, A1141, A2141, A2144, A216, A218, A2148, A2161 = compounds known from prior art.

Table 7 shows the results of inhibitory activity of novel compounds against CDK9 in comparison to CDK1 and CDK2 with the data of prototype compounds (trisubstituted purines olomoucine and roscovitine and other analogues known from the prior art). The novel derivatives showed enhanced inhibitory activity in in vitro kinase assays. Modification of the benzyl ring by amino group in ortho-position led systematically to an increase in CDK inhibitory activity and particularly in CDK9 inhibitory activity, and therefore the compounds of the invention are CDK9 specific inhibitors.

Example 4

In Vitro Cytotoxic Activity of Novel Compounds

We have been using the following cell lines: human T-lymphoblastoid leukaemic cell line CEM, promyelocytic leukemia HL 60, and monocytic U937 leukemia, breast carcinoma MCF7, cervical carcinoma cells HELA, mouse fibroblasts NIH3T3, human erythroleukaemia K562, human malignant melanoma G 361, human osteogenic sarcoma HOS, and normal human fibroblasts BJ for routine screening of the compounds. The cells were kept in Nunc/Corning 80 cm² plastic bottles and grown in cell culture medium (DMEM containing 5 g/l glucose, 2 mM glutamine, 100 U/ml penicilline, 100 µg/ml streptomycine, 10% fetal bovine serum and sodium hydrogencarbonate), the compounds were prepared according to the procedure of the present invention.

The cell suspensions were prepared and diluted depending on cell type and the assumed final cell density ($10^4$ cells per well, based on cell growth characteristics), 80 µl of cell suspension was pipetted to 96-well microtiter plate. The inoculates were stabilized by 24-hour pre-incubation at 37° C. in the $CO_2$ atmosphere. The tested compounds in tested concentrations were added in t=0 as 20 µl aliquots into the microtiter plate wells. The compounds were usually diluted into six concentrations in 4-fold dilutions. During the routine testing, the highest concentration in a well was 166.7 µM changes in this concentration depend on a substance. All concentrations were tested in doublets. The cells were incubated with the tested derivatives for 72 hours at 37° C., 100% humidity, in $CO_2$ atmosphere. At the end of the incubation period, the cells were analyzed after adding the Calceinu AM solution (Molecular Probes) and the incubation was carried out for another 1 hour. Fluorescence (FD) was measured by Labsystem FIA reader Fluoroskan Ascent (Microsystems). The tumor cell survival-TCS was calculated in accordance with the following equation: $GI_{50} = (FD_{jamka\ s\ derivátem}/FD_{kontrolní\ jamka}) \times 100\%$. The $GI_{50}$ value corresponding to the concentration of the compound lethal to 50% cancer cells was calculated from the obtained dose-response curves.

The cytotoxicity of the novel compounds was tested on panels containing cell lines of various histogenetic and species origin (Table 8). Higher activities were found in all tested tumour lines in comparison to control (normal cells). Notably, a higher effectiveness of novel derivatives was also found in cell lines bearing various mutations or deletions in cell cycle associated proteins, e.g. HL-60, CEM, K-562, HeLa, HOS, and G-361. It indicates that these substances should be equally effective in tumours with various alterations of tumour suppressor genes, namely p53, Rb, etc. Importantly, this observation distinguishes the novel compounds from flavopiridol and related compounds, as their biological activity is dependent on p53 status.

TABLE 8

Cytotoxicity of novel compounds for various cancer cells

| Cmpd No. | $IC_{50}$ (µM) | | | | | | | |
|---|---|---|---|---|---|---|---|---|
| | MCF7 | K-562 | HOS | G361 | CEM | HL60 | HeLa | BJ |
| OC | 132 | >167 | 142 | 161 | 62 | 123 | 108 | >167 |
| RO | 14 | 52 | 24 | 22 | 14 | 35 | 22 | >167 |
| 105 | 3.4 | 12.8 | 11 | 8 | 4.5 | 6.7 | 2.5 | >167 |
| 118 | 1.8 | 8.4 | 7.6 | 6 | 3.2 | 5.4 | 1.6 | >167 |
| 128 | 2.9 | 10.2 | 10.8 | 12 | 6.2 | 8.5 | 3.2 | >167 |
| 182 | 3.1 | 21 | 11 | 15 | 7.3 | 18 | 4.2 | >167 |
| 5 | 2 | 6 | 4 | 3 | 3 | 8 | 2 | >167 |
| 62 | 1.8 | 5.4 | 3.2 | 2.5 | 2.4 | 6.7 | 1.6 | >167 |
| 187 | 4.3 | 16 | 12 | 9 | 7.6 | 8.3 | 4.5 | >167 |
| 198 | 9 | 22 | 16 | 11 | 10 | 26 | 14 | >167 |
| 209 | 11 | 25 | 18 | 14 | 12 | 31 | 14 | >167 |
| 234 | 11 | 25 | 17 | 18 | 16 | 33 | 18 | >167 |
| 247 | 14 | 41 | 22 | 21 | 15 | 34 | 19 | >167 |
| A1140 | 52 | 86 | 97 | 83 | 31 | 69 | 50 | >167 |
| 1 | 13 | 46 | 22 | 22 | 15 | 31 | 18 | >167 |
| 115 | 4 | 11 | | | 6 | | | |
| 125 | 6 | 10 | | | 5 | | | |
| A1141 | 55 | 91 | 86 | 74 | 43 | 75 | 48 | >167 |
| 2 | 10 | 36 | 20 | 14 | 9 | 22 | 12 | >167 |
| 46 | 13 | 27 | 19 | 13 | 13 | 28 | 18 | >167 |
| 59 | 14 | 31 | 17 | 15 | 10 | 29 | 20 | >167 |
| 184 | 8 | 24 | 32 | 19 | 11 | 35 | 17 | >167 |
| A2141 | 33 | 47 | 28 | 27 | 33 | 47 | 28 | >167 |
| 102 | 5.5 | 20 | 44 | 17 | 9 | 32 | 16 | >167 |
| 116 | 4.5 | 14 | 23 | 10 | 6.7 | 22 | 8.7 | >167 |
| 138 | 3.8 | 9.5 | 25 | 13 | 8.7 | 23 | 9.2 | >167 |
| 161 | 7 | 18 | 26 | 14 | 9 | 26 | 12 | >167 |
| 195 | 12 | 38 | 22 | 14 | 11 | 24 | 13 | >167 |
| 231 | 15 | 37 | 23 | 15 | 12 | 32 | 16 | >167 |
| A2144 | 24 | 502 | 27 | 34 | 20 | 51 | 36 | >167 |
| 103 | 10.1 | 29.8 | 63 | 33 | 14 | 36 | 18 | >167 |
| A216 | 30.4 | 80 | 58 | 44 | 27 | 59 | 36 | >167 |
| 104 | 15.4 | 26 | 31 | 19 | 17 | 29 | 15 | >167 |
| 166 | 17 | 24 | 32 | 17 | 13 | 31 | 16 | >167 |
| A218 | 42.5 | 30.3 | 105 | 83 | 37 | 91 | 65 | >167 |
| 101 | 15.3 | 27 | 25 | 14 | 7 | 24 | 15 | >167 |
| A2148 | 65 | 47 | | | 66 | 51 | | |
| 8 | 1.8 | 3.4 | 1.1 | 1.7 | 0.6 | 2.8 | 1.3 | >167 |
| 108 | 1.2 | 3.0 | 1.0 | 1.9 | 0.5 | 2.2 | 1.0 | >167 |
| 114 | 11 | 28 | 19 | 15 | 17 | 34 | 17 | >167 |
| A2161 | 5.9 | 15.4 | 22 | 11.5 | 4.3 | 18 | 6.5 | >167 |
| 7 | 1.5 | 5 | 0.8 | 1.2 | 0.9 | 2.4 | 1.0 | >167 |
| 64 | 1.3 | 4.5 | 0.9 | 1.0 | 0.7 | 2.1 | 1.2 | >167 |
| 226 | 16 | 39 | 19 | 20 | 13 | 31 | 21 | >167 |

Note:
the numbering of compounds corresponds to that of Table 7

Example 5

Inhibition of CDK9 and RNA Polymerase II

Immunoblotting.

Cell were detached with rubber policeman and washed three times with ice-cold PBS and lysed in buffer (50 mM Tris, pH 7.4, 250 mM NaCl, 5 mM EDTA, 50 mM NaF, 1 mM $Na_3VO_4$, 1% Nonidet P40) containing mixture of protease and phosphatase inhibitors (Sigma-Aldrich St Louis, Mo., USA). 20 µg of total proteins were separated by SDS-polyacrylamide gel electrophoresis (SDS-PAGE) on 8% or 10% gels and transferred onto nitrocellulose membranes. Membranes were blocked in 5% milk and 0.1% Tween 20 in PBS and probed overnight with specific monoclonal antibodies or rabbit polyclonal sera. Primary antibodies specific for RNA polymerase II (all from Santa Cruz Biotechnology, California, USA) included: (i) N-20 used at 1 µg/ml, (ii) H14, specific for form phosphorylated at phosphoserine 5, used at 6 µg/ml and (iii) H5, specific for form phosphorylated at phosphoserine 2 used at 4 µg/ml. Additional primary mAb used in immunblots included (iv) anti-p53 (DO-1, in house) used at 1 µg/ml, (v) anti-p21$^{WAF1}$ (118, in house), used at 1 µg/ml), (vi) anti-actin (A-2066, Sigma-Aldrich St Louis, Mo., USA) used at 1 µg/ml, (vii) anti-T-antigen (419, in house), used at 1 µg/ml. All primary antibodies were diluted in PBS containing 5% powdered milk; 0.1% Tween 20. Peroxidase conjugated rabbit anti-mouse immunoglobulin or porcine anti-rabbit immunoglobulin antisera (DAKO, Glostrup, Denmark) were used as the secondary antibodies and visualised with ECL reagents (Amersham-Pharmacia, Little Chalfont, UK).

Phosphorylation of the C-Terminal Domain of RNA Polymerase II.

Figure 2:
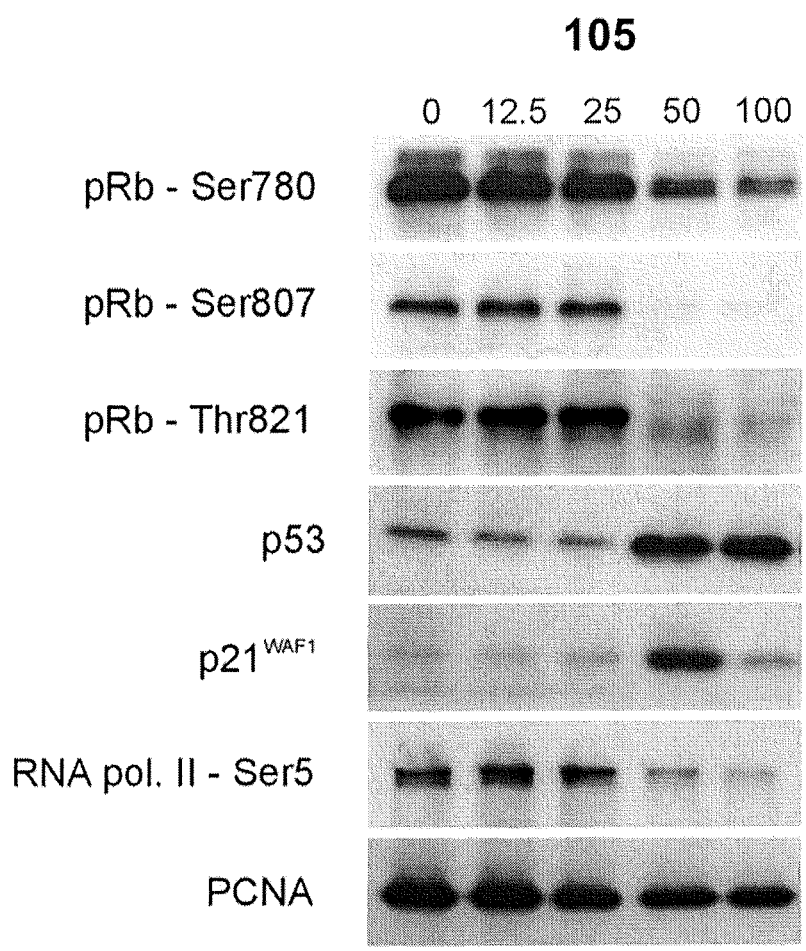
FIG. 2 shows immunoblot analyses of MCF7 cells treated for 24 h with the indicated concentrations of the compound 105. Reduced phosphorylation of pRb at Ser780, Ser807 and Thr821 is observed, indicating decreased activity of CDK4 and CDK2, respectively. Induction of tumor suppressor p53 level and $p21^{WAF1}$ as well as reduced phosphorylation of CTD of RNA polymerase II indicates blocked transcription.

Modulation of expression from the HIV promoter by CDKI treatment may be mediated by transcriptional regulation. At the C-terminus of the largest subunit of RNA Pol II is an important regulatory domain referred to as CTD (C-terminal domain). We therefore investigated the effect of CDKIs on CTD serine 2 and serine 5 phosphorylation. The levels of both serine 2 and serine 5 phosphorylation in compound 105 (substituents on purine C2: (1-hydroxymethyl)propylamino, C6: (2-aminobenzyl)amino, N9: isopropyl) treated COS-1, CV-1 and MCF-7 cells were substantially reduced under all experimental conditions tested (FIG. 2). Although the functions of CDKs and RNA polymerase II were suppressed, the expression from incorporated viral promoters was enhanced. These observations support the contention that the mechanism of action of the CDKIs on expression from the HIV promoter lies with transcription control, and exhibits a differential effect depending on whether the target promoter was maintained as an extrachromosomal element or integrated in the cellular genome.

Example 6

Induction of Tumour Supressor p53 in Cancer Cells

Cell Cultures and Treatment.

Cell lines established from the human cervical carcinoma (HeLa), human breast carcinoma (MCF-7, BT549 and BR474), human osteosarcoma (HOS), human colon carcinoma (HT29), murine fibroblasts (T22lacZ) and the human melanoma (Arn8) cell lines were cultured in Dubecco's Modified Eagle Medium (DMEM) supplemented with 10% foetal bovine serum. Tested compounds were added from 50 mM stock solution in dimethyl-sulphoxide (DMSO) into the culture medium at final concentration 20 µM. Control cells received an equivalent volume of DMSO.

Analysis of p53-Dependent Transcriptional Activity.

β-galactosidase activity of human melanoma cell line Arn8 and murine fibroblasts cell line Arn8 and murine fibroblasts cell line T22lacZ (both stabile transfected with a p53-responsive reporter construct pRGCΔfoslacZ) (Frebung et al., Cancer Res., 52, 1992-6976) was determined. For the determination of total β-galactosidase activity, cells were lysed by 3 freeze-thaw cycles in 0.25 M Tris pH 7.5, and lysates were assayed as described by Sambrook et al. (Mol. Cloning, New York, 1989). The results are shown in Table 9.

Antibodies (a) DO-1, DO-2 and 1801 monoclonal antibodies recognise the N-terminal region of p53 protein, monoclonal antibodies DO-11 and DO-12 recognise different epitopes in the core domain of p53 protein, monoclonal antibodies Bp53-10 and Pab421 recognise the C-terminal region of p53 protein.

(b) Monoclonal antibody 118 recognises p21$^{WAF1}$.

Polyacrylamide Gel Electrophoresis and Immunoblotting.

For direct immunoblotting, total cellular protein lysates were prepared by harvesting cells in hot Laemmli electrophoresis sample buffer. Proteins were then separated by SDS-polyacrylamide gel electrophoresis (SDS-PAGE) on 10% gel and transferred onto a nitrocellulose membrane in Bio.Rad Mini Trans-Blott Electrophoretic Transfer Cell for 2 hrs at 4° C. applying 150 mA in transfer buffer (240 mM Tris, 190 mM glycine and 20% methanol). Prestained molecular weight markers (Bio-Rad) were run in parallel. The blotted membranes were blocked in 5% milk and 0.1% Tween 20 in PBS for 2 hrs and probed overnight with monoclonal antibodies. After washing 3 times in PBS plus 0.1% Tween 20, peroxidase conjugated rabbit anti-mouse immunoglobulin antiserum (Dako, Denmark) diluted 1:1000 was used as the secondary antibody. To visualise peroxidase activity, ECL reagents from AMERSHAM were used according to the manufacturer instructions.

Transfection Experiment.

MCF7-DDp53 cell line was derived from MCF-7 parental cell line by stable transaction with plasmid pCMV-neonDDp53 coding for dominant negative truncated mouse p53 protein including amino acid residues 1-14 and 302-390 under the control of at the CMV promoter. The control cell line MCF-7neo was derived by transfecting MCF-7 cells with pCMVneo vector. Transfections were performed using the Effectene transfection reagent (QIAGEN, Germany) as recommended by the supplier. Stable transfectants were selected at 2 mg/ml G418 sulphate (Life Technologies). The expression of Ddp53 miniprotein in MCF-7Ddp53 cell line has been examined by immunoblotting with Bp53-10 monoclonal antibody. Independently isolated MCF-7Dp53 clones 9, 12 and 14 expressing high levels of Ddp53 miniprotein and MCF-7-neo clones 3, 4 and 7 were used.

Compound 105 Induces Wild-Type, but not Mutant, p53 Protein.

Figure 3:
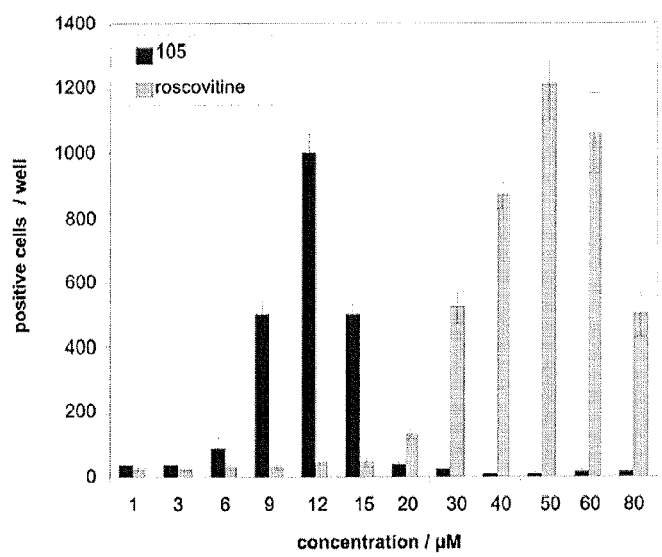
FIG. 3 displays dose-dependent effect of 105 and roscovitine on p53-dependent transcription. A, Arn8 cells stably transfected with a p53-responsive β-galactosidase reporter construct were treated with different CDK inhibitors for 24 h and positive cells were counted under a light microscope for each concentration in triplicate. B, induction of p53 and $p21^{WAF1}$ proteins in Arn8 cells treated with the indicated concentrations of CDK inhibitors. C, induction of p53 and $p21^{WAF1}$ proteins in MCF-7 after 105 treatment. The cells were harvested, the proteins were separated on a 10% SDS-PAGE gel and analyzed on Western blots with specific antibodies.
Figure 3:
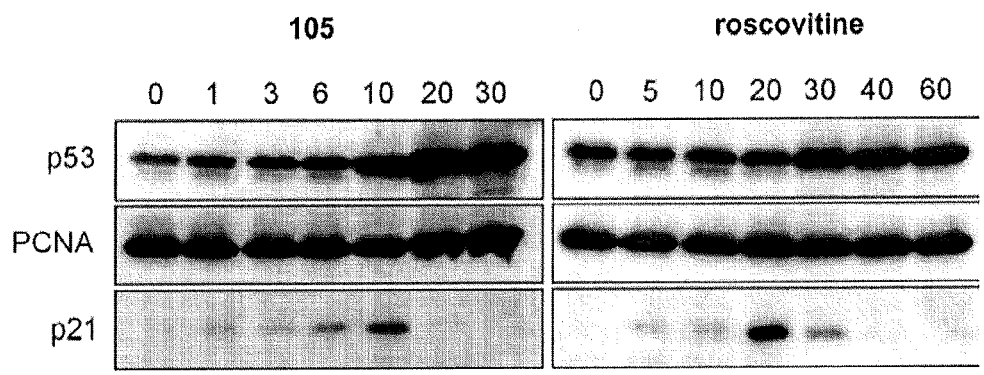
Figure 3:
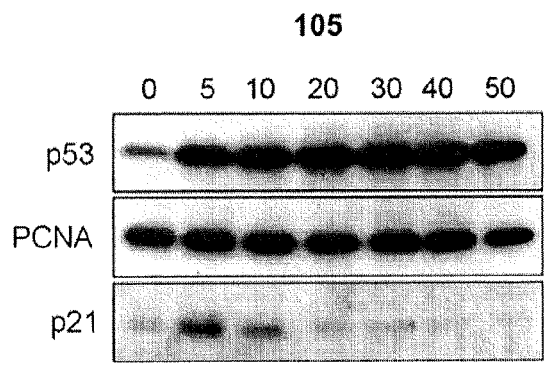
Figure 4:
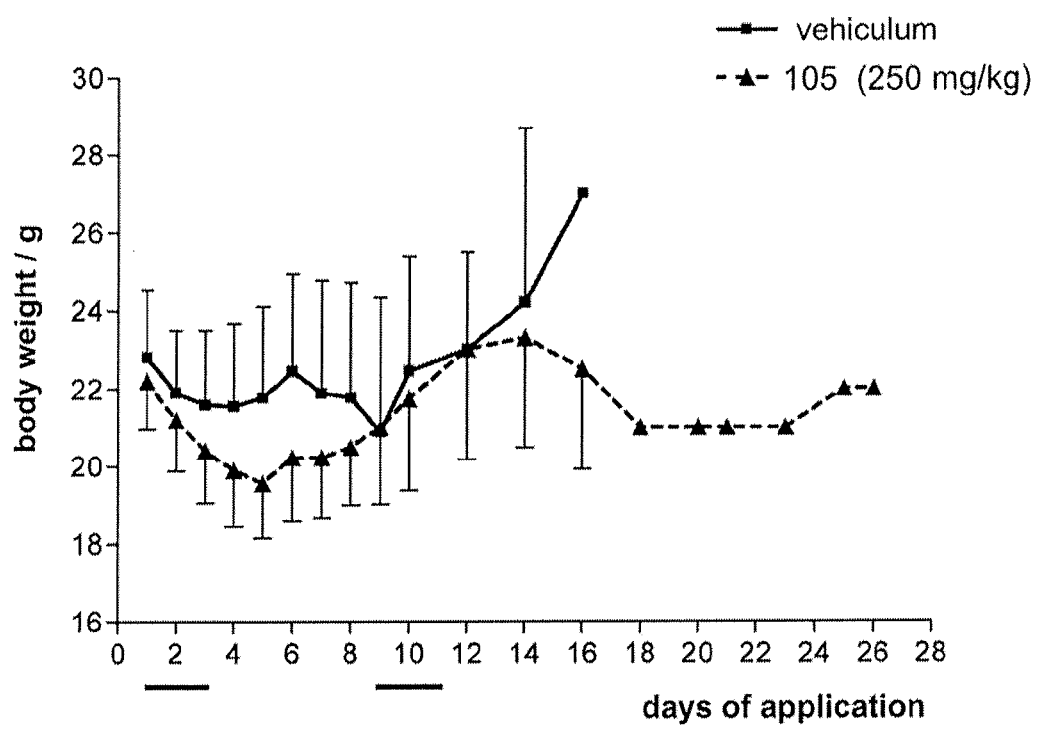
FIG. 4 shows total body weight of mice transplanted with P388D1 leukemia, treated intraperitoneally with selected CDK inhibitors.
Figure 5:
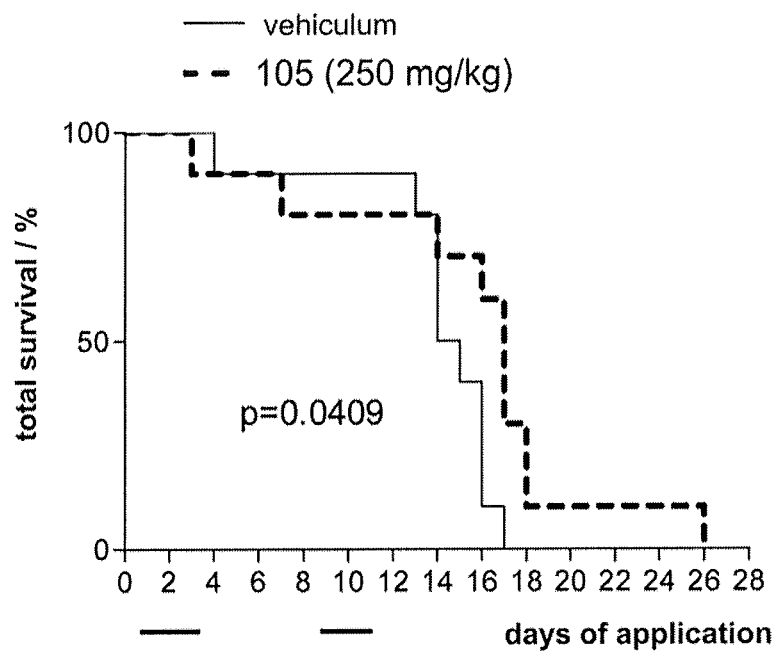
FIG. 5 shows survival analysis of mice transplanted with P388D1 leukemia, treated intraperitoneally with selected CDK inhibitors.
Figure 6:
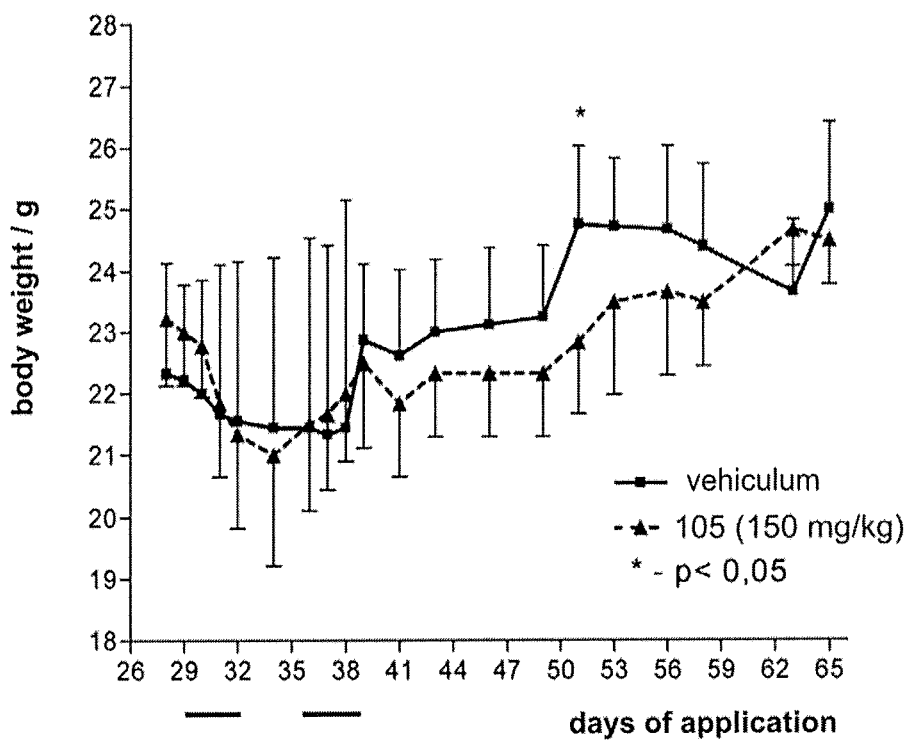
FIG. 6 shows total body weight of mice transplanted with A549 human lung adenocarcinoma, treated intraperitoneally with selected CDK inhibitors.
Figure 7:
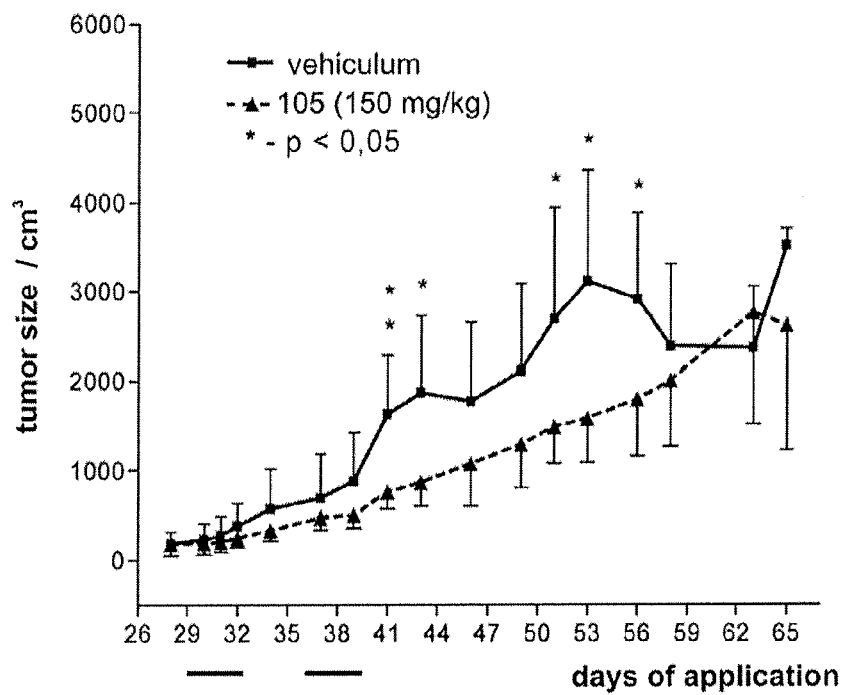
FIG. 7 shows tumor volume analysis of mice transplanted with A549 human lung adenocarcinoma, treated intraperitoneally with selected CDK inhibitors.

First, we determined appropriate concentration of 103 and 105 for our experiments. The MCF-7 (wt p53) cells were treated for 12 hrs with increasing concentrations of 105 ranging from 1 to 100 µM and analysed for p53 protein expression using monoclonal antibody DO-1 (FIG. 3A). The concentration of 105 2-5 µM has been shown to affect the level of p53 protein in these cells. As shown at FIG. 3C the level of protein expression induced by 5 µM 105 was not substantially different from expression induced by 50 µM concentration was selected for further experiments. Second, the periods of time 6, 12 and 24 hrs were chosen, since the level of protein expression reached a steady state. We analysed the expression of p53 protein in MCF-7 (wt p53), BT549 (mut p53) and BT474 (mut p53) breast cancer cell lines, in HT29 (mut p53) colorectal cancer cell line and in ostaosarcoma cell line HOS (mut p53). Treatment of MCF-7 cells for 6, 12 and 24 hrs with 5 µM 105 results in significant accumulation of wild-type p53. No induction of p53 was observed following exposure of BT549 and HOS cell lines, expressing mutant p53, to 5 µM 105 for 6, 12 and 24 hrs. No correlation was observed between the sensitivity of cell lines to 105 and the presence of wild-type or mutant p53.

105-Induced wt p53 is Transcriptionally Active and Responsible for Induction of p21$^{WAF1}$.

Effect of 105 and related compounds on activation of p53 protein was also analysed in human melanoma cell line Ara and murine fibroblast cell line T22LacZ expressing β-galactosidase under control of p53 responsive promoter. Induction of wt p53 in these cells treated with 5 µM 105 (6, 12 and 24 hrs) leads to activation of responsive promoter and consequently to expression of β-galactosidase. Arn8 and T22lacZ cells treated with 105 were fixed and examined microscopically for β-galactosidase activity using X-gal substrate leading to about 25% blue-coloured cells compared to less than 1% of blue-coloured cells in DMSO-treated control cells (FIG. 3A). The total β-galactosidase activity in Arn8 cells was also assessed using colorimetric assay. The results show strong activity of β-galactosidase at periods of time 12 and 24 hours after treatment giving evidence of transcriptionally active p53 protein in comparison with control cells treated with DMSO.

This transcription activity was also proved by analysing p21$^{WAF1}$ expression in MCF-7 cells. The induction of p53 protein was apparent in 4 hrs but enhanced level of p21$^{WAF1}$ protein was observed in only 12 hrs after treatment with 105 (FIG. 3B). Only cells expressing wt p53 responded to 105 with p21 induction. To confirm, that p21$^{WAF1}$ induction is p53-responsive, a series of stable transfected MCF-7 clones expressing high levels of a dominant-negative Ddp53 mini-protein was established. This protein, consisting of amino acids 1-14 and 302-390 of mouse p53 sequence, has been shown to bind to the C-terminus of wt p53 and abrogate the p53-dependent transcription. The control MCF-7neo clones were also established by stable transfection of MCF-7 cells with the backbone vector pCMVneo without insert. Clones expressing high level of Ddp53 as well as the control clones were treated with 105 and assayed for p21$^{WAF1}$ expression using immunoblotting with p21$^{WAF1}$ specific monoclonal antibody 118. As a result of Ddp53 expression, disrupting p53 transcriptional activity, no p21$^{WAF1}$ induction could be detected in MCF-7Ddp53 clones.

Other compounds had comparable effects but the concentrations of the tested compound inducing maximum of β-galactosidase activity differed from each to another. These results are presented in Table 9 as concentration inducing maximum of 6-galactosidase activity. It seems that substituted 6-(2-aminobenzylamino)purines are powerful inducers of wt p53 expression.

TABLE 9

The effect of selected substituted 6-(2-aminobenzylamino)purines on the induction of p53 protein as well as p21$^{WAF1}$ protein in MCF-7 cells expressing wild-type p53.

| No | SUBSTITUENT ON PURINE C2 | C6 | N9 | Max. β-Gal. Activtity Conc. (μM) |
|---|---|---|---|---|
| OC | 2-hydroxyethylamino | benzylamino | methyl | 125 |
| RO | (1-hydroxymethyl)propylamino | benzylamino | isopropyl | 50 |
| 1 | 2-aminocyclohexylamino | (2-aminobenzyl)amino | methyl | 34 |
| 2 | 4-aminocyclohexylamino | (2-aminobenzyl)amino | methyl | 37 |
| 5 | (1-hydroxymethyl)propylamino | (2-aminobenzyl)amino | methyl | 29 |
| 7 | (1-hydroxymethyl-2-methyl)propylamino | (2-aminobenzyl)amino | methyl | 25 |
| 8 | 2-hydroxy-2-methylpropylamino | (2-aminobenzyl)amino | methyl | 24 |
| 9 | 2-hydroxy-1,2-dimethylpropylamino | (2-aminobenzyl)amino | methyl | 25 |
| 12 | 3-hydroxy-2,3-dimethylbutylamino | (2-aminobenzyl)amino | methyl | 33 |
| 13 | 2-hydroxy-1-ethyl-2-methylpropylamino | (2-aminobenzyl)amino | methyl | 36 |
| 46 | 4-aminocyclohexylamino | (2-amino-3-methoxybenzyl)amino | methyl | 32 |
| 59 | 4-aminocyclohexylamino | (2-aminobenzyl)amino | ethyl | 33 |
| 62 | (1-hydroxymethyl)propylamino | (2-aminobenzyl)amino | ethyl | 7 |
| 64 | (1-hydroxymethyl-2-methyl)propylamino | (2-aminobenzyl)amino | ethyl | 6 |
| 101 | 2-aminocyclohexylamino | (2-aminobenzyl)amino | isopropyl | 22 |
| 102 | 4-aminocyclohexylamino | (2-aminobenzyl)amino | isopropyl | 13 |
| 103 | 4-hydroxycyclohexylamino | (2-aminobenzyl)amino | isopropyl | 14 |
| 104 | 2-hydroxypropylamino | (2-aminobenzyl)amino | isopropyl | 12 |
| 105 | (1-hydroxymethyl)propylamino | (2-aminobenzyl)amino | isopropyl | 16 |
| 106 | heptylamino | (2-aminobenzyl)amino | isopropyl | 41 |
| 107 | (1-hydroxymethyl-2-methyl)propylamino | (2-aminobenzyl)amino | isopropyl | 11 |
| 108 | 2-hydroxy-2-methylpropylamino | (2-aminobenzyl)amino | isopropyl | 3 |
| 109 | 2-hydroxy-1,2-dimethylpropylamino | (2-aminobenzyl)amino | isopropyl | 6 |
| 110 | 3-hydroxy-3-methylbutylamino | (2-aminobenzyl)amino | isopropyl | 29 |
| 111 | 3-hydroxy-1,3-dimethylbutylamino | (2-aminobenzyl)amino | isopropyl | 32 |
| 112 | 3-hydroxy-2,3-dimethylbutylamino | (2-aminobenzyl)amino | isopropyl | 35 |
| 113 | 2-hydroxy-1-ethyl-2-methylpropylamino | (2-aminobenzyl)amino | isopropyl | 16 |
| 114 | 2-hydroxy-1-ethylpropylamino | (2-aminobenzyl)amino | isopropyl | 3 |
| 116 | 4-aminocyclohexylamino | (2-amino-5-chlorobenzyl)amino | isopropyl | 21 |
| 118 | (1-hydroxymethyl)propylamino | (2-amino-5-chlorobenzyl)amino | isopropyl | 18 |
| 128 | (1-hydroxymethyl)propylamino | (2-amino-5-fluorobenzyl)amino | isopropyl | 4 |
| 138 | 4-aminocyclohexylamino | (2-amino-3-methylbenzyl)amino | isopropyl | 2 |
| 161 | 4-aminocyclohexylamino | (2,5-diaminobenzyl)amino | isopropyl | 20 |
| 166 | 2-hydroxypropylamino | (2-amino-3-methoxybenzyl)amino | isopropyl | 14 |
| 182 | (1-hydroxymethyl)propylamino | (2-amino-5-methoxybenzyl)amino | isopropyl | 12 |
| 184 | 4-aminocyclohexylamino | (2-aminobenzyl)amino | propyl | 6 |
| 187 | (1-hydroxymethyl)propylamino | (2-aminobenzyl)amino | propyl | 3 |
| 195 | 4-aminocyclohexylamino | (2-aminobenzyl)amino | cyclohexyl | 22 |
| 198 | (1-hydroxymethyl)propylamino | (2-aminobenzyl)amino | cyclohexyl | 19 |
| 209 | (1-hydroxymethyl)propylamino | (2-amino-5-chlorobenzyl)amino | cyclohexyl | 20 |

TABLE 9-continued

The effect of selected substituted 6-(2-aminobenzylamino)purines on the induction of p53 protein as well as p21$^{WAF1}$ protein in MCF-7 cells expressing wild-type p53.

| No | SUBSTITUENT ON PURINE | | | Max. β-Gal. Activtity Conc. (μM) |
|---|---|---|---|---|
| | C2 | C6 | N9 | |
| 226 | 2-hydroxypropylamino | (2-amino-3-methoxylbenzyl)amino | cyclohexyl | 21 |
| 231 | 4-aminocyclohexylamino | (2-aminobenzyl)amino | benzyl | 18 |
| 234 | (1-hydroxymethyl)propylamino | (2-aminobenzyl)amino | benzyl | 24 |
| 247 | (1-hydroxymethyl)propylamino | (2-amino-5-chlorobenzyl)amino | benzyl | 20 |
| 226 | 4-aminocyclohexylamino | (2-amino-3-methoxylbenzyl)amino | benzyl | 27 |

Example 7

In Vivo Anticancer Activity

Screening of biological activity of compound 105 was performed on survival model of P388D1 leukemia transplanted intraperitoneally with 2.10$^5$ cells. DBA-2 mice were used as a host. One day following the leukemia transplantation, treatment with 105 was initiated. The drug was given orally by gastric gavages in total volume of 200 μl/dose twice daily at dose 250 mg/kg in two chemotherapy cycles (Days 1-3 and 7-9). The compound 105 was solubilized in 5% N-methyl-2-pyrrolidine, 30% polyethylene glycol 400, 65% tartar buffer (pH 3.0). Survival analysis of treated animals (10 mice/group) was preformed in comparison with vehicle treated mice using Kaplan-Meier method and the significance was evaluated by the log-rank test. Body weight of experimental animals was evaluated in parallel in order to reflect toxicity and efficacy of therapy. Comparative analysis of body weight was performed using non-parametric t-test.

Results of our analysis demonstrated that compound 105 is reducing body weight of treated animals, which is in the model of intraperitoneally transplanted P388D1 leukemia indicative for both toxicity and efficacy of the treatment (reduction of ascites and intraperitoneal tumor formation). Survival analysis demonstrated significantly better survival of mice treated with 105 (P=0.0409) that has been translated to longer mean survival time (15.4 days for drug treated group versus 13.9 days for vehicle treated group).

More detailed analysis of anticancer activity of compound 105 was performed on human xenograft model of A549 lung adenocarcinoma transplanted to CD-1 SCID mice. Animals were transplanted subcutaneously with 2.10$^6$ A549 cells into lower back. Approximately one month later, majority of animals developed palpable tumors and therapy was initiated. The drug was given orally by gastric gavages in total volume of 200 μl/dose twice daily at dose 150 mg/kg in two chemotherapy cycles (Days 1-3 and 7-9). The compound 105 was solubilized in 5% N-methyl-2-pyrollidine, 30% polyethylene glycol 400, 65% tartar buffer (pH 3.0). Primary endpoint for analysis was reduction of tumor volume (10 mice/group), which was quantified by caliperation. Analysis of treated animals was preformed in comparison with vehicle treated mice. Body weight of experimental animals was also evaluated in parallel in order to reflect toxicity of the therapy. Comparative analysis of tumor volumes and body weights was performed using non-parametric t-test.

Results of our analysis demonstrated that compound 105 has good tolerability in animals. There was only slight reduction the body weight of treated animals, which was however significant in one time point (Day 52) only.

Tumor volume analysis showed significantly smaller tumors in mice treated with 105 (P=0.0409) that has been translated to longer mean survival time (15.4 days for drug treated group versus 13.9 days for vehicle treated group).

Example 8

Antiviral Activity

Cell Culture.

The African green monkey kidney cell line CV-1 (wild-type p53), COS-1 cells (established from CV-1 by transformation with an origin-defective mutant of SV40), the human non-small cell lung carcinoma cell line H1299, the human breast adenocarcinoma cell line MCF-7 (wild-type p53) and the human breast carcinoma cell line T47D (mutant p53) were all maintained in Dulbecco's modified Eagle medium (DMEM) containing 10% fetal bovine serum, 300 μg/ml L-glutamine, 105 IU/ml penicillin and 100 μg/ml streptomycin. Human fetal foreskin fibroblasts (HFFF) (wild-type p53), human lung carcinoma epithelial cells A549 (wild-type p53), Human B95a B cells and Madin-Darby canine kidney (MDCK) epithelial cells were grown in DMEM supplemented with 10% heat inactivated fetal bovine serum, 105 IU/ml penicillin and 100 μg/ml streptomycin. Cells were grown to 80% confluence prior to experimental treatments. If not otherwise stated, 20 μM Roscovitine and 10 μM 105 were added to the cells for period of 12 hours.

Generation of Stable Cell Lines.

The plasmids pCEP4-Tat and pHIV-lacZ were obtained from the NIH AIDS Research & Reference Reagent Program (Chang et al. Gene Ther. 6(5):715-28, 1999). pCEP4-Tat contains HIV-1SF2 tat, while pHIV-lacZ contains all of the U3 region, part of the R region (including the TAR) and the HIV-1 3'LTR driving lacZ, and pCMV-lacZ contains lacZ under human cytomegalovirus promoter. DNA transfections were carried out using Lipofectamine 2000 (Invitrogen, Carlsbad, Calif., USA) according to the manufacturer's instructions. Cell line H1299-TAT was derived from H1299 cells stabile transfected with pCEP4-Tat. Cell line H1299-HIV was prepared by stable co-transfection with pCEP4-Tat and pHIV-lacZ plasmids. Two days after transfection, cells were selected with hygromycin B (250 μg/ml; Merck Biosciences, Nottingham, UK) to generate stable clones with incorporated plasmid DNA. Selected stable transfected (i) H1299-TAT clones were transiently transfected with pHIV-lacZ and tested for β-galactosidase activity (see below) while (ii) H1299-HIV cells were tested for β-galactosidase activity immediately due to stable incorporation of both plasmids.

Beta-Galactosidase Assay.

To measure β-galactosidase activity, cells were harvested 12 h post transfection and disrupted by sonication in 0.25 M Tris-HCl pH 7.5. Cell lysates (100 μg) were mixed with 3 μl of buffer (0.1 M $MgCl_2$, 4.5 M β-mercaptoethanol), 66 μl ONPG (4 mg/ml o-nitrophenyl-β-D-galactopyranoside in 0.1 M sodium phosphate buffer, pH 7.5) and 0.1 M sodium phosphate buffer, pH 7.5. The reaction was incubated for 30 minutes at 37° C., stopped with 500 μl of 1 M $Na_2CO_3$ and the absorbance at 420 nm determined in a microplate reader.

Immunoblotting.

Cell were detached with rubber policeman and washed three times with ice-cold PBS and lysed in buffer (50 mM Tris, pH 7.4, 250 mM NaCl, 5 mM EDTA, 50 mM NaF, 1 mM $Na_3VO_4$, 1% Nonidet P40) containing mixture of protease and phosphatase inhibitors (Sigma-Aldrich St Louis, Mo., USA). 20 μg of total proteins were separated by SDS-polyacrylamide gel electrophoresis (SDS-PAGE) on 8% or 10% gels and transferred onto nitrocellulose membranes. Membranes were blocked in 5% milk and 0.1% Tween 20 in PBS and probed overnight with specific monoclonal antibodies or rabbit polyclonal sera. Primary antibodies specific for RNA polymerase II (all from Santa Cruz Biotechnology, California, USA) included: (i) N-20 used at 1 (ii) H14, specific for form phosphorylated at phosphoserine 5, used at 6 μg/ml and (iii) H5, specific for form phosphorylated at phosphoserine 2 used at 4 μg/ml. Additional primary mAb used in immunblots included (iv) anti-p53 (DO-1, in house, citace) used at 1 μg/ml, (v) anti-p21$^{WAF1}$ (118, in house), used at 1 μg/ml), (vi) anti-actin (A-2066, Sigma-Aldrich St Louis, Mo., USA) used at 1 μg/ml, (vii) anti-T-antigen (419, in house, Lane), used at 1 μg/ml. All primary antibodies were diluted in PBS containing 5% powdered milk; 0.1% Tween 20. Peroxidase conjugated rabbit anti-mouse immunoglobulin or porcine anti-rabbit immunoglobulin antisera (DAKO, Glostrup, Denmark) were used as the secondary antibodies and visualised with ECL reagents (Amersham-Pharmacia, Little Chalfont, UK).

Infection and Viruses.

The cell lines MCF-7 and T47D were infected with SV40 virus for 4 hours in serum-free DMEM. After infection, DMEM was supplemented with 10% foetal bovine serum and either 20 μM Roscovitine or 8 μM 105 added immediately or 12 h post infection. Infected cells were harvested at 45 h. Herpes simplex virus type 1 strain 17 (HSV-1), HSV-1 strain 17 containing GFP in the thymidine kinase (TK) locus (HSV-1-deltaTK), and HSV-2 strain HG52 (HSV-2) have been used. Herpesviruses were all propagated and titrated in HFFF cells. Vaccinia virus strain WR encoding influenza PB2 in the TK locus (VV) was propagated and titred in HFFF cells. Human adenovirus type 4 (HAdV-4) strain RI-6 was propagated and titred in A549 cells. Human cytomegalovirus strain Toledo encoding GFP in the 132.7 locus (HCMV) (McSharry et al., J. Gen. Virol. 2003, 84:2511-62003) was propagated and titred in HFFF cells. Measles virus (MV) wildtype strain WTFb was a gift from J. Schneider Schaulies, Wuerzbug, Germany. MV was propagated and titered in B95a cells. Measles Virus titers were determined as syncytium forming units (SFU). Influenza Virus (IV) $H_1N_1$ strain A/PR/8/34, obtained from European Collection of Animal Cell Cultures (Porton Down, UK), was propagated in the allantoic cavity of embryonated chicken eggs (strain 0; Institute for Animal Health, Compton, UK) at 35° C. Eggs were infected on day 6 and allantoic fluid was collected on day 10. IV titers were determined as HA units (HAU; inverse of log 2 endpoint dilution titer) by hemagglutination of chicken erythrocytes (Fiebig Naehrstofftechnik, Bad Kreuznach, Germany) and as infectious center forming units (ICFU) per milliliter of allantoic fluid. ICFU were determined in MDCK cells grown in 12 well plates (NUNC, Roskilde, Denmark) on 16 mm glass cover slips using a cocktail of directly FITC labelled monoclonal antibodies against A type influenza viruses (K6105 A reagent, DAKO, Glostrup, Denmark).

Antiviral Agents.

Where indicated, the following virostatics were used: Acyclovir (9-[(2-Hydroxyethoxy)methyl]guanine) (Sigma-Aldrich St Louis, Mo., USA), Cidofovir ((S)-1-[3-Hydroxy-2-(phosphonylmethoxy)propyl]-cytosine) (Moravek, Biochemicals), Iodo-deoxyuridine (1-(2-Deoxy-β-D-ribofuranosyl)-5-iodouracil) (Sigma), Ribavirin (1-β-D-Ribofuranosyl-1,2,4-triazole-3-carboxamide) (Sigma-Aldrich St Louis, Mo., USA), Tamiflu ((3R,4R,5S)-4-acetylamino-5-amino-3-(1-ethylpropoxy)-1-cyclohexene-1-carboxylic acid ethyl ester) (Roche), Chloroquine (N'-(7-chloroquinolin-4-yl)-N,N-diethyl-pentane-1,4-diamine) (Sigma-Aldrich St Louis, Mo., USA), Roscovitine (2-(R)-(1-Ethyl-2-hydroxyethylamino)-6-benzylamino-9-isopropylpurine) was prepared according to published methods (Havlíček et al., J. Med. Chem. 40: 408-412, 1997). The antivirals were used as indicated in the text.

Plaque Number Reduction Assays.

The 50% inhibiting concentrations ($IC_{50}$) were calculated using a standard plaque number reduction assay. The $IC_{50}$ was defined as the concentration of an antiviral that reduced the number of plaques by 50% relative to mock treatment without antiviral. Cells were grown in 25 $cm^2$ tissue culture flasks (Corning) until confluent, then infected with 100 plaque forming units (PFU) of appropriate virus (HSV-1 infection on HFFF, HSV-1-deltaTK on HFFF, HSV-2 on HFFF, VV on HFFF, HAd4 on A549, HCMV on HFFF) for 1 hour in 37° C. $CO_2$ incubator on a rocking platform. Cells were then overlayed with medium containing 1% Avicel RC-591 (Camida Ltd) (Matrosovich et al., Virol. J. 3:63, 2006) and the antiviral agent under test. Compound 105 and Roscovitine were typically tested at concentrations ranging from 0.04 μM to 20 μM. Where appropriate, Acyclovir, Cidofovir, Iodo-deoxyuridine, Chloroquine, Tamiflu and Ribavirin were used for comparison, and were applied over a range that included their reported peak $IC_{50}$ value. Infected cell monolayers were stained with Giemsa (Sigma) after 3 days (for HSV-1, HSV-1-deltaTK, HSV-2 & VV) or 5 days (HAd4) and plaques counted. For HCMV, after 7 days of incubation, cell monolayers were washed with PBS and green fluorescent foci were counted using Leica DMIRBE microscope. The plaque counts were plotted and analyzed using Cricket Graph software (Computer Associates).

To perform a MV syncytium reduction assay, B95a cells were grown in 24 well plates (NUNC, Roskilde, Denmark) until 80% confluent. Cells were pretreated with medium containing the appropriate amount of antiviral for 30 minutes prior to infection. Each well was infected with 100 SFU of MV and incubated in DMEM without FBS or antibiotics containing no antiviral or antiviral at range of concentrations for 24 hours. Syncytia formations were assessed by phase contrast microscopy. $IC_{50}$ was defined as the concentration of antiviral that reduced the number of syncytia by 50% in comparison to cells infected in the absence of antiviral.

IV infectious center reduction assay were performed in MDCK cells grown on 16 mm diameter glass cover slips in 12 well plates (NUNC, Roskilde, Denmark) until 80% confluent. Cells were pretreated with medium containing the antiviral agent under test for 30 minutes prior to infection. Each well was infected with 100 ICFU of IV incubated in DMEM without FBS or antibiotics and containing no antivirals or antivirals at a range of concentrations for 24 hours. Cells were washed with PBS, fixed with 3% paraformaldehyde (Sigma-Aldrich St Louis, Mo., USA), permeabilized with 1% Triton X 100 (Sigma-Aldrich St Louis, Mo., USA) in PBS and stained with a cocktail of monoclonal antibodies against A type influenza viruses (K6105 A reagent, DAKO, Glostrup, Denmark). Infectious center forming units (green fluorescent cytoplasma and/or fluorescent nuclei) were quantitated by using Axioplan epifluorescent microscope with Axiovision software (Carl Zeiss, Jena, Germany). $IC_{50}$ was defined as the concentration of antiviral that reduced the number of infectious centers by 50% in comparison to cells infected in the absence of antiviral. The final $IC_{50}$ values for all virus/antiviral combinations are each an average from 4 experiments.

HAd4 Yield Reduction Assay.

Confluent monolayers of A549 cells in 6 well tissue culture dishes were infected with 2000 PFU/well of HAd4 for 1 hour in 37° C. $CO_2$ incubator on a rocking platform. Cells were then rinsed and grown in medium containing 10 μM Compound 105 or 100 μM Cidofovir or a cocktail of 10 μM Compound 105 and 100 μM Cidofovir. The cells and media were harvested at 6 hours, 12 hours, 24 hours, 48 hours, 72 hours and 96 hours after infection, then released virus and total virus (released and intracellular) yields in each sample were titrated using A549 cells.

Inhibition of Viral Replication by Compound 105 and Roscovitine.

With the demonstration that Compound 105 was a more potent inhibitor of CDK activities than Roscovitine, it was clearly important to evaluate the relative capacity of these two CDKIs to impair virus replication. Using plaque reduction assays, we compared the effect of Compound 105 on replication of a panel of DNA (HSV, VV, HAd4, HCMV) and RNA (MV, IV) viruses against a range of reference antiviral agents (Table 1). Compound 105 inhibited replication of all the DNA viruses tested more effectively than Roscovitine. Roscovitine did not inhibit either HSV-1 or HSV-2 whereas Compound 105 did, albeit with a higher $IC_{50}$ than Acyclovir. Acyclovir is a pro-drug that becomes activated following phosphorylation by the virus-encoded TK. The HSV-1 thymidine kinase (TK) deletion mutant remained sensitive to Compound 105 yet resistant to Acyclovir, thus illustrating that Compound 105 acted by a different mechanism (Table 10). Even though the sensitivities of HSV-1 and HSV-2 to Acyclovir differed, their $IC_{50}$ values for Compound 105 were similar. Indeed, all the DNA viruses were inhibited at similar concentrations of Compound 105, consistent with the drug targeting cellular (CDKs) rather than the specific virus-encoded functions. Vaccinia virus was inhibited equally well with Compound 105 and Iododeoxyuridine, while Roscovitine exhibited no overt effect. Replication of VV had been thought not to require CDK functions, indeed it has been proposed that CDKIs may not be effective against such viruses (Schang, J. Antimicrob. Chemother. 50(6):779-92, 2002). To our knowledge, this is a first demonstration of a poxvirus being sensitive to a CDKI. Both Compound 105 and Roscovitine inhibited HAd4 replication and, interestingly, their $IC_{50}$ values were substantially lower than for Cidofovir. Likewise, HCMV was equally sensitive to Compound 105 and Roscovitine, albeit this time at molar doses higher than for Cidofovir. Both CDKIs proved ineffective against both RNA viruses tested, MV and IV.

TABLE 10

Inhibition of virus replication. $IC_{50}$ (μM) established by plaque reduction assay (n = 4)

|  | HSV-1 | HSV-1 ΔTK | HSV-2 | VV | HAd4 | HCMV | MV | IV |
|---|---|---|---|---|---|---|---|---|
| Compound 105 | 5.0 ± 0.9 | 5.3 ± 0.9 | 4.7 ± 1.0 | 3.8 ± 1.3 | 2.4 ± 1.3 | 3.2 ± 1.6 | 19.7 ± 1.8 | >20 |
| Roscovitine | >20 | >20 | >20 | >20 | 3.1 ± 1.6 | 4.9 ± 2.2 | >20 | >20 |
| Iododeoxyuridine | * |  |  | 3.7 ± 1.6 |  |  |  |  |
| Acyclovir | 0.5 ± 0.2 | 73.0 ± 18 | 2.2 ± 0.5 |  |  |  |  |  |
| Cidofovir |  |  |  |  | 16.6 ± 2.9 | 0.2 ± 0.1 |  |  |
| Ribavirin |  |  |  |  | >40 |  | 12.0 ± 1.1 | 10.5 ± 1.8 |
| Tamiflu |  |  |  |  |  |  |  | 12.5 ± 2.2 |
| Chloroquine |  |  |  |  |  |  |  | 5.3 ± 0.9 |

*values in shaded cells have not been determined

Inhibition of Viral Expression by Compound 105 and Roscovitine.

The SV40 large T antigen is pleiotropic, encoding multiple functions that regulate virus infection and promote tumorigenesis. Large T-antigen forms a stable complex with p53, and by promoting pRb dephosphorylation inactivates members of the Rb family (Zalvide et al., Mol. Cell. Biol. 18(3): 1408-15, 1998). The inactivation of p53 is critical for SV40-mediated cell transformation, whilst the concomitant destabilization of the inhibitory complex between dephosphorylated Rb and the E2F family of transcription factors facilitates the transcription of target genes to promote the cell cycle entry (Ali et al., J Virol. 78(6):2749-57, 2004).

Figure 8:
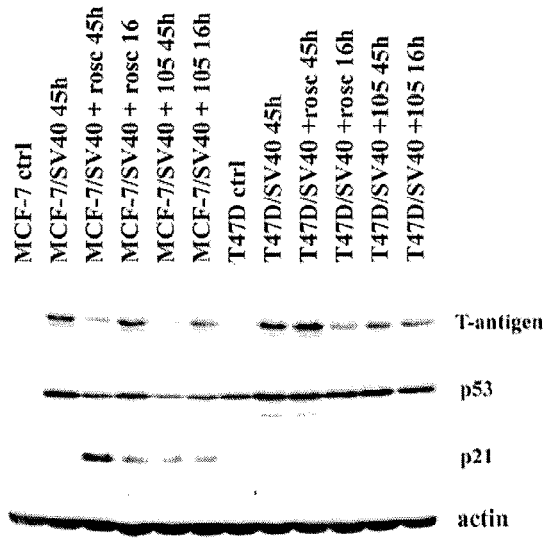
FIG. 8 displays the SV40 infection of MCF-7 (wild type p53) and T47D (mutant p53) cell lines. Expression of viral protein Large T-antigen. The p53 transcriptional activity is represented by $p21^{WAF1}$ transactivation.

MCF-7 (wild type p53) and T47D (mutant p53) cells were infected with SV40 to investigate the effect of Compound 105 and Roscovitine on the expression of the large T-antigen, p53 and $p21^{WAF1}$. The expression of large T antigen was detected irrespective of p53 status, whereas large T antigen dependent binding and stabilization of wild-type p53 resulted in its inactivation. Treatment of infected cells with Compound 105 or Roscovitine lead to a reduced level of large T-antigen, indicating an essential role of CDKs for viral genes expression (FIG. 8). The influence of CDKIs on MCF-7 cells was higher when added immediately after infection, especially in Roscovitine treated cells. Simultaneously, we observed the inhibition of p53 level and recovery of its function represented by the transactivation of p53 target protein $p21^{WAF1}$. The inhibitory effect of Compound 105 on large T-antigen expression in T47D cell line was independent of the time of treatment, while Roscovitine affected the T-antigen expression only when added 16 hours after infection. The level of mutant p53 remained unchanged and unable to trans-activate the expression of $p21^{WAF1}$ (FIG. 8).

Figure 9:
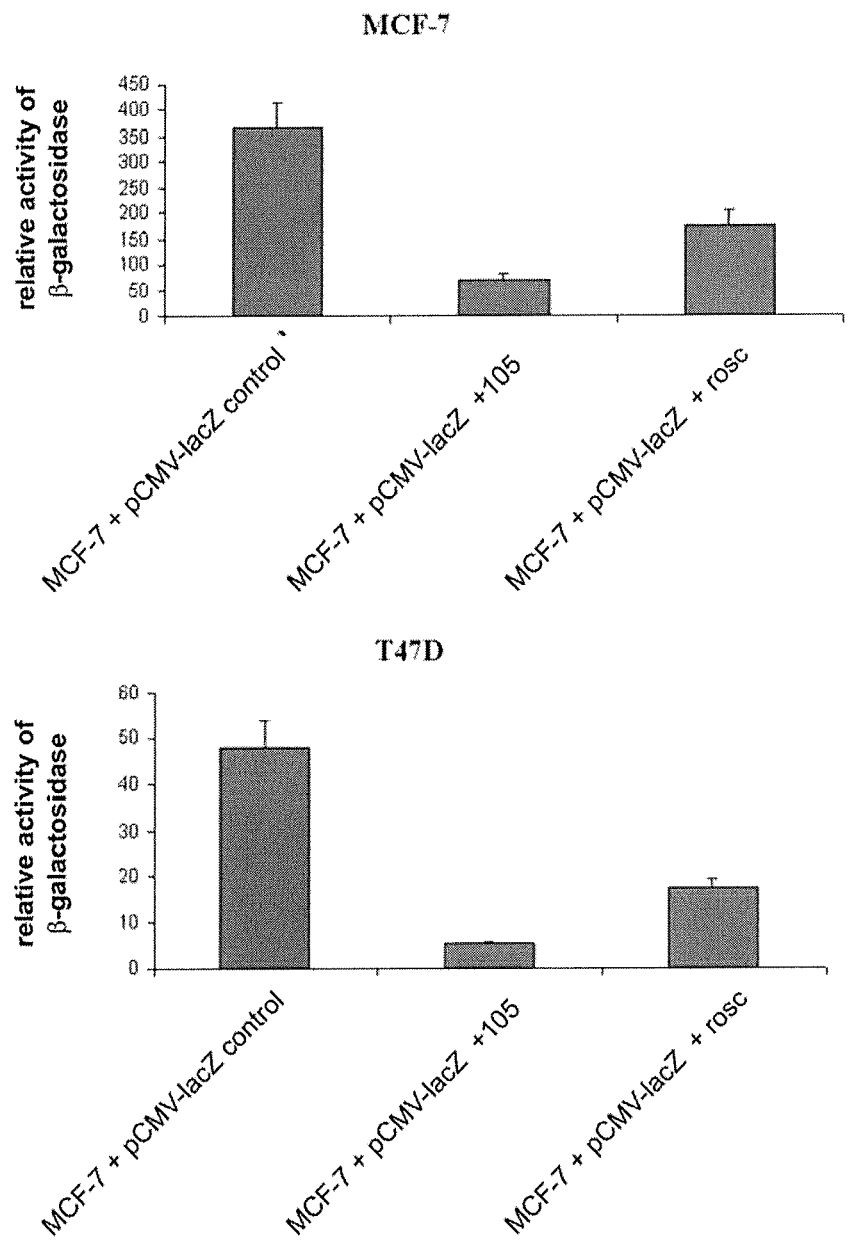
FIG. 9 displays inhibition of expression from an extrachromosomal plasmid by PCIs. Expression of (β-galactosidase from transiently transfected plasmid pCMV-lacZ in cell lines MCF-7 (wild type p53) and T47D (mutant p53).

We then tested whether the CDKIs had inhibitory effect on an isolated viral promoter in a plasmid vector. We transiently transfected MCF-7 and T47D cell lines with plasmid pCMV-lacZ, treated the transfected cells with Roscovitine or Compound 105 and measured β-galactosidase activity. Both Compound 105 and Roscovitine inhibited expression from CMV promoter in transiently transfected cells, with Compound 105 exerting a stronger suppressive effect (FIG. 9).

The Effect of CDKIs on Expression from SV40 Promoter Incorporated in the Cellular Genome.

Figure 10:
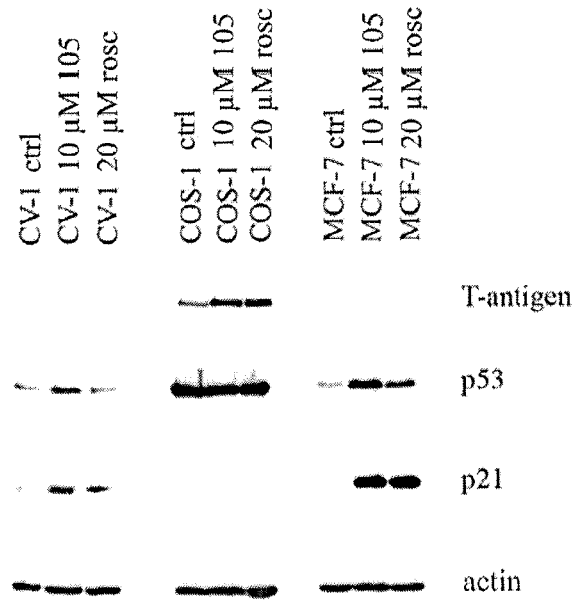
FIG. 10 displays the inhibition of expression from viral promoter incorporated to cellular genome. Induction of SV40 large T-antigen and p53 transcriptional activity ($p21^{WAF1}$ transactivation). CV-1 and MCF-7 are control cell lines (no large T antigen expression).

The observations described above lead us to expand the analysis of Compound 105 and Roscovitine to SV40 gene expression in COS-1 cells, where the sequences encoding the large T-antigen are integrated into the cellular genome. COS-1 cells are CV-1 cells transformed by origin-defective mutant of SV40, so CV-1 and MCF-7 cells were used as controls. Although expression from SV40 and the CMV major IE promoter were both inhibited by CDKIs when introduced on extrachromosomal elements (FIGS. 8 and 9), in COS-1 cells Compound 105 and Roscovitine treatment stimulated large T-antigen expression, while p53 remained constant and transcriptionally inactive ($p21^{WAF1}$ was not transactivated). In the control CV-1 and MCF-7 cells, the levels of p53 and $p21^{WAF1}$ increased after the CDKI treatment (FIG. 10). These results indicate that CDKIs may have either inhibiting or stimulating effect on a viral promoter, depending on its location within the cell.

Inhibition of Expression from the HIV Promoter.

Transcription from the HIV genome is both sensitive to CDK9 activity, and can be suppressed by CDKI treatments at concentrations that do not impair cellular transcription (Chao et al., J Biol. Chem. 2000 Sep. 15; 275(37):28345-8, 2000). Furthermore, CDK9 interacts functionally with the transactivation domain of Tat; illustrated by the fact that CDK9 depletion blocks Tat-dependent transactivation and activity.

Figure 11:
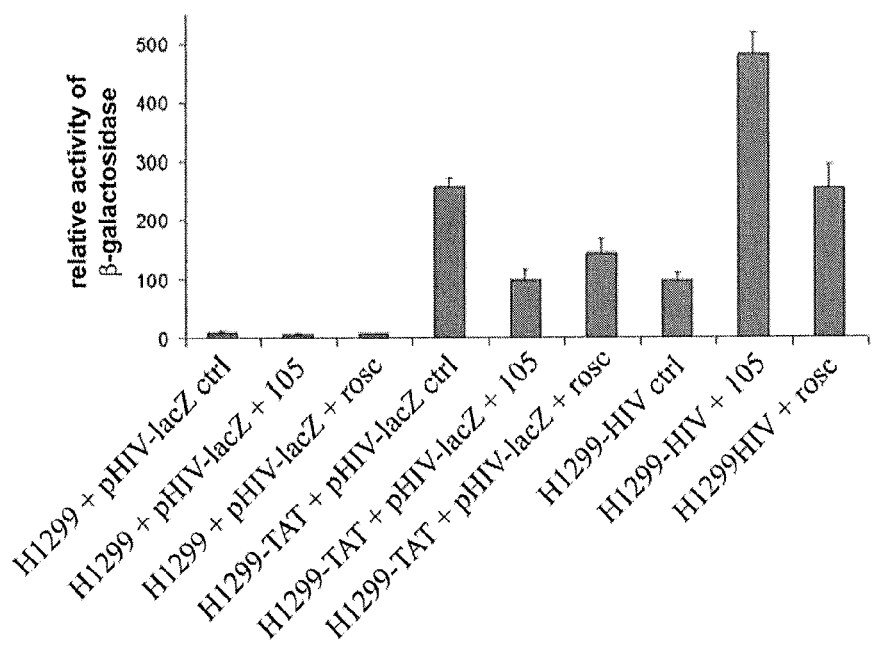
FIG. 11 displays inhibition of transcription from viral promoter by PCI depends on promoter localization. Inhibition of expression of (β-galactosidase from plasmid pHIV-lacZ transiently transfected to H1299-TAT cell line and stimulation of β-galactosidase expression from pHIV-lacZ incorporated to cellular genome (cell line H1299-HIV) after PCI treatment. H1299 cell line transiently transfected with plasmid pHIV-lacZ was used as negative control. This cell line does not produce β-galactosidase, because of absence of viral protein TAT, which is expressed from plasmid pCEP4-Tat stable transfected to H1299-TAT and H1299-HIV cell lines.

To avoid potential general inhibition of the transcription from extrachromosomal DNA by CDKI, two stable cell lines were constructed (H1299-TAT and H1299-HIV). H1299-TAT cells were transfected with pHIV-lacZ and treated with Roscovitine and Compound 105. Expression from pHIV-lacZ (extrachromosomal location) was inhibited by CDKI treatment; β-galactosidase (β-gal) readout was notably lower with Compound 105 in comparison to Roscovitine (FIG. 11). Interestingly, the effects of CDKI treatment were reversed on HIV promoter integrated into cellular DNA (H1299-HIV cells), with the reporter readout increasing 4 times following treatment with Compound 105 or 2.5 times following treatment with Roscovitine, respectively (FIG. 11).

Inhibition of Adenovirus Replication by Compound 105 and Cidofovir.

Figure 12A:
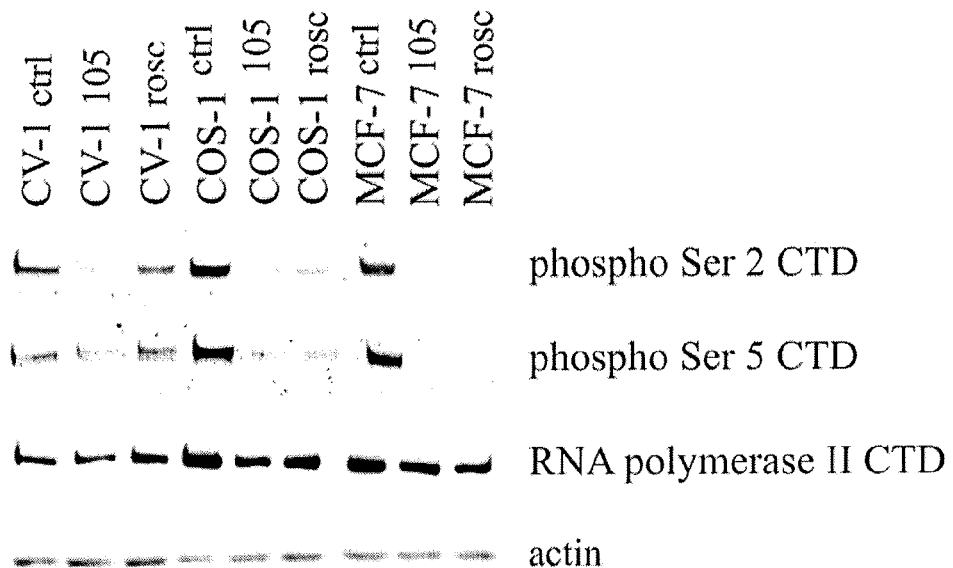
FIG. 12A displays phosphorylation of RNA polymerase II CTD in cell lines with incorporated SV40. The phosphorylation of both serine 2 and serine 5 is inhibited after 12 hours treatment with Roscovitine and 105 in all tested cell lines.
Figure 12B:
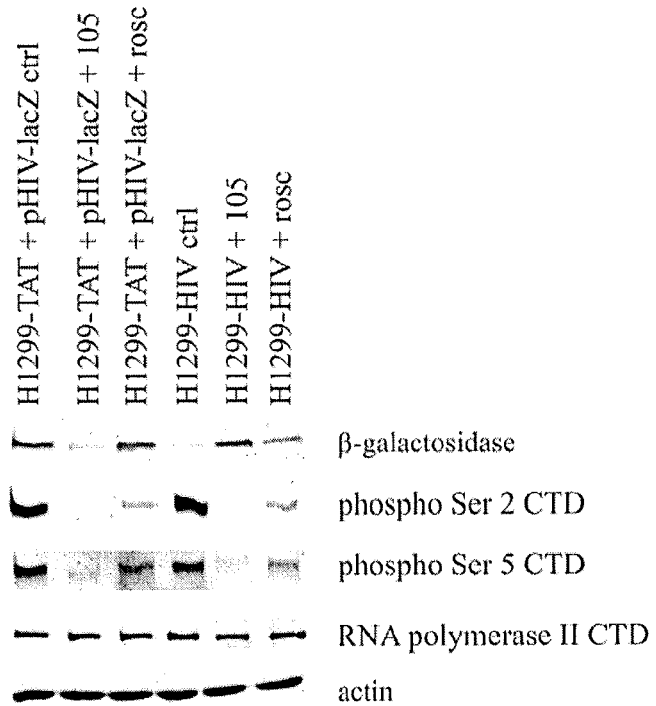
FIG. 12B displays comparison of RNA polymerase II CTD phosphorylation in cell line with incorporated (H1299-HIV) or transiently transfected (H1299-TAT) plasmid HIV-lacZ. The phosphorylation of ser 2 and ser 5 in both cell lines is inhibited after PCI treatment for 12 hours.
Figure 13:
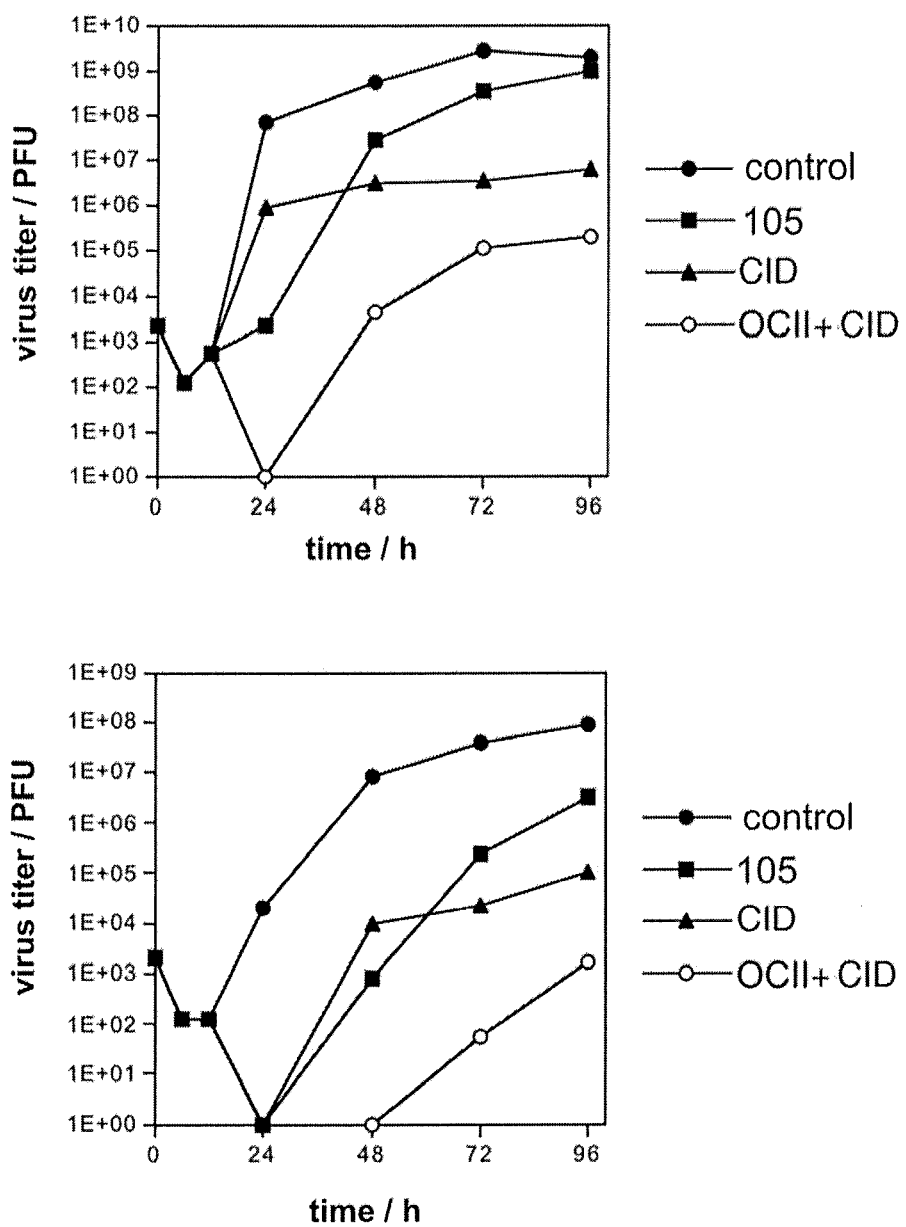
FIG. 13 displays the inhibition of HAd4 replication. Multiple step growth curve of HAd4 in presence of 10 μM Compound 105, 100 μM Cidofovir (CID) or both (Cmpd 105+CID). 0 h time point represents the virus inoculum. A. Total virus yield from the culture (cell associated+extracellular). B. Extracellular virus.
Figure 14:
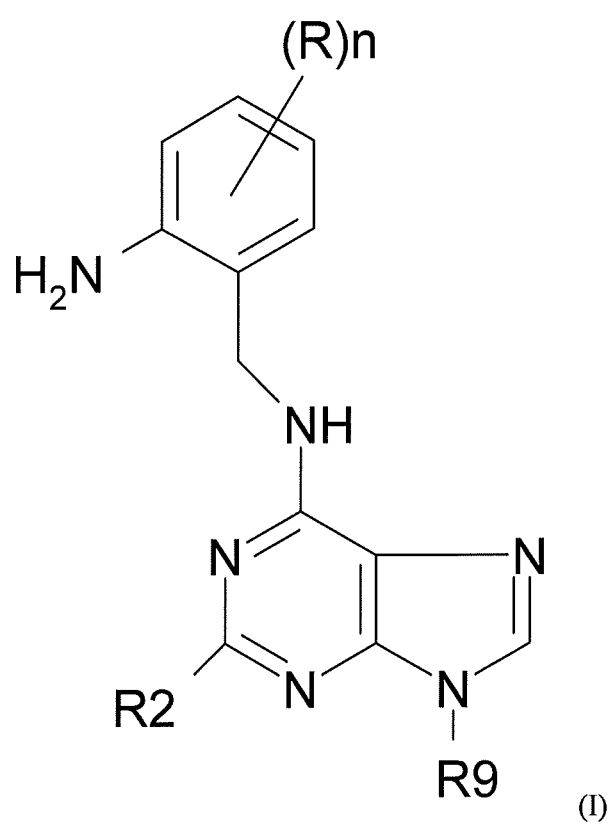
FIG. 14 shows the general formula I.

Compound 105 had a profound effect on HAdV4 replication, with a better IC50 value than even Cidofovir in a plaque reduction assay (Table 10). Since 105 and Cidofovir act by distinct mechanisms, we wished to investigate whether the two antiviral agents would have an additive effect when used in combination. A multiple step growth curve of HAd4 was therefore performed in the presence of 10 μM 105, 100 μM Cidofovir or both (FIG. 13a). As is conventional for HAdVs, the assay measured total virus yield from the cultures. At 24 hours post infection, both Cidofovir and Compound 105 inhibited the production of infectious virus, reducing virus yields by 2 and 5 logs, respectively. No infectious virus was detected when both antivirals were used in combination. At 48 hours post infection the relative efficacy of the antivirals was reversed: Compound 105 and Cidofovir reduced virus yield by 1 and 2 logs respectively, whilst the combination of both produced a 5 log reduction. At this and later time points, the effect of the two drugs in combination was greater than the additive effect of using them in isolation, and thus could be considered synergistic. However, it was clear at later time points that the effect of Compound 105 diminished until at 96 hours post infection, Compound 105 showed no overall effect on virus yield whilst Cidofovir inhibited the yield by 3 logs. The combined effect of both drugs at this time point showed a strong cumulative effect of 4 logs. The apparent disparity between the plaque reduction (Table 10) and the yield reduction (FIG. 12a) assays was resolved when the titres of cell associated and extracellular virus were split and analyzed independently. The effects of Compound 105 and Cidofovir on the yield of extracellular virus (FIG. 12b) were more consistent with the plaque reduction assay. Adenovirus is released by spontaneous lysis and plaque reduction assay relies on multiple rounds of virus replication to generate a visible plaque. The treatment of infected cells with Compound 105 considerably delayed the appearance of extracellular virus, which in turn would delay the onset of each round of replication and thus the appearance of plaques. The effect of adding Cidofovir and Compound 105 in combination on the yield of extracellular virus was dramatic (FIG. 13). This combination of the very fast early effect of Compound 105 with the delayed, but solid and long term effect of Cidofovir greatly enhanced their capacity to inhibit HAd4 replication. No infectious virus could be detected in the culture medium until 72 hours after infection and at 96 hours after infection, the virus yield was still lower than the initial virus input (0 hours), some 5 logs decrease relative to no drug treatment.

Example 9

Dry Capsules 5000 capsules, each of which contain 0.25 g of at least one of the compounds of the formula I as the active ingredient, are prepared as follows:

Composition

| | |
|---|---|
| Active ingredient | 1250 g |
| Talc | 180 g |
| Wheat starch | 120 g |
| Magnesium stearate | 80 g |
| Lactose | 20 g |

Preparation process: The powdered substances mentioned are pressed through a sieve of mesh width 0.6 mm. Portions of 0.33 g of the mixture are transferred to gelatine capsules with the aid of a capsule-filling machine.

Example 10

Soft Capsules 5000 soft gelatine capsules, each of which contain 0.05 g of at least one of the compounds of the formula I as the active ingredient, are prepared as follows:
Composition

| Active ingredient | 250 g |
|---|---|
| Lauroglycol | 2 liters |

Preparation process: The powdered active ingredient is suspended in Lauroglykol® (propylene glycol laurate, Gattefossé S.A., Saint Priest, France) and ground in a wet-pulveriser to a particle size of about 1 to 3 μm. Portions of in each case 0.419 g of the mixture are then transferred to soft gelatine capsules by means of a capsule-filling machine.

Example 11

Soft Capsules 5000 soft gelatine capsules, each of which contain 0.05 g of one of the compounds of the formula I mentioned in the preceding or following Examples as active ingredient, are prepared as follows:
Composition

| Active ingredient | 250 g |
|---|---|
| PEG 400 | 1 liter |
| Tween 80 | 1 liter |

Preparation process: The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm. Portions of in each case 0.43 g of the mixture are then transferred to soft gelatine capsules by means of a capsule-filling machine.

The invention claimed is:

1. 6-(2-aminobenzylamino)purine derivatives of general formula I

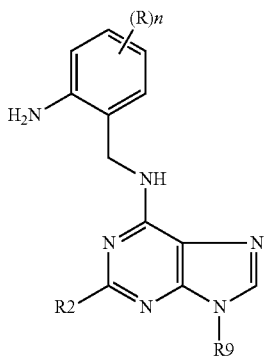

wherein $(R)_n$ represents 1 to 4 substituents (n is 1-4), which can be the same or different, the substituents being selected from the group comprising alkyl, alkoxy, amino, halogen, hydroxy, nitro and mercapto group,
and
R2 is R2'-NH— wherein
R2' is selected from the group comprising alkyl, alkenyl, cycloalkyl, cycloalkyl alkyl, aryl and arylalkyl, wherein each of the groups can optionally be substituted by one or more substituents selected from the group comprising amino, halogen, hydroxy, alkoxy or mercapto group,
and
R9 is selected from the group comprising alkyl, alkenyl, cycloalkyl, cycloalkyl alkyl, aryl and arylalkyl group, wherein each of the groups can optionally be substituted by one or more substituents selected from the group comprising amino, halogen, hydroxy, alkoxy or mercapto group,
and pharmaceutically acceptable salts thereof with alkali metals, ammonia or amines, or their addition salts with acids.

2. 6-(2-aminobenzylamino)purine derivatives according to claim 1 of the general formula I in the form of (R) or (S) isomers in case of chirality in position R2.

3. 6-(2-aminobenzylamino)purine derivatives according to claim 1, selected from the group comprising
2-({6-[(2-amino-5-chlorobenzyl)amino]-9-cyclohexyl-9H-purin-2-yl}amino)butan-1-ol,
$N^6$-(2-amino-5-chlorobenzyl)-$N^2$-(2-aminopropyl)-9-isopropyl-9H-purine-2,6-diamine,
2-({6-[(2-amino-5-chlorobenzyl)amino]-9-ethyl-9H-purin-2-yl}amino)-3-methyl-butan-1-ol,
2-({6-[(2-amino-5-chlorobenzyl)amino]-9-isopropyl-9H-purin-2-yl}amino)-3-methyl-butan-1-ol,
$N^6$-(2-amino-5-chlorobenzyl)-$N^2$-(4-aminocyclohexyl)-9-isopropyl-9H-purine-2,6-diamine,
1-({6-[(2-amino-5-chlorobenzyl)amino]-9-isopropyl-9H-purin-2-yl}amino)-2-methyl-propan-2-ol,
-({6-[(2-amino-5-chlorobenzyl)amino]-9-isopropyl-9H-purin-2-yl}amino)-2-methyl-butan-2-ol,
4-({6-[(2-amino-5-chlorobenzyl)amino]-9-isopropyl-9H-purin-2-yl}amino)-2-methyl-butan-2-ol,
4-({6-[(2-amino-5-chlorobenzyl)amino]-9-isopropyl-9H-purin-2-yl}amino)-2-methyl-pentan-2-ol,
1-({6-[(2-amino-5-chlorobenzyl)amino]-9-isopropyl-9H-purin-2-yl}amino)propan-2-ol,
4-({6-[(2-amino-5-chlorobenzyl)amino]-9-isopropyl-9H-purin-2-yl}amino)-2,3-dimethyl-butan-2-ol,
3-({6-[(2-amino-5-chlorobenzyl)amino]-9-isopropyl-9H-purin-2-yl}amino)-2-methyl-pentan-2-ol,
3-({6-[(2-amino-5-chlorobenzyl)amino]-9-isopropyl-9H-purin-2-yl]amino}pentan-2-ol,
1-({6-[(2-amino-5-chlorobenzyl)amino]-9-cyclopropyl-9H-purin-2-yl}amino)-2-methyl-propan-2-ol,
2-({6-[(2-amino-3-chlorobenzyl)amino]-9-isopropyl-9H-purin-2-yl}amino)butan-1-ol,
$N^6$-(2-amino-3-chlorobenzyl)-$N^2$-(2-aminopropyl)-9-isopropyl-9H-purine-2,6-diamine,
2-({6-[(2-amino-3-chlorobenzyl)amino]-9-isopropyl-9H-purin-2-yl}amino)-3-methyl-butan-1-ol,
$N^6$-(2-amino-3-chlorobenzyl)-$N^2$-(4-aminocyclohexyl)-9-isopropyl-9H-purine-2,6-diamine,
1-({6-[(2-amino-3-chlorobenzyl)amino]-9-isopropyl-9H-purin-2-yl}amino)propan-2-ol,
1-({6-[(2-amino-3-chlorobenzyl)amino]-9-isopropyl-9H-purin-2-yl}amino)-2-methyl-propan-2-ol,
3-({6-[(2-amino-3-chlorobenzyl)amino]-9-isopropyl-9H-purin-2-yl}amino)-2-methyl-butan-2-ol, 4-({6-[(2-amino-3-chlorobenzyl)amino]-9-isopropyl-9H-purin-2-yl}amino)-2-methyl-butan-2-ol,
4-({6-[(2-amino-3-chlorobenzyl)amino]-9-isopropyl-9H-purin-2-yl}amino)-2-methyl-pentan-2-ol,
4-({6-[(2-amino-3-chlorobenzyl)amino]-9-isopropyl-9H-purin-2-yl}amino)-2,3-dimethyl-butan-2-ol,
3-({6-[(2-amino-3-chlorobenzyl)amino]-9-isopropyl-9H-purin-2-yl}amino)-2-methyl-pentan-2-ol,
3-({6-[(2-amino-3-chlorobenzyl)amino]-9-isopropyl-9H-purin-2-yl]amino}pentan-2-ol,
2-({6-[(2-amino-5-fluorobenzyl)amino]-9-isopropyl-9H-purin-2-yl}amino)butan-1-ol,
$N^6$-(2-amino-5-fluorobenzyl)-$N^2$-(2-aminopropyl)-9-isopropyl-9H-purine-2,6-diamine,
1-({6-[(2-amino-5-fluorobenzyl)amino]-9-isopropyl-9H-purin-2-yl}amino)propan-2-ol,
2-({6-[(2-amino-5-fluorobenzyl)amino]-9-isopropyl-9H-purin-2-yl}amino)-3-methyl-butan-1-ol,
$N^6$-(2-amino-5-fluorobenzyl)-$N^2$-(4-aminocyclohexyl)-9-isopropyl-9H-purine-2,6-diamine,
1-({6-[(2-amino-5-fluorobenzyl)amino]-9-isopropyl-9H-purin-2-yl}amino)-2-methyl-propan-2-ol,
3-({6-[(2-amino-5-fluorobenzyl)amino]-9-isopropyl-9H-purin-2-yl}amino)-2-methyl-butan-2-ol,
4-({6-[(2-amino-5-fluorobenzyl)amino]-9-isopropyl-9H-purin-2-yl}amino)-2-methyl-butan-2-ol,
4-({6-[(2-amino-5-fluorobenzyl)amino]-9-isopropyl-9H-purin-2-yl}amino)-2-methyl-pentan-2-ol,
4-({6-[(2-amino-5-fluorobenzyl)amino]-9-isopropyl-9H-purin-2-yl}amino)-2,3-dimethyl-butan-2-ol,
3-({6-[(2-amino-5-fluorobenzyl)amino]-9-isopropyl-9H-purin-2-yl}amino)-2-methyl-pentan-2-ol,
3-({6-[(2-amino-5-fluorobenzyl)amino]-9-isopropyl-9H-purin-2-yl]amino}pentan-2-ol,
2-({6-[(2-amino-5-iodobenzyl)amino]-9-isopropyl-9H-purin-2-yl}amino)butan-1-ol,
$N^6$-(2-amino-5-iodobenzyl)-$N^2$-(2-aminopropyl)-9-isopropyl-9H-purine-2,6-diamine,
2-({6-[(2-amino-5-iodobenzyl)amino]-9-isopropyl-9H-purin-2-yl}amino)-3-methyl-butan-1-ol,
1-({6-[(2-amino-5-iodobenzyl)amino]-9-ethyl-9H-purin-2-yl}amino)propan-2-ol,
1-({6-[(2-amino-5-iodobenzyl)amino]-9-isopropyl-9H-purin-2-yl}amino)propan-2-ol,
$N^6$-(2-amino-5-iodobenzyl)-$N^2$-(4-aminocyclohexyl)-9-isopropyl-9H-purine-2,6-diamine,
1-({6-[(2-amino-5-iodobenzyl)amino]-9-isopropyl-9H-purin-2-yl}amino)-2-methyl-propan-2-ol,
3-({6-[(2-amino-5-iodobenzyl)amino]-9-isopropyl-9H-purin-2-yl}amino)-2-methyl-butan-2-ol,
4-({6-[(2-amino-5-iodobenzyl)amino]-9-isopropyl-9H-purin-2-yl}amino)-2-methyl-butan-2-ol,
4-({6-[(2-amino-5-iodobenzyl)amino]-9-isopropyl-9H-purin-2-yl}amino)-2-methyl-pentan-2-ol,
4-({6-[(2-amino-5-iodobenzyl)amino]-9-isopropyl-9H-purin-2-yl}amino)-2,3-dimethyl-butan-2-ol,
3-({6-[(2-amino-5-iodobenzyl)amino]-9-isopropyl-9H-purin-2-yl}amino)-2-methyl-pentan-2-ol,
3-({6-[(2-amino-5-iodobenzyl)amino]-9-isopropyl-9H-purin-2-yl]amino}pentan-2-ol,
1-({6-[(2-amino-5-iodobenzyl)amino]-9-isopropyl-9H-purin-2-yl}amino)-2-methyl-propan-2-ol,
2-({6-(2,3-diaminobenzyl)amino]-9-isopropyl-9H-purin-2-yl}amino)butan-1-ol,
$N_6$-(2,3-diaminobenzyl)amino]-$N^2$-(2-aminopropyl)-9-isopropyl-9H-purine-2,6-diamine,
2-({6-(2,3-diaminobenzyl)amino]-9-isopropyl-9H-purin-2-yl}amino)-3-methyl-butan-1-ol,
$N^6$-(2,3-diaminobenzyl)amino]-$N^2$-(4-aminocyclohexyl)-9-isopropyl-9H-purine-2,6-diamine,
1-({6-(2,3-diaminobenzyl)amino]-9-isopropyl-9H-purin-2-yl}amino)-2-methyl-propan-2-ol,
3-({6-(2,3-diaminobenzyl)amino]-9-isopropyl-9H-purin-2-yl}amino)-2-methyl-butan-2-ol,
4-({6-(2,3-diaminobenzyl)amino]-9-isopropyl-9H-purin-2-yl}amino)-2-methyl-butan-2-ol,
4-({6-(2,3-diaminobenzyl)amino]-9-isopropyl-9H-purin-2-yl}amino)-2-methyl-pentan-2-ol,
4-({6-(2,3-diaminobenzyl)amino]-9-isopropyl-9H-purin-2-yl}amino)-2,3-dimethyl-butan-2-ol,
3-({6-(2,3-diaminobenzyl)amino]-9-isopropyl-9H-purin-2-yl}amino)-2-methyl-pentan-2-ol,
3-({6-(2,3-diaminobenzyl)amino]-9-isopropyl-9H-purin-2-yl]amino}pentan-2-ol,
1-({6-[(2,3-diaminobenzyl)amino]-9-isopropyl-9H-purin-2-yl}amino)propan-2-ol,
2-({6-[(2-amino-5-methylbenzyl)amino]-9-isopropyl-9H-purin-2-yl}amino)butan-1-ol,
$N^6$-(2-amino-5-methylbenzyl)-$N^2$-(2-aminopropyl)-9-isopropyl-9H-purine-2,6-diamine,
2-({6-[(2-amino-5-methylbenzyl)amino]-9-isopropyl-9H-purin-2-yl}amino)-3-methyl-butan-1-ol,
$N^6$-(2-amino-5-methylbenzyl)-$N^2$-(4-aminocyclohexyl)-9-isopropyl-9H-purine-2,6-diamine,
1-({6-[(2-amino-5-methylbenzyl)amino]-9-isopropyl-9H-purin-2-yl}amino)-2-methyl-propan-2-ol,
1-({6-[(2-amino-5-methylbenzyl)amino]-9-isopropyl-9H-purin-2-yl}amino)propan-2-ol,
3-({6-[(2-amino-5-methylbenzyl)amino]-9-isopropyl-9H-purin-2-yl}amino)-2-methyl-butan-2-ol,
4-({6-[(2-amino-5-methylbenzyl)amino]-9-isopropyl-9H-purin-2-yl}amino)-2-methyl-butan-2-ol,
4-({6-[(2-amino-5-methylbenzyl)amino]-9-isopropyl-9H-purin-2-yl}amino)-2-methyl-pentan-2-ol,
4-({6-[(2-amino-5-methylbenzyl)amino]-9-isopropyl-9H-purin-2-yl}amino)-2,3-dimethyl-butan-2-ol,
3-({6-[(2-amino-5-methylbenzyl)amino]-9-isopropyl-9H-purin-2-yl}amino)-2-methyl-pentan-2-ol,
3-({6-[(2-amino-5-methylbenzyl)amino]-9-isopropyl-9H-purin-2-yl]amino}pentan-2-ol,
1-({6-[(2-amino-5-methylbenzyl)amino]-9-isopropyl-9H-purin-2-yl}amino)-2-methyl-propan-2-ol,
$N^6$-(2-amino-4-methylbenzyl)-$N^2$-(2-aminopropyl)-9-isopropyl-9H-purine-2,6-diamine,
2-({6-[(2-amino-5-fluorobenzyl)amino]-9-isopropyl-9H-purin-2-yl}amino)-3-methyl-butan-1-ol,
$N^6$-(2-amino-4-methylbenzyl)-$N^2$-(4-aminocyclohexyl)-9-isopropyl-9H-purine-2,6-diamine,
1-({6-[(2-amino-4-methylbenzyl)amino]-9-isopropyl-9H-purin-2-yl}amino)-2-methyl-propan-2-ol,
1-({6-[(2-amino-4-methylbenzyl)amino]-9-isopropyl-9H-purin-2-yl}amino)propan-2-ol,
3-({6-[(2-amino-4-methylbenzyl)amino]-9-isopropyl-9H-purin-2-yl}amino)-2-methyl-butan-2-ol,
4-({6-[(2-amino-4-methylbenzyl)amino]-9-isopropyl-9H-purin-2-yl}amino)-2-methyl-butan-2-ol,
4-({6-[(2-amino-4-methylbenzyl)amino]-9-isopropyl-9H-purin-2-yl}amino)-2-methyl-pentan-2-ol,
4-({6-[(2-amino-4-methylbenzyl)amino]-9-isopropyl-9H-purin-2-yl}amino)-2,3-dimethyl-butan-2-ol,
3-({6-[(2-amino-4-methylbenzyl)amino]-9-isopropyl-9H-purin-2-yl}amino)-2-methyl-pentan-2-ol, 3-({6-[(2-amino-4-methylbenzyl)amino]-9-isopropyl-9H-purin-2-yl]amino}pentan-2-ol,
1-({6-[(2-amino-4-methylbenzyl)amino]-9-isopropyl-9H-purin-2-yl}amino)-2-methyl-propan-2-ol,
$N^6$-(2-amino-3-methoxylbenzyl)-$N^2$-(2-aminopropyl)-9-isopropyl-9H-purine-2,6-diamine,
2-({6-[(2-amino-3-methoxylbenzyl)amino]-9-isopropyl-9H-purin-2-yl}amino)-3-methyl-butan-1-ol,
$N^6$-(2-amino-3-methoxylbenzyl)-$N^2$-(4-aminocyclohexyl)-9-isopropyl-9H-purine-2,6-diamine,
1-({6-[(2-amino-3-methoxylbenzyl)amino]-9-isopropyl-9H-purin-2-yl}amino)-2-methyl-propan-2-ol,
1-({6-[(2-amino-3-methoxybenzyl)amino]-9-isopropyl-9H-purin-2-yl}amino)propan-2-ol,
3-({6-[(2-amino-3-methoxylbenzyl)amino]-9-isopropyl-9H-purin-2-yl}amino)-2-methyl-butan-2-ol,
4-({6-[(2-amino-3-methoxylbenzyl)amino]-9-isopropyl-9H-purin-2-yl}amino)-2-methyl-butan-2-ol,
4-({6-[(2-amino-3-methoxylbenzyl)amino]-9-isopropyl-9H-purin-2-yl}amino)-2-methyl-pentan-2-ol,
4-({6-[(2-amino-3-methoxylbenzyl)amino]-9-isopropyl-9H-purin-2-yl}amino)-2,3-dimethyl-butan-2-ol,
3-({6-[(2-amino-3-methoxylbenzyl)amino]-9-isopropyl-9H-purin-2-yl}amino)-2-methyl-pentan-2-ol,
3-({6-[(2-amino-3-methoxylbenzyl)amino]-9-isopropyl-9H-purin-2-yl]amino}pentan-2-ol,
1-({6-[(2-amino-3-methoxylbenzyl)amino]-9-isopropyl-9H-purin-2-yl}amino)-2-methyl-propan-2-ol,
1-({6-[(2-amino-5-methoxybenzyl)amino]-9-isopropyl-9H-purin-2-yl}amino)propan-2-ol,
2-({6-[(2-amino-5-methoxylbenzyl)amino]-9-cyclohexyl-9H-purin-2-yl}amino)butan-1-ol,
$N^6$-(2-amino-5-methoxylbenzyl)-$N^2$-(2-aminopropyl)-9-isopropyl-9H-purine-2,6-diamine,
2-({6-[(2-amino-5-fluorobenzyl)amino]-9-isopropyl-9H-purin-2-yl}amino)-3-methyl-butan-1-ol,
$N^6$-(2-amino-5-methoxylbenzyl)-$N^2$-(4-aminocyclohexyl)-9-isopropyl-9H-purine-2,6-diamine,
1-({6-[(2-amino-5-methoxylbenzyl)amino]-9-isopropyl-9H-purin-2-yl}amino)-2-methyl-propan-2-ol,
3-({6-[(2-amino-5-methoxylbenzyl)amino]-9-isopropyl-9H-purin-2-yl}amino)-2-methyl-butan-2-ol,
4-({6-[(2-amino-5-methoxylbenzyl)amino]-9-isopropyl-9H-purin-2-yl}amino)-2-methyl-butan-2-ol,
4-({6-[(2-amino-5-methoxylbenzyl)amino]-9-isopropyl-9H-purin-2-yl}amino)-2-methyl-pentan-2-ol,
4-({6-[(2-amino-5-methoxylbenzyl)amino]-9-isopropyl-9H-purin-2-yl}amino)-2,3-dimethyl-butan-2-ol,
3-({6-[(2-amino-5-methoxylbenzyl)amino]-9-isopropyl-9H-purin-2-yl}amino)-2-methyl-pentan-2-ol,
3-({6-[(2-amino-5-methoxylbenzyl)amino]-9-isopropyl-9H-purin-2-yl]amino}pentan-2-ol,
1-({6-[(2-amino-5-methoxylbenzyl)amino]-9-isopropyl-9H-purin-2-yl}amino)-2-methyl-propan-2-ol.

4. A method of inducing apoptosis in mammalian cells, comprising administering 6-(2-aminobenzylamino)purine derivatives according to claim 1 to a subject in need thereof.

5. A pharmaceutical composition, which comprises at least one substituted 6-(2-aminobenzylamino)purine derivative of claim 1 and at least one pharmaceutically acceptable carrier.

6. The pharmaceutical composition of claim 5, further comprising one or more pharmaceutical excipients.

7. The pharmaceutical composition of claim 5, further comprising a cytostatic selected from the group comprising mitoxantrone, cis-platinum, methotrexate, paclitaxel, or doxorubicin.

8. The pharmaceutical composition of claim 5, further comprising a virostatic, selected from the group comprising acyclovir, cidofovir, oseltamivir phosphate, and ribavirin.

9. A method of treating a condition selected from the group consisting of leukemia, breast carcinoma, cervical carcinoma, melanoma, and osteogenic sarcoma, comprising administering 6-(2-aminobenzylamino) purine derivatives according to claim 1.

\* \* \* \* \*